US009919135B2

United States Patent
Suzuki et al.

(10) Patent No.: US 9,919,135 B2
(45) Date of Patent: Mar. 20, 2018

(54) SHEATH FOR GASTROSTOMA, SHEATHED DILATOR, SHEATH FOR GASTROSTOMA WITH INSERTION AID, GASTROSTOMY CATHETER KIT, AND METHOD OF SPLITTING SHEATH FOR GASTROSTOMA

(71) Applicants: SUMITOMO BAKELITE CO., LTD., Shinagawa-ku (JP); Yutaka Suzuki, Nasushiobara-shi (JP)

(72) Inventors: Yutaka Suzuki, Nasushiobara (JP); Hideaki Matsunami, Akita (JP); Yukihiko Sakaguchi, Akita (JP); Masao Ikeda, Akita (JP); Tomokazu Nakayama, Akita (JP); Keiji Kamada, Akita (JP); Ryo Tanaka, Akita (JP)

(73) Assignees: SUMITOMO BAKELITE CO., LTD., Shinagawa-ku (JP); Yutaka Suzuki, Nasushiobara-shi (JP)

( * ) Notice: Subject to any disclaimer, the term of this patent is extended or adjusted under 35 U.S.C. 154(b) by 308 days.

(21) Appl. No.: 14/617,450

(22) Filed: Feb. 9, 2015

(65) Prior Publication Data
US 2015/0151087 A1 Jun. 4, 2015

Related U.S. Application Data

(63) Continuation of application No. 12/745,458, filed as application No. PCT/JP2008/071832 on Dec. 1, 2008, now abandoned.

(30) Foreign Application Priority Data

Nov. 30, 2007 (JP) .................................. 2007-310789
Nov. 28, 2008 (JP) .................................. 2008-305328

(51) Int. Cl.
*A61M 25/06* (2006.01)
*A61B 17/34* (2006.01)
(Continued)

(52) U.S. Cl.
CPC ....... *A61M 25/0668* (2013.01); *A61B 5/1076* (2013.01); *A61B 17/3415* (2013.01);
(Continued)

(58) Field of Classification Search
CPC ............ A61M 25/0668; A61M 25/0662; A61J 15/003; A61J 15/0023; A61B 17/3415
See application file for complete search history.

(56) References Cited

U.S. PATENT DOCUMENTS 4,473,067 A * 9/1984 Schiff ............... A61M 39/0606
600/18
4,596,559 A 6/1986 Fleischhacker
(Continued)

FOREIGN PATENT DOCUMENTS

JP 54-160088 12/1979
JP 58-500597 4/1983
(Continued)

OTHER PUBLICATIONS

Extended European Search Report dated Dec. 15, 2011 in patent application No. 08853905.1.
International Search Report dated Jan. 27, 2009 in PCT/JP2008/071832, filed Dec. 1, 2008.

*Primary Examiner* — Bradley Osinski
(74) *Attorney, Agent, or Firm* — Oblon, McClelland, Maier & Neustadt, L.L.P.

(57) ABSTRACT

The present invention provides a sheath for gastrostoma (1), a sheathed dilator, a gastrostomy catheter kit and a method of splitting a sheath for gastrostoma. The sheath for gastrostoma (1) includes a sheath body (11) in which a gastrostomy catheter (2) is inserted and a handle (12). The sheath for gastrostoma (1) lowers the insertion resistance of a gastrostomy catheter when inserted in a fistula before insertion of the gastrostomy catheter in the fistula for replacement in the patient's body. According to the invention, a sheath for (Continued)

gastrostoma, a sheathed dilator, a sheath for gastrostoma with insertion aid, a gastrostomy catheter kit and a method of splitting a sheath for gastrostoma which can lower the insertion resistance during placement of a catheter in the patient's body, facilitate air supply control of an endoscope and stabilize endoscopic visual field during surgery are provided.

40 Claims, 43 Drawing Sheets

(51) Int. Cl.
  *A61J 15/00*    (2006.01)
  *A61M 29/00*   (2006.01)
  *A61B 5/107*    (2006.01)
  *A61M 25/00*   (2006.01)
  *A61B 5/00*    (2006.01)

(52) U.S. Cl.
  CPC ......... *A61J 15/003* (2013.01); *A61J 15/0023* (2013.01); *A61J 15/0026* (2013.01); *A61J 15/0038* (2013.01); *A61J 15/0065* (2013.01); *A61M 25/0662* (2013.01); *A61M 29/00* (2013.01); *A61B 5/42* (2013.01); *A61J 15/0007* (2013.01); *A61M 2025/0008* (2013.01); *A61M 2025/0681* (2013.01)

(56) References Cited

U.S. PATENT DOCUMENTS

| | | | |
|---|---|---|---|
| 5,387,197 A | | 2/1995 | Smith et al. |
| 5,397,311 A | * | 3/1995 | Walker .............. A61M 25/0668 |
| | | | 604/160 |
| 6,077,250 A | | 6/2000 | Snow et al. |
| 6,402,722 B1 | * | 6/2002 | Snow .................. A61J 15/0038 |
| | | | 128/DIG. 26 |
| 6,447,540 B1 | * | 9/2002 | Fontaine ................... A61F 2/95 |
| | | | 606/108 |
| 7,144,386 B2 | | 12/2006 | Korkor et al. |
| 7,303,552 B1 | * | 12/2007 | Chu .................. A61M 25/0668 |
| | | | 604/263 |
| 2007/0016134 A1 | * | 1/2007 | Suzuki ................ A61J 15/0015 |
| | | | 604/104 |

FOREIGN PATENT DOCUMENTS

| | | |
|---|---|---|
| JP | 61-010698 | 4/1986 |
| JP | 05-007026 | 1/1993 |
| JP | 2600868 Y2 | 10/1999 |
| JP | 2006-296794 | 11/2006 |
| WO | WO 94/08643 | 4/1994 |
| WO | WO 96/41653 | 12/1996 |
| WO | WO 99/17665 | 4/1999 |
| WO | WO 2004/096115 | 11/2004 |

* cited by examiner

FIG. 1A
FIG. 1B
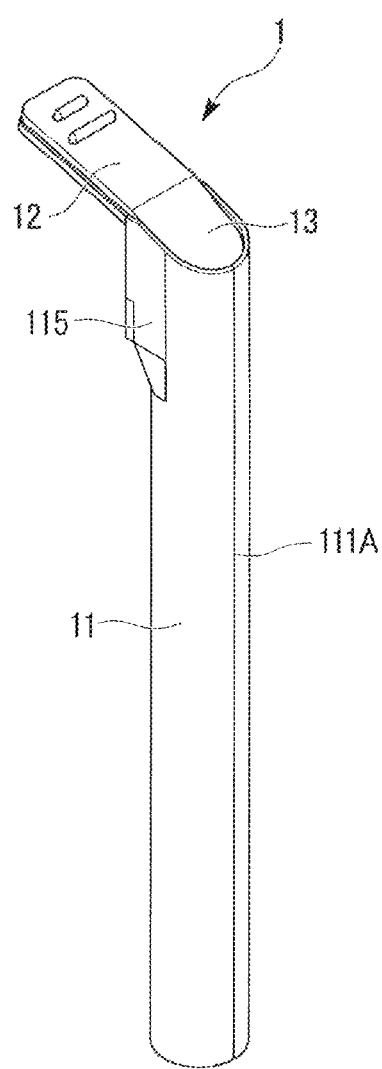
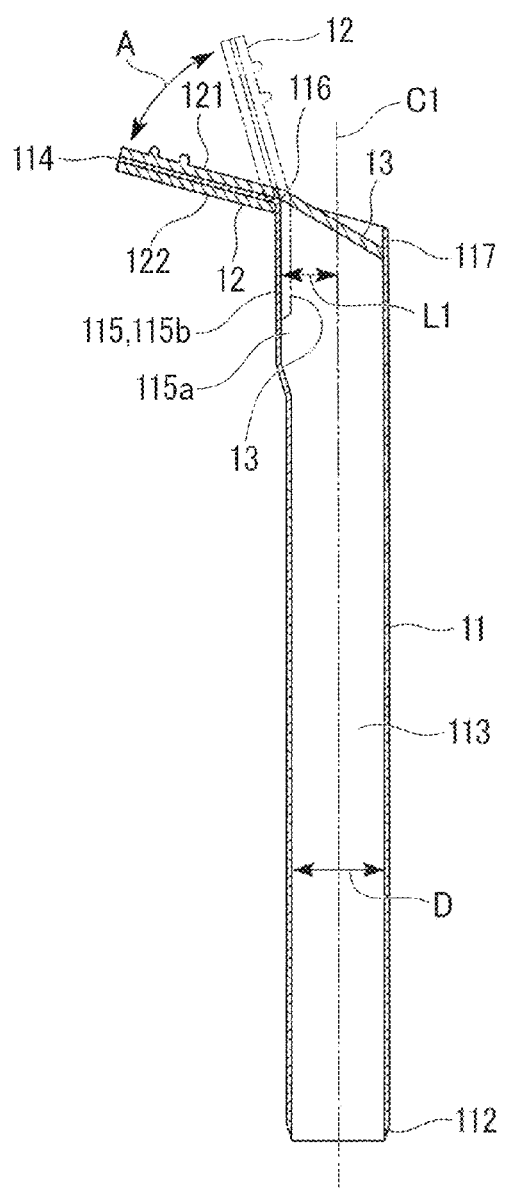

FIG. 2A
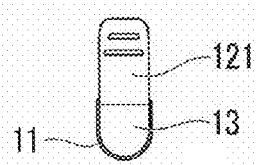
FIG. 2B       FIG. 2C       FIG. 2D
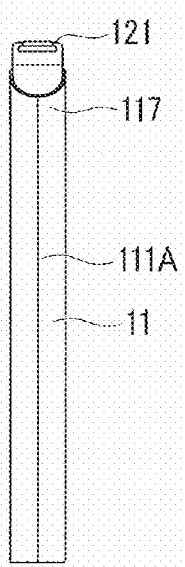 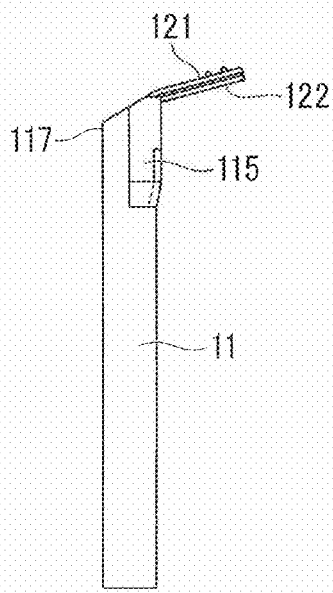 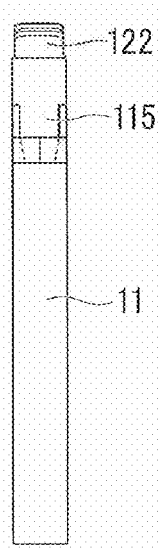
FIG. 2E
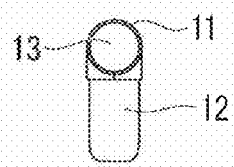

FIG. 4A
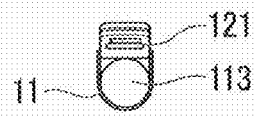
FIG. 4B          FIG. 4C          FIG. 4D
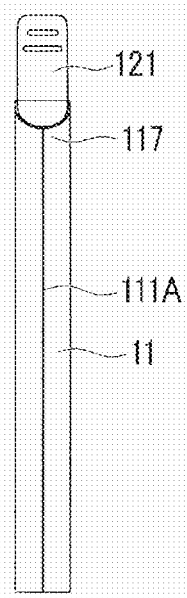 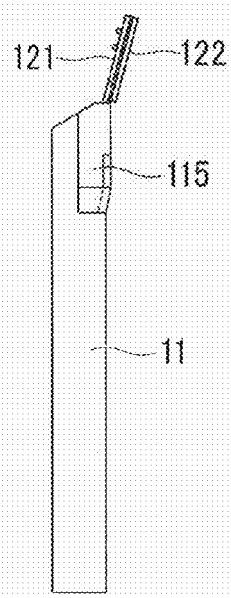 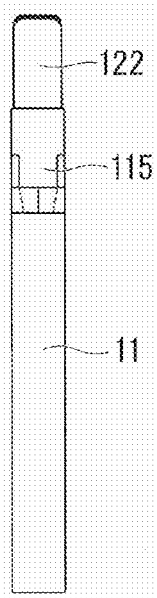
FIG. 4E
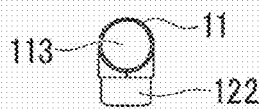

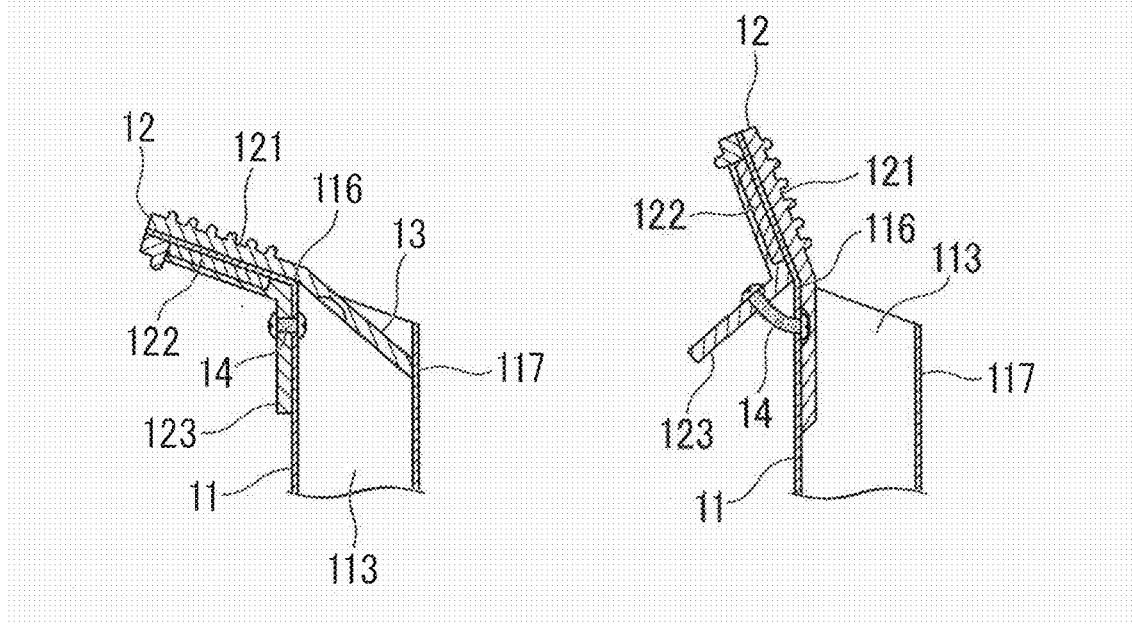

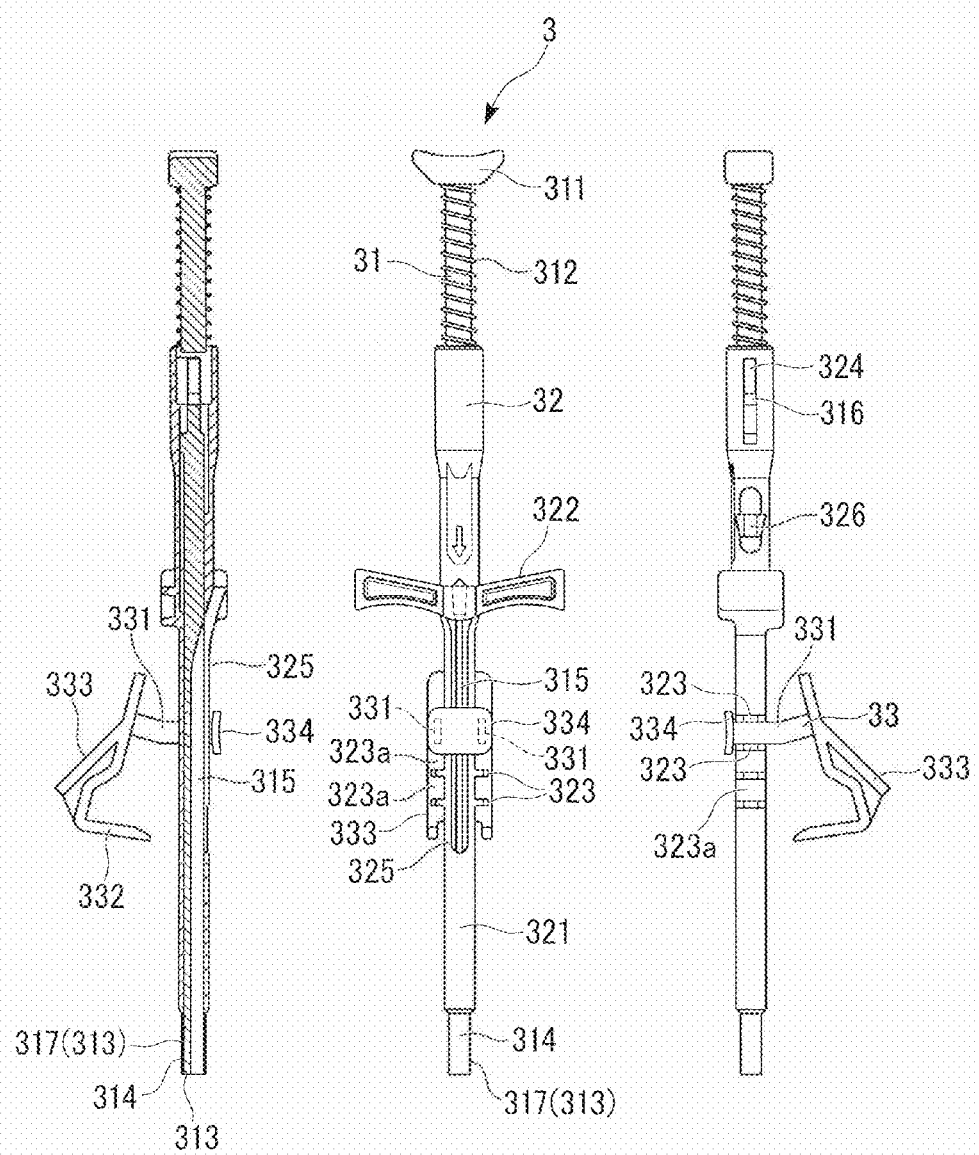

FIG. 10A
FIG. 10B
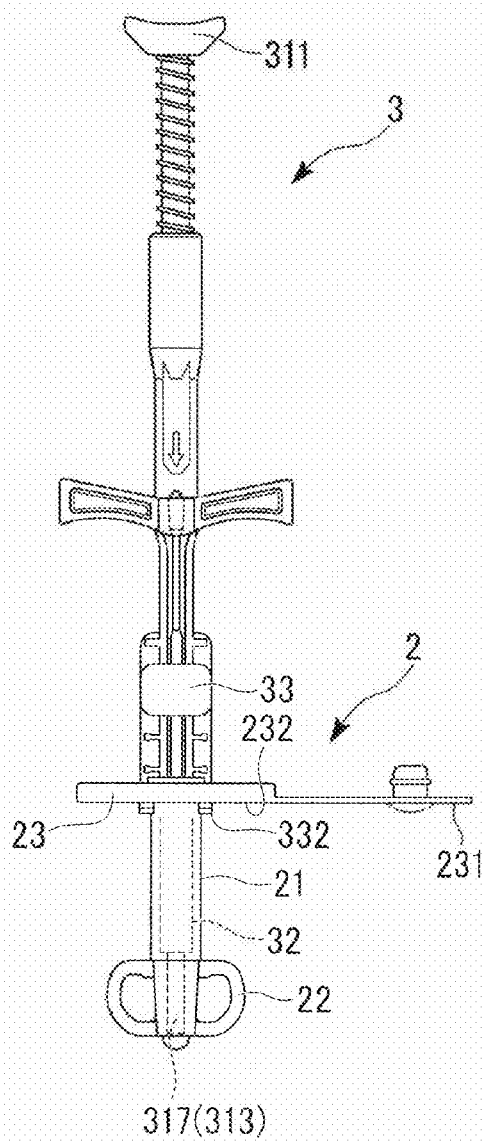
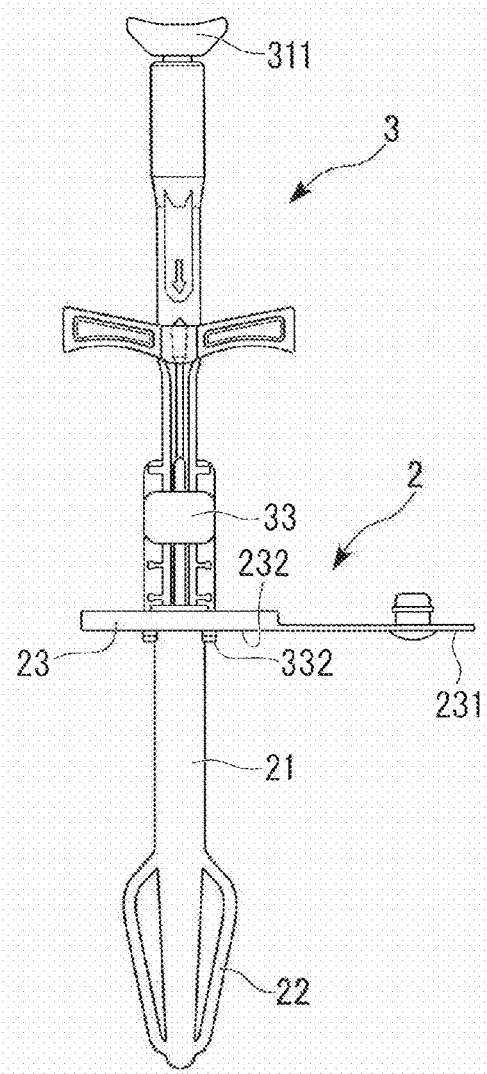

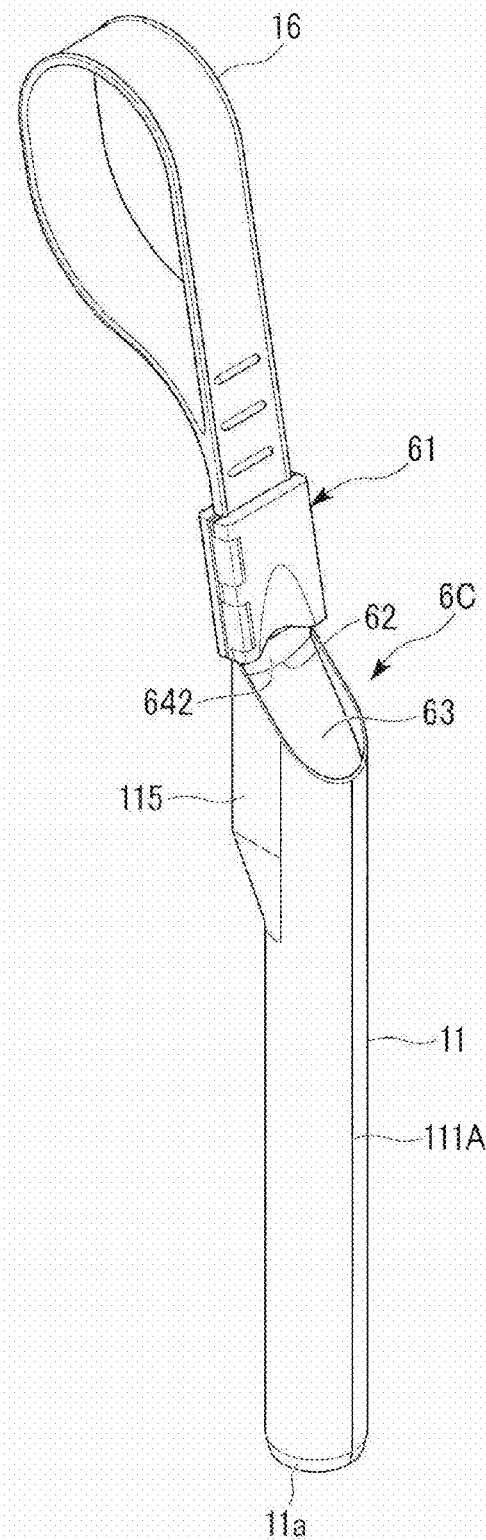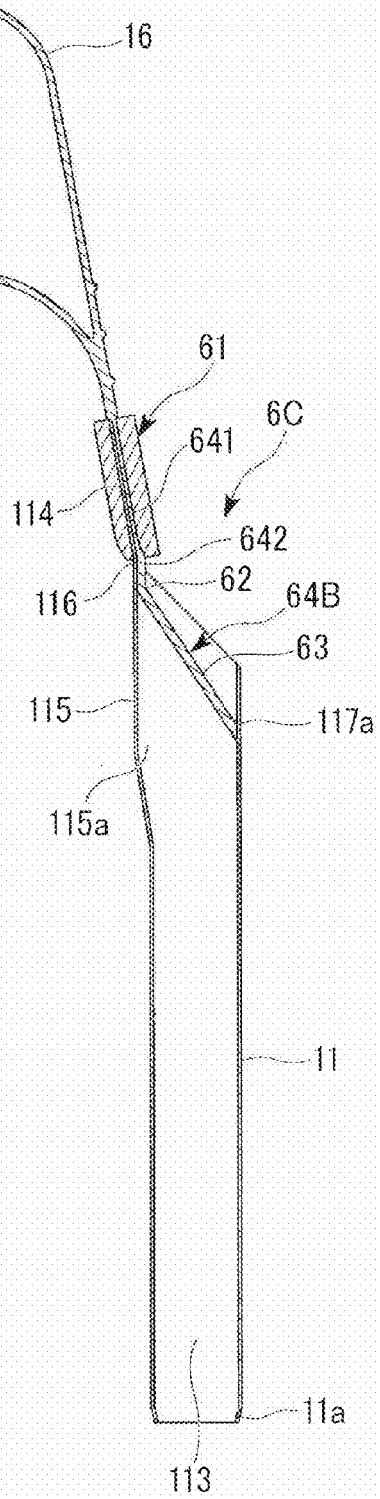

SHEATH FOR GASTROSTOMA, SHEATHED DILATOR, SHEATH FOR GASTROSTOMA WITH INSERTION AID, GASTROSTOMY CATHETER KIT, AND METHOD OF SPLITTING SHEATH FOR GASTROSTOMA

CROSS-REFERENCE TO RELATED APPLICATIONS

The present application is a continuation of and claims the benefits of priority to U.S. application Ser. No. 12/745,458, filed May 28, 2010, which is a National Stage of International Application No. PCT/JP2008/071832, filed Dec. 1, 2008, which is based on and claims the benefits of priority to Japanese Patent Application No. 2007-310789, filed Nov. 30, 2007, and to Japanese Patent Application No. 2008-305328, filed Nov. 28, 2008. The entire contents of all of the above applications are incorporated herein by reference.

TECHNICAL FIELD

The present invention relates to a sheath for gastrostoma, a sheathed dilator, a sheath for gastrostoma with insertion aid, a gastrostomy catheter kit and a method of splitting a sheath for gastrostoma, which are applied to gastrostomy in which a gastrostomy catheter is inserted in a fistula and left in a patient's body and to catheter replacement.

Patients who cannot take in nutrition through their mouths are usually given nutrients in the following three ways: intravenous nutrition administration; nasogastric nutrition administration in which a tube is inserted in the stomach or other organs through the nose; and enteral nutrition administration through a gastric fistula.

With recent developments in enteral nutrients and method of administration thereof, enteral nutrition administration through percutaneous endoscope gastrostomy (PEG) has been often employed.

Widely known methods to provide the PEG are a Pull method in which a gastric fistula tube is inserted orally, a Push method, and an Introducer method in which a tube is inserted from the patient's body surface via a sheath.

However, as to the Pull method and the Push method have the following deficiencies. Since the gastric fistula tube passes through the pharyngeal region, there is a risk of surgical site infection at a site where the gastric fistula tube is placed. In addition, it is necessary to insert the endoscope twice. On the other hand, as to in the Introducer method, since the gastric fistula tube does not pass through the pharyngeal region, the risk of surgical site infection is low and the endoscope need be inserted only once. However, the Introducer method has the following deficiency. Since it is necessary to insert a large-bore puncture needle without use of a guidewire and only a narrow-diameter balloon catheter can be placed in the patient's body via a sheath, a balloon can become deflated in a prolonged period of time, whereby management becomes complicated.

Recently, a new approach has been used widely in which a large-diameter button gastrostomy catheter is inserted from outside of the patient's body in an abdominal wall and placed directly in the stomach. In this method, an operator fixes the abdominal wall and the stomach wall together using a suture with a device for fixing the stomach wall and the abdominal wall, forms a fistula in the abdominal wall and the stomach wall using a dilator in the presence of a guidewire, inserts a large-diameter button gastrostomy catheter of which an indwelling section has been extended with the obturator in the formed fistula in the presence of the guidewire and leaves the catheter in the patient's body.

The button gastrostomy catheter used in this method is constituted of a tubular section, an indwelling section and an externally fixed section. The tubular section is provided in a state inserted in the fistula as an introduction passage for percutaneously introducing nutrients or chemicals into the stomach from outside of the patient's body. The indwelling section is attached to a distal section of the tubular section. The indwelling section is formed in a dome shape (in particular, a basket shape) from a plurality of elastically deformable arcuate strip-shaped members so as to expand radially outward of the tubular section. The externally fixed section is attached to an end (base end) of the tubular section at the side opposite to the distal section. The externally fixed section is provided to protrude radially outward of the tubular section and is made to abut the patient's body surface from outside of the body. Then, the indwelling section is deformed to adopt a reduced-diameter state (i.e., extended in a virtual extending direction of the distal end of the tubular section) using an extending device called a burator, thereby lowering insertion resistance with respect to the fistula (see, for example, Patent Document 1). The indwelling section takes a shape protruding radially outward of the tubular section in the stomach to be left there.

[Patent document 1] Japanese Unexamined Patent Application, First Publication No. 2006-296794

DESCRIPTION OF THE INVENTION

Problems to be Solved by the Invention

However, usually, a diameter of the fistula is substantially equivalent to an outer diameter of the tubular section. In addition, at the time of forming a new fistula using a dilator, the abdominal wall tries to bury the fistula after the dilator is removed from the patient's body. It is therefore expected that the diameter of the fistula becomes smaller before the gastrostomy catheter is inserted therein. To address this problem, the indwelling section of the button gastrostomy catheter may adopt a reduced-diameter state using the obturator. It is currently difficult, however, to reduce the outer diameter to become smaller than that of the tubular section. Accordingly, at the time of insertion of the button gastrostomy catheter, the indwelling section extends the fistula and thus insertion resistance becomes large.

Also, usually, the stomach is distended with sufficient air supplied from an endoscope at the time of forming a new fistula. However, in order to insert a large-diameter button gastrostomy catheter, a large fistula must be formed using the dilator. As a result, after the dilator is removed, air supplied from an endoscope escapes through the fistula, which may narrow the endoscopic visual field. In this case, air supply control is often necessary.

The invention has been made in view of the aforementioned circumstances and an object thereof is to provide a sheath for gastrostoma, a sheathed dilator, a sheath for gastrostoma with insertion aid, a gastrostomy catheter kit and a method of splitting a sheath for gastrostoma which can lower insertion resistance during placement of a catheter in the patient's body, facilitate air supply control of an endoscope and stabilize endoscopic visual field during surgery.

Means for Solving the Problems

In order to solve the aforementioned problems, the invention provides the following configurations.

A first invention provides a sheath for gastrostoma used for gastrostomy and replacement of the gastrostomy catheter in which a gastrostomy catheter is inserted in a fistula for placement, the gastrostomy catheter including a tubular section which includes an inner path for introducing a nutrient or a chemical into the stomach from outside of the body, and an indwelling section attached to a distal section of the tubular section and is formed as a dome protruding radially outward of the tubular section, the indwelling section being able to reduce its diameter by an extending force applied by an obturator, which is used to extend the indwelling section, the sheath for gastrostoma including: a cylindrical sheath body in which the gastrostomy catheter is inserted; and a handle provided to protrude at one longitudinal end of the sheath body.

A second invention provides the sheath for gastrostoma according to the first invention, further including a lid which is provided pivotably via a hinge section at a base end of the sheath body which is an end at the side of the handle and is disposed in an inner path which is a through-hole defined inside the sheath body, the lid opening and closing the inner path of the sheath body through pivotation about the hinge section, wherein: the sheath body is provided with a lid abutting section against which the lid is made to abut at a distal end which is an end opposite to the base end of the sheath body through pivotation about the hinge section; and the lid is made to abut against the lid abutting section in its closed position where the lid closes the inner path and is pivoted from the closed position toward the distal section of the sheath body to release the inner path.

A third invention provides the sheath for gastrostoma according to the second invention, wherein the lid abutting section is provided in the sheath body at a side opposite to the hinge section across the inner path and an end of the lid opposite to the side of the hinge section abuts against the lid abutting section.

A fourth invention provides the sheath for gastrostoma according to the second or third invention, wherein the handle is pivotably provided at the base end of the sheath body via the hinge section, and the lid is provided to protrude in the inner path from the handle to open and close the inner path of the sheath body through integrated pivotation with the handle.

A fifth invention provides the sheath for gastrostoma according to any one of the second to fourth inventions, wherein the hinge section is an elastic support member which elastically supports the lid at the closed position while allowing pivotation of the lid from the closed position in an open direction.

A sixth invention provides the sheath for gastrostoma according to any one of the second to fifth inventions, further including an elastic member which functions as an elastic support member that applies an urging force to the handle so as to elastically support the lid at the closed position while allowing pivotation of the lid from the closed position in an open direction.

A seventh invention provides the sheath for gastrostoma according to the first invention, further including a lid which provided in the handle via the lid hinge section and disposed in the inner path which is a through-hole defined in the sheath body, wherein: the handle is provided pivotably at the base end which is an end at the side of the handle of the sheath body via a hinge section other than the lid hinge section; and the lid is disposed in its closed position at which the lid closes the inner path and is able to open and close the inner path of the sheath body through pivotation about the lid hinge section.

An eighth invention provides the sheath for gastrostoma according to the seventh invention, wherein: the sheath body is provided with a lid abutting section against which the lid is made to abut at a distal end which is an end opposite to the base end of the sheath body through pivotation about the hinge section; and the lid is made to abut against the lid abutting section in its closed position where the lid closes the inner path and is pivoted from the closed position toward the distal section of the sheath body to release the inner path.

A ninth invention provides the sheath for gastrostoma according to the eighth invention, wherein the hinge section and the lid hinge section are provided in the sheath body at a side opposite to the lid abutting section across the inner path and an end of the lid at the side opposite to the lid hinge section is made to abut against the lid abutting section.

A tenth invention provides the sheath for gastrostoma according to any one of the seventh to ninth inventions, wherein the lid hinge section is disposed at an end of a stopper projection piece which is provided to protrude from the handle, inserted in the sheath body and is disposed along an inner surface of the sheath body at a side opposite to the lid abutting section across the inner path; and when the lid receives force to cause the same to pivot from the closed position in an open direction, the stopper projection piece is pressed against the inner surface of the sheath body to restrict pivotation of the stopper projection piece with respect to the sheath body.

An 11th invention provides the sheath for gastrostoma according to the tenth invention, wherein the stopper projection piece is made of a material with rubber elasticity.

A 12th invention provides the sheath for gastrostoma according to any one of the seventh to 11th inventions, wherein the lid hinge section is made of a material with rubber elasticity and constitutes a lid elastic support member for elastically supporting the lid at the closed position.

A 13th invention provides the sheath for gastrostoma according to any one of the seventh to 12th inventions, wherein the lid hinge section and the lid are formed integrally together from a material with rubber elasticity.

A 14th invention provides the sheath for gastrostoma according to any one of the seventh to 13th inventions, wherein a mounting section which constitutes a part of the handle, the lid hinge section and the lid is formed integrally as one component from synthetic resin.

A 15th invention provides the sheath for gastrostoma according to any one of the second to 14th inventions, wherein a recess for housing the lid is formed on an inner surface of the inner path of the sheath body.

A 16th invention provides the sheath for gastrostoma according to the 15th invention, wherein an expanded section is provided at the base end of the sheath body, the expanded section being formed so that the sheath body is expanded radially outward, wherein the recess for housing the lid is a space provided so as to extend the inner path toward the inside of the expanded section.

A 17th invention provides the sheath for gastrostoma according to any one of the first to 16th inventions, wherein a handle main piece which constitutes a part or all of the handle, the sheath body and the hinge section are formed integrally together as one component from synthetic resin.

An 18th invention provides the sheath for gastrostoma according to any one of the first to 17th inventions, wherein a grasping ring is provided at a side opposite to the hinge section of the handle to allow a user to insert fingers for grasping.

A 19th invention provides the sheath for gastrostoma according to any one of the first to 18th inventions, wherein one or more notch section(s) are formed which facilitate vertical splitting of the sheath body in a longitudinal direction.

A 20th invention provides the sheath for gastrostoma according to the 19th invention, wherein the notch section is a notched groove formed in the sheath body so as not to penetrate the sheath body in the thickness direction and an uncut portion is provided by locally reducing the thickness of the sheath body at a groove bottom side of the notched groove.

A 21st invention provides the sheath for gastro stoma according to the 20th invention, wherein the sheath body includes a V-shaped distal notch section configured to recess from an end surface at the base end of the sheath body and the notched groove is formed to extend toward a distal end of the seal body from a depth section of the distal notch section.

A 22nd invention provides the sheath for gastrostoma according to the 19th invention, wherein: the notch section is a slit formed to extend along the longitudinal direction of the sheath body, the slit being formed at a part along the longitudinal direction of the sheath body and being shorter than the entire longitudinal direction length of the sheath body; and the sheath body has a uncut portion at which no slit is formed along a virtual extended line of the slit.

A 23rd invention provides the sheath for gastrostoma according to any one of the 20th to 22nd inventions, wherein the load applied to the inner surface of the sheath body is not smaller than 0.5N to not greater than 5N in order to fracture at least one of the uncut portions.

A 24th invention provides the sheath for gastrostoma according to any one of the 19th to 23rd inventions, wherein the notch section is formed in a wedge-shaped cross-section with its opening width increasing from an inner surface toward an outer surface of the sheath body.

A 25th invention provides the sheath for gastrostoma according to any one of the 19th to 24th inventions, wherein the notch section is formed through laser processing of the sheath body.

A 26th invention provides the sheath for gastrostoma according to the 25th invention, wherein the sheath body is made of a FEP-containing material and a portion of the sheath body where the notch section has been formed is whitened by the laser processing.

A 27th invention provides the sheath for gastrostoma according to any one of the 19th to 26th inventions, wherein the handle is provided at a position where the handle does not interfere with the notch section in a circumferential direction of the sheath body.

A 28th invention provides the sheath for gastrostoma according to the 27th invention, wherein the notch section is formed only at one position along the circumferential direction of the sheath body and only one handle is provided.

A 29th invention provides the sheath for gastrostoma according to any one of the first to 28th inventions, wherein the sheath body is oriented in the longitudinal direction thereof.

A 30th invention provides the sheath for gastrostoma according to any one of the first to 29th inventions, wherein an end surface of the sheath body at the side of the base end is inclined with respect to an axial center of the sheath body.

A 31st invention provides the sheath for gastro stoma according to any one of the first to 30th inventions, wherein an inner diameter of the sheath body is larger than an outer diameter of the tubular section of the gastrostomy catheter.

A 32nd invention provides the sheath for gastro stoma according to any one of the first to 31st inventions, wherein the material of the sheath body contains fluororesin.

A 33rd invention provides the sheath for gastrostoma according to the 32nd invention, wherein the fluororesin comprises any one of PTFE, ETFE and FEP.

A 34th invention provides the sheath for gastro stoma according to any one of the first to 33th inventions, wherein the sheath body can be removably disposed outside of a dilator used for forming a fistula.

A 35th invention provides the sheath for gastro stoma according to the 34th invention, wherein the dilator includes a guidewire path which penetrates the dilator in the longitudinal direction.

A 36th invention provides the sheath for gastrostoma according to the 34th or 35th invention, wherein the dilator has a scale on a peripheral surface thereof for measurement of a distance between an inner stomach wall and a body surface.

A 37th invention provides the sheath for gastrostoma according to the 36th invention, wherein the sheath body has transparency that enables the scale of the dilator to be viewed from outside.

A 38th invention provides the sheath for gastrostoma according to any one of the 34th to 37th inventions, wherein the dilator has a narrow-diameter dilator and a large-diameter dilator which are integrated together, the narrow-diameter dilator including the guidewire path inside thereof and the large-diameter dilator being disposed outside of the narrow-diameter dilator and assembled to the narrow-diameter dilator.

A 39th invention provides the sheath for gastrostoma according to any one of the first to 38th inventions, wherein an inner diameter of the sheath body is smaller than the maximum outer diameter of the indwelling section of the gastrostomy catheter which adopts a reduced-diameter state due to the extending force applied by the obturator.

A 40th invention provides the sheath for gastrostoma according to the 39th invention, wherein the sheath body is vertically splittable when the gastrostomy catheter is inserted with the indwelling section being in its reduced-diameter state by the obturator.

A 41st invention provides the sheath for gastrostoma according to any one of the first to 40th inventions, wherein the sheath body is formed of a stretch-deformable material and is thus radially expandable.

A 42nd invention provides the sheath for gastrostoma according to any one of the first to 38th inventions, wherein an inner diameter of the sheath body is larger than the maximum outer diameter of the indwelling section of the gastrostomy catheter which adopts a reduced-diameter state due to the extending force applied by the obturator.

A 43rd invention provides the sheath for gastrostoma according to any one of the first to 42nd inventions, wherein the sheath body is configured such that a sheath insertion aid having a rod-shaped appearance can be inserted in the sheath body and the sheath insertion aid includes a rod-shaped body and a tapered distal section having a tapering configuration provided to protrude at one longitudinal end of the rod-shaped body.

A 44th invention provides the sheath for gastrostoma according to the 43rd invention, wherein the sheath insertion aid includes a guidewire insertion hole which penetrates the sheath insertion aid along the longitudinal direction.

A 45th invention provides the sheath for gastrostoma according to the 43rd or 44th invention, wherein the sheath insertion aid can function as a dilator used for forming a fistula.

A 46th invention provides a sheathed dilator in which the sheath for gastrostoma according to any one of the first to 45th inventions is disposed outside the dilator used for forming a fistula.

A 47th invention provides a sheath for gastrostoma with insertion aid in which a sheath insertion aid is inserted in the sheath body of the sheath for gastrostoma according to any one of the first to 45th inventions, the sheath insertion aid being provided to protrude at a tapered distal section having a tapering configuration at one longitudinal end of a rod-shaped body.

A 48th invention provides a gastrostomy catheter kit, including: a gastrostomy catheter for percutaneously feeding a nutrient or a chemical into the patient's stomach from outside of the body; an obturator; and one of the sheath for gastrostoma according to any one of the first to 45th inventions and the sheathed dilator according to the 46th invention. The gastrostomy catheter includes a tubular section which includes an inner path for introducing a nutrient or a chemical into the stomach from outside of the body, and an indwelling section which is attached to a distal section of the tubular section and is formed as a dome protruding radially outward of the tubular section, in which the indwelling section can reduce its diameter due to the extending force applied by an obturator for extending the indwelling section; the gastrostomy catheter in which indwelling section being its reduced-diameter state by the obturator is inserted in a sheath for gastrostoma of the sheath for gastrostoma according to claim 1 and a sheath for gastrostoma of the sheathed dilator according to claim 46 while the sheath for gastrostoma is inserted in a fistula.

A 49th invention provides the gastrostomy catheter kit according to the 48th invention, wherein: the obturator includes an outer case, a pushing rod for extension which includes a rod body inserted in the outer case to be movable in a longitudinal direction of the outer case and a stopper for anchoring the gastrostomy catheter to the outer case; and in a state in which the gastrostomy catheter is anchored to the outer case with the stopper, an operator inserts a distal end of the pushing rod for extension protruding from the outer case of the rod body in the indwelling section of the gastrostomy catheter and presses the most distal section of the indwelling section so as to extend the indwelling section.

A 50th invention provides the gastrostomy catheter kit according to the 48th or 49th invention, wherein the gastrostomy catheter and the obturator include a guidewire path and the obturator is configured to reduce the diameter of the indwelling section of the gastrostomy catheter in a state in which the obturator is disposed outside of the guidewire which is inserted in the gastrostomy catheter.

A 51st invention provides the gastrostomy catheter kit according to any one of the 48th to 50th inventions, further including the sheath for gastrostoma according to any of the first to 45th inventions as a sheath for gastrostoma used for replacement, wherein the gastrostomy catheter in which the indwelling section is in its reduced-diameter state by the obturator is inserted in the sheath for gastrostoma.

A 52nd invention provides the gastrostomy catheter kit according to the 51st invention, including a sheath for gastrostoma with insertion aid according to claim 47 configured by using the sheath for gastrostoma used for replacement.

A 53rd invention provides a method of splitting a sheath for gastrostoma, including splitting one or more parts of a sheath body in a circumferential direction along the entire longitudinal direction length of the sheath body by inserting, in a sheath body of the sheath for gastrostoma according to any one of the first to 45th inventions, a medical device having an outer diameter larger than an inner diameter of the sheath body.

A 54th invention provides the method of splitting a sheath for gastrostoma according to the 53rd invention, wherein the medical device is a gastrostomy catheter of which the indwelling section is in its reduced-diameter state due to the extending force from the obturator, and the maximum outer diameter of the indwelling section which adopts a reduced-diameter state due to the extending force applied by the obturator is larger than an inner diameter of the sheath body.

Effect of the Invention

According to the invention, it is possible to lower insertion resistance during placement of a button gastrostomy catheter.

It is also possible to open and close an inner path easily with a configuration in which the inner path of a sheath body is opened and closed with a plug member which is removably fit into a base end of the sheath body and a configuration (a second invention) in which a sheath for gastrostoma itself includes a lid which functions as a plug member to open and close the inner path of the sheath body. With such configurations, air supply from an endoscope can be controlled easily and an endoscopic visual field can be stabilized during surgery.

BRIEF DESCRIPTION OF THE DRAWINGS

FIG. 1A is a perspective view of a sheath for gastrostoma according to the invention with a lid closed.

FIG. 1B is a left cross-sectional view of the sheath for gastrostoma according to the invention with the lid closed.

FIG. 2A is a top view of the sheath for gastrostoma according to the invention with the lid closed.

FIG. 2B is a front view of the sheath for gastrostoma according to the invention with the lid closed.

FIG. 2C is a right side view of the sheath for gastrostoma according to the invention with the lid closed.

FIG. 2D is a rear view of the sheath for gastrostoma according to the invention with the lid closed.

FIG. 2E is a bottom view of the sheath for gastrostoma according to the invention with the lid closed.

FIG. 4A is a top view of the sheath for gastrostoma according to the invention with the lid opened.

FIG. 4B is a front view of the sheath for gastrostoma according to the invention with the lid opened.

FIG. 4C is a right side view of the sheath for gastrostoma according to the invention with the lid opened.

FIG. 4D is a rear view of the sheath for gastrostoma according to the invention with the lid opened.

FIG. 4E is a bottom view of the sheath for gastrostoma according to the invention with the lid opened.

FIG. 5A is a cross-sectional view of a configuration in which the sheath for gastrostoma according to the invention includes an elastic member disposed outside of a base end of a sheath body as an elastic support member for elastically supporting the lid at a closed position, illustrated with the lid being at its closed position.

FIG. 5B is a cross-sectional view of a configuration in which the sheath for gastrostoma according to the invention includes an elastic member disposed outside of a base end of a sheath body as an elastic support member for elastically supporting the lid at a closed position, illustrated in a state in which the lid is moved from its closed position to release an inner path of the sheath body.

FIG. 8A is a left cross-sectional view of an obturator and a side view of a stopper used in the invention.

FIG. 8B is a front view of the obturator used in the invention.

FIG. 8C is a right side view of the obturator used in the invention.

FIG. 10A is a front view illustrating a state in which the button for gastrostoma and the obturator used in the invention are assembled together.

FIG. 10B is a front view illustrating a state in which the button for gastrostoma and the obturator used in the invention are assembled together and the button for gastrostoma is extended.

FIG. 45A is a perspective view of an exemplary sheath for gastrostoma having a configuration in which a grasping ring is provided in the handle.

FIG. 45B is a left cross-sectional view of a structure of the sheath for gastrostoma of FIG. 45A.

REFERENCE NUMERALS

Figure 3A:
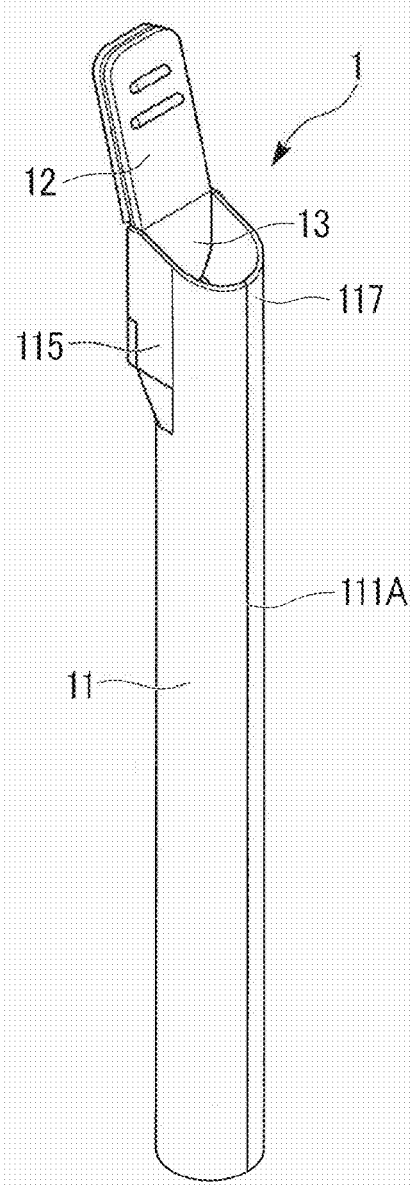
FIG. 3A is a perspective view of the sheath for gastrostoma according to the invention with the lid opened.

1: sheath for gastrostoma
11: sheath body
11a: tapered distal end
11b: sheath body
111a: notch section (notched groove)
111a: uncut portion
111b: notch section (slit)
112: tapered portion
113: inner path
114: handle main piece (tubular piece)
115: expanded section (forming section)
115a: inner space
115b: back wall section
116: hinge section
117: lid abutting section
117a: lid abutting section
117b: lid abutting section
118: uncut portion
119: split piece
12: handle
121: handle member (first handle member)
122: handle member (second handle member)
123: inclined piece
13: lid
14: elastic member
15: sheath body
151: end notch section
152: depth section
16: grasping ring
2: gastrostomy catheter (button for gastro stoma)
21: tubular section
21c: central axis
22: indwelling section
221: strip-shaped piece
222: base end gathering section
223: distal end gathering section
23: externally fixed section
231: flexible section
232: patient contact surface
24: path
25: valve
251: slit
26: communication path
27: rod abutting section
271: rod fitting projection
272: reinforcing member
28: cap
3: obturator
31: pushing rod for extension
311: operating section
312: spring
313: rod body
314: reinforcing member
315: wire insertion groove
316: lock piece
317: distal section
32: outer case
321: cylindrical portion
322: finger plate
323: fitting portion
323a: fit-in groove
324: groove
325: groove hole
326: lock hole
33: stopper
331: arm
332: holding section
333: back plate
334: pushed-in portion
4: guidewire
5: dilator (extender)
5a: sheathed dilator
51: large-diameter dilator 511: large-diameter dilator body section
512: large-diameter dilator distal section
513: large-diameter dilator side connector
514: scale
5141: reference point (zero point)
52: narrow-diameter dilator
521: narrow-diameter dilator body section
522: narrow-diameter dilator distal section
523: narrow-diameter dilator side connector
524: guidewire path
6: sheath for gastrostoma
6a: sheath for gastrostoma
6b: sheath for gastrostoma
61: handle
611: handle member (lid side handle member)
612: handle member (main piece side handle member)
62: lid hinge section
63: lid
64: elongated plate lid member
64a: elongated plate lid member
64b: elongated plate lid member with ring
641: mounting section
642: stopper projection piece
7: sheath insertion aid
70: sheath for gastrostoma with insertion aid
71: rod-shaped body
72: tapered distal section
73: guidewire insertion hole
900: abdominal wall
901: stomach wall
902: suture

BEST MODE FOR CARRYING OUT THE INVENTION

Below, referring now to the drawings, preferred embodiments of the invention will be described. Examples of a sheath for gastrostoma, a sheathed dilator, a gastrostomy catheter kit and a method for splitting a sheath for gastrostoma to which the invention is applied will be described. Although upper and lower directions are defined in the following description, these are for descriptive purposes to simply define relative positions of components of the invention. Thus, these directions do not limit directions in production and usage for implementation of the invention.

Also, in all the drawings, the same components will be denoted by the same reference numerals and duplicated description will be omitted. In the drawings, upper ends of components are illustrated at an upper side and lower ends of components are illustrated at a lower side.

FIGS. 1A, 1B and 2A to 2E illustrate an embodiment of the invention with a lid 13 of a sheath for gastrostoma 1 closed. FIG. 1A is a perspective view, FIG. 1B is a cross-sectional view, FIG. 2A is a top view, FIG. 2B is a front view, FIG. 2C is a right side view, FIG. 2D is a bottom view and FIG. 2E is a rear view.

Figure 21:
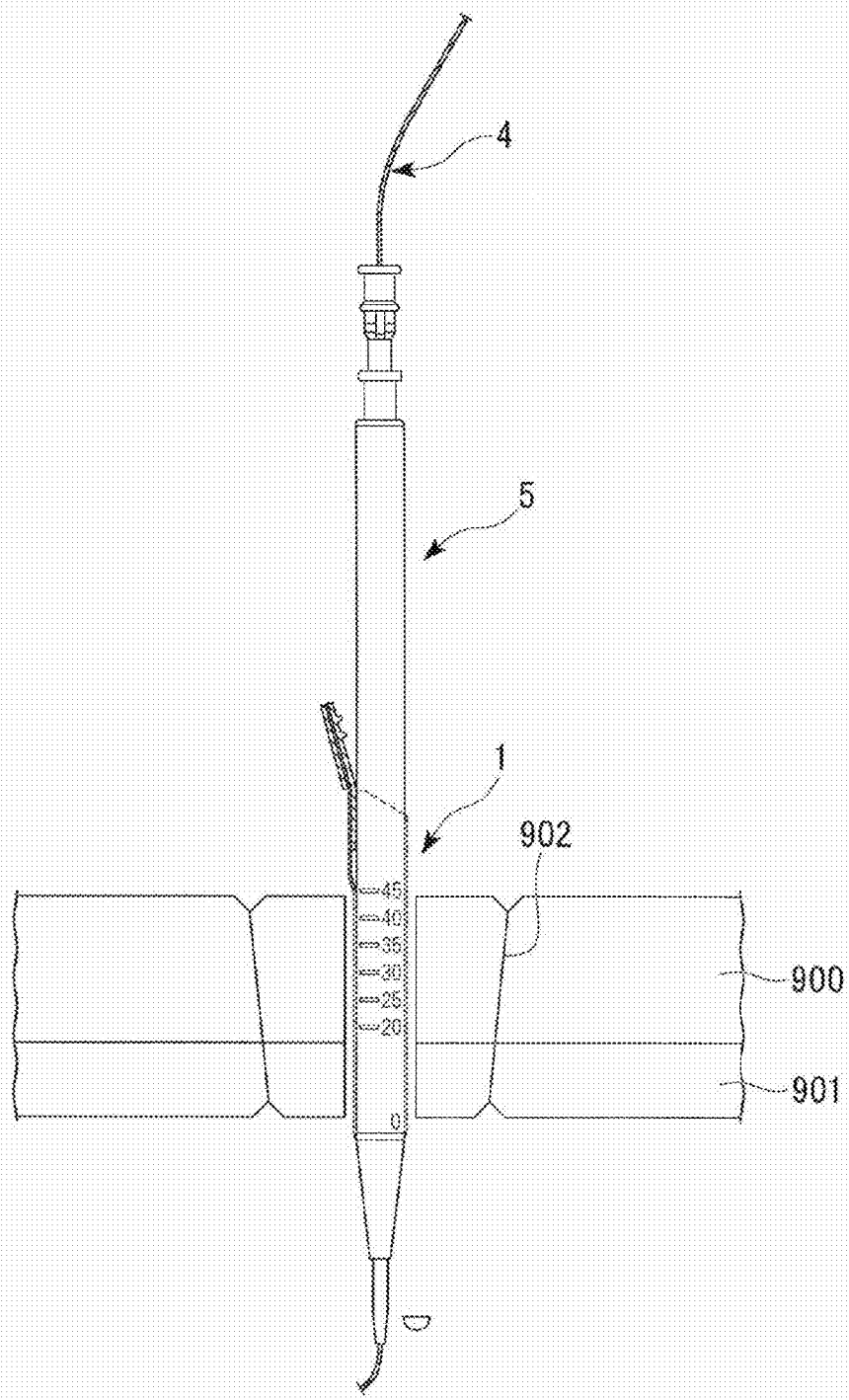
FIG. 21 illustrates a state in which a dilator covered with the sheath for gastrostoma (i.e., a sheathed dilator) is being inserted in the abdominal wall and the stomach wall using a guidewire.

The sheath for gastrostoma 1 is inserted in a fistula formed using a dilator in gastrostomy (see FIG. 21). A gastrostomy catheter is inserted in the sheath which has been inserted in the fistula.

As illustrated in FIGS. 1A, 1B and 2A to 2E, the sheath for gastrostoma 1 is constituted of a cylindrical sheath body 11 (i.e., a sheath tube), a handle 12, and a lid 13.

The sheath body 11 includes an inner path 113 through which a gastrostomy catheter (i.e., a button for gastrostoma, see FIG. 6A and other drawings) is inserted. In addition, the inner path 113 is also used when the sheath for gastrostoma 1 (in particular, the sheath body 11) is disposed to cover a dilator illustrated in FIG. 12A in order to form a hole (hereinafter referred to as a fistula) for placing the button for gastrostoma.

The handle 12 is provided at an upper end of the sheath for gastrostoma 1. The handle 12 may be used when the sheath for gastrostoma 1 is grasped during insertion of the button for gastrostoma.

The handle 12 is constituted of a first handle member 121 and a second handle member 122 fixed to a tongue-shaped handle main piece 114 extending from one longitudinal end (i.e., an end of the sheath body 11 at the side of the handle 12: an upper end in FIGS. 1A to 1E, which is hereinafter referred to as a base end) of the sheath body 11. The first handle member 121 and the second handle member 122 are planar members and are integrally fixed to the handle main piece 114 so as to sandwich the same. The handle 12 extends from the base end of the sheath body 11 as a tongue-shaped piece.

The handle main piece 114 is cut out of a resin tube together with the sheath body 11 during production of the sheath body 11. The handle main piece 114 is formed so as to be continuous to and integral with the sheath body 11. In addition, the fixing strength of the handle can be increased by an adhesive applied between the handle main piece 114 and the first handle member 121 and between the handle main piece 114 and the second handle member 122.

Note that the first handle member 121 and the second handle member 122 may be provided as separate members or may be formed integrally with each other.

Alternatively, the entire handle 12 may be constituted only of the handle main piece 114.

The handle 12 can be pivoted with respect to the sheath body 11 about a boundary section between the sheath body 11 and the handle main piece 114, which is a tongue-shaped extending portion formed continuously from the sheath body 11. That is, the boundary section functions as a hinge section 116 which enables pivotation of the handle 12 with respect to the sheath body 11. The handle 12 is provided to be pivotable with respect to the sheath body 11 via the hinge section 116.

The handle 12 pivots about the hinge section 116, i.e., about a pivot axis extending perpendicular to the axis of the sheath body 11 (i.e., a central axis of the inner path 113 denoted by reference numeral C1 in FIG. 1B). The handle 12 pivots about the hinge section 116 as illustrated by an arrow A in FIG. 1B.

In addition, the hinge section 116 may be machined to easily bend by, for example, making a cut in the boundary section, chipping to reduce thickness, and pressing a hot plate or heat ray against the hinge section to reduce thickness.

Furthermore, a resin molding product integrally constituted of the sheath body 11, the hinge section 116 and the handle main piece 114 may also be obtained through metal molding.

The handle 12 may be pivoted integrally with the lid 13, which opens and closes the inner path 113, which is a through-hole penetrating an inner side of the sheath body 11, which will be described later.

The lid 13 will now be described.

In the exemplary sheath for gastrostoma 1 illustrated in FIGS. 1A, 1B, 2A to 2E and other drawings, in particular, the lid 13 is a tongue-shaped portion configured by the first handle member 121 which is fixed to the handle main piece 114, and the lid 13 extending from the handle 12 toward the inner path 113 of the sheath body 11. The lid 13 is disposed in the inner path 113 of the sheath body 11.

The first handle member 121 is disposed on an upper surface of the handle main piece 114 (i.e., an upper surface of the handle main piece 114 at a state with the lid closed as illustrated by solid lines in FIGS. 1A and 1B). That is, the first handle member 121 is provided on a surface which continues from an inner surface of the sheath body 11 via the hinge surface 116. The lid 13 extends into the inner path 113 of the sheath body 11 from the hinge section 116 while being inclined toward a distal section of the sheath body 11 (i.e., an end opposite to the base end at the side of the handle 12 in the longitudinal direction of the sheath body 11 and the lower end in FIGS. 1A and 1B) with respect to a virtual vertical plane extending perpendicular to an axial center of the sheath body 11.

The lid 13 pivots about the hinge section 116 within the inner path 113. The pivot axis of the lid 13 about the hinge section 116 is located at a rim section of the base end of the sheath body 11.

A pivotation radius of the lid 13 about the hinge section 116 is larger than an inner diameter D (i.e., an inner diameter of a portion where no expanded section 115, which will be described later, is formed) of the inner path 113 of the sheath body 11.

In addition, in the sheath for gastrostoma 1 of the illustrated example, the expanded section 115 (allocated type section) which carried out the allocated type in detail so that a part of circumferential direction of the base end of the sheath body 11 is expanded radially outward of the sheath body 11 is formed. The hinge section 116 is provided in the expanded section 115 and disposed at the rim section of the base end of the sheath body 11 so that a distance from the axial center of the sheath body 11 (i.e., a central axis C1 of the inner path 113) is larger than the radius of the inner path 113 by the dimension of space (i.e., an inner space 115a) provided inside the expanded section 115 which extends the inner path 113.

The expanded section 115 extends laterally from the sheath body 11 and has a U-shaped cross section (i.e., a U-shaped cross section along a plane perpendicular to the axial center of the sheath body 11). The hinge section 116 is provided at a back wall section 115b located behind the inner space 115a of the expanded section 115 from the axial center (i.e., the central axis C1 of the inner path 113) of the sheath body 11. However, a pivotation radius of the lid 13 about the hinge section 116, i.e., a distance between a pivotal center and a distal end of a portion extending from the hinge section 116 of the lid 13 and placed in the inner path 113 of the sheath body 11 is larger than the sum of the radius of the inner path 113 of the sheath body 11 and a distance L1 from the axial center of the sheath body 11 (i.e., the central axis C1) to the back wall section 115b of the expanded section 115.

In FIG. 1, the reference numeral 117 denotes a lid abutting section which a distal end of the lid 13 abuts.

The lid abutting section 117 is located at the base end of the sheath body 11 at an opposite side to the hinge section 116 across the inner path 113. The lid 13 pivots about the hinge section 116 and the distal end thereof abuts the lid abutting section 117 from the side of the distal section of the sheath body 11. The lid 13 is in its closed position to close the inner path 113 at which the distal end of the lid 13 abuts against the lid abutting section 117. When the lid 13 abuts against the lid abutting section 117, the lid abutting section 117 functions as a stopper which restricts pivotation of the lid 13 from a closed position toward a direction opposite to the distal section of the sheath body 11. With this configuration, the lid 13 does not protrude from an opening of the inner path 13 at the base end of the sheath body 11 and stays only within the sheath for gastrostoma 1.

Note that the lid abutting section 117 is not necessarily located at the side opposite to the hinge section 116 across the inner path 113 in the base end of the sheath body 11. Alternatively, for example, the entire base section of the sheath body may function as a lid abutting section in accordance with configurations of the lid 13.

The lid 13 is supported at the closed position by the bending property imparted to the hinge section 116. In addition, preferably, the lid 13 is urged to abut the lid abutting section 117 by the bending property imparted to the hinge section 116 (i.e., urged with elasticity of the hinge section 116).

That is, the lid 13 is in its closed position as illustrated in FIG. 1 in a natural state in which no force is applied to the sheath for gastrostoma 1. The hinge section 116 functions as an elastic support member which elastically supports the lid 13 at the closed position. When the lid 13 pivots about the hinge section 116 to move apart from the lid abutting section 117, elasticity of the hinge section 116 applies an urging force to the lid 13 so that the lid 13 returns to the closed position. With this configuration, the inner path 113 can be closed with the lid 13 unless an operator grasps the handle 12 of the sheath for gastrostoma 1 with a hand.

With such a configuration in which the inner path 113 is closed with the lid 13, outflow of air supplied to the stomach from an endoscope can be prevented during surgery which will be described later. Also, of course, ingression of foreign objects, such as dust, into the sheath 1 can be avoided.

The hinge section 116 as an elastic support member which elastically supports the lid 13 at the closed position may, for example, have an arched configuration which functions as a plate spring in order to improve elasticity of the hinge section 116.

Alternatively, for example, an elastic member 14 may be provided separately from the hinge section 116 as an elastic support member which elastically supports the lid 13 to the closed position. The elastic member 14 is disposed outside of the base end of the sheath body 11 as illustrated in FIGS. 5A and 5B and applies an urging force to the handle 12 in a direction in which the handle 12 is moved toward the peripheral surface of the base end of the sheath body 11. In this case, the hinge section 116 does not have necessarily function as an elastic support member and it is sufficient that the hinge section 116 has a function to provide the handle 12 and the lid 13 pivotable with respect to the sheath body 11.

Note that the elastic member 14 may be configured in various manners. For example, an elastic member (e.g., a silicone rubber elastic member and a coil spring) may be used as a draw spring. Such an elastic member extends from the base end of the sheath body 11 radially outward of the sheath body 11 and is connected to the handle 12. Alternatively, the elastic member 14 may be a flat spring which is fixed to an outer surface of the base end and the handle 12 of the sheath body 11: to apply an urging force in a direction in which the handle 12 is moved toward the peripheral surface of the base end of the sheath body 11.

In a configuration illustrated in FIGS. 5A and 5B, the elastic member 14 is an elastic member made of silicone rubber. The elastic member 14 connects the base end of the sheath body 11 and an inclined piece 123 provided at an end of the handle 12 near the hinge section 116 (i.e., near a base end of the handle 12) to protrude toward the base end of the sheath body 11 in an inclined manner with respect to the plate-like handle 12. When the lid 13 is in its closed position, the inclined piece 123, as a part of the handle 12, is disposed close to the base end of the sheath body 11. When the lid 13 is moved to pivot from the closed position to an open direction, the inclined piece 123 is moved away from the base end of the sheath body 11 as the handle 12 pivots about the hinge section 116.

In this configuration, as the inclined piece 123 is moved to pivot about the hinge section 116 from its position (hereinafter, referred to as a re-approaching position) when the lid 13 is in its closed position and is separated from the re-approaching position, the elastic member 14 is subject to extension (i.e., stretching deformation or elastic deformation in an elongation direction). The extended elastic member 14 functions as a draw spring which applies an urging force to the handle 12 (in particular, to the inclined piece 123) to move back to the re-approaching position. This urging force functions as an elastic force for elastically supporting the lid 13 at the closed position.

In addition, in the invention, as described above, the hinge section 116 with a function to elastically support the lid 13 to the closed position is preferably employed to provide a configuration in which the lid 13 is closed by the elastic support member in a natural state in which no force is applied to the sheath for gastrostoma 1. Alternatively, however, a configuration may be employed in which a hinge section 116 with no function to elastically support the lid 13 at the closed position is provided and a state in which the inner path 113 is closed with the lid 13 can be implemented by an operation of the handle 12. In this case, while implementing the state in which the lid 13 closes the inner path 113 by the operation of the handle 12, pressure of air supplied to the stomach from the endoscope during surgery may keep the lid 13 from closing the inner path 113.

Since the lid 13 closes the inner path 113 of the sheath for gastrostoma 1, it prevents air supplied from an endoscope which is introduced orally into the stomach from leaking out of the stomach when a dilator is removed from a fistula expanded by the dilator 5 before a button for gastrostoma 2 is inserted.

In the state in which the lid 13 is closed, it is not necessary to provide airtightness for completely preventing outflow of air toward the base end from the distal section. It suffices to prevent leakage of air supplied to the stomach from an endoscope (hereinafter, referred to as air leakage) so as to avoid a narrowed endoscopic visual field. More preferably, the lid 13 is formed to completely prevent air leakage.

Figure 3B:
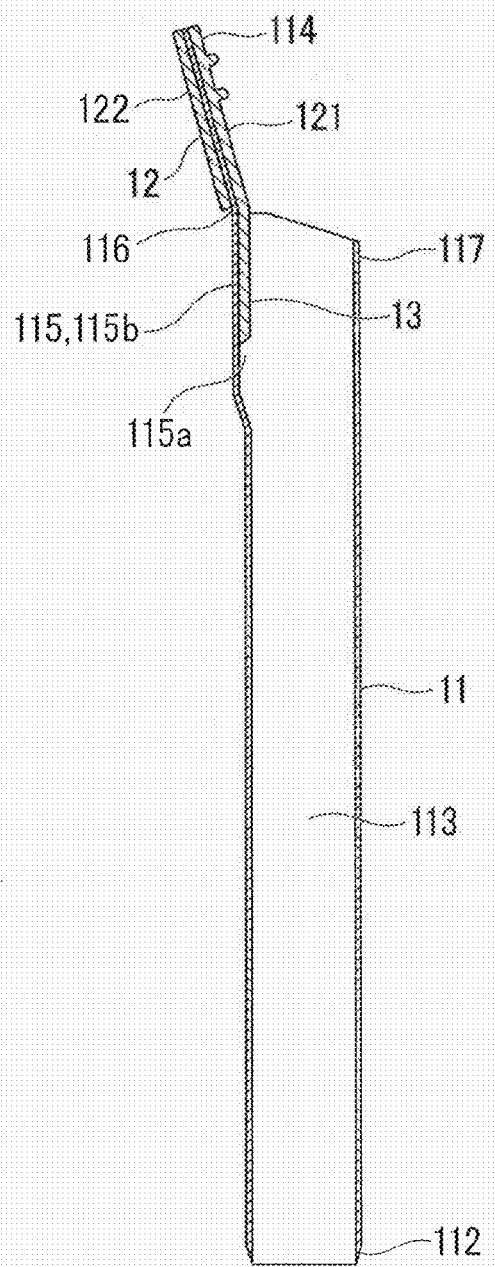
FIG. 3B is a left cross-sectional view of the sheath for gastrostoma according to the invention with the lid opened.

FIG. 3A is a perspective view and FIG. 3B is a cross-sectional view of the sheath for gastrostoma 1 illustrated with the lid 13 opened. Also, FIG. 4A is a top view, FIG. 4B is a front view, FIG. 4C is a right side view, FIG. 4D is a rear view and FIG. 4E is a bottom view of the sheath for gastrostoma according to the invention illustrated with the lid opened.

In the state in which the lid 13 is opened, it is necessary to prevent the inner path 113 from blocking a route along which the button for gastrostoma 2 and the dilator 5 are inserted. In order to receive the lid 13 pivoted from the closed position, it is preferable to provide a recess for receiving the lid inside the inner path 113. Such a recess may be implemented by, for example, an expanded section 115 provided in the sheath body 11. In the illustrated example, an inner space 115a of the expanded section 115 functions as a recess for receiving the lid 13 pivoted from the closed position. With this configuration, insertion resistance at the time of inserting the button for gastrostoma 2 and the dilator 5 in the sheath body 11 can be lowered.

FIGS. 6A to 6C and 7 illustrate an embodiment of the gastrostomy catheter 2 (hereinafter, also referred to as a button for gastrostoma) used together with the sheath for gastrostoma 1 according to the invention.

Figure 6A:
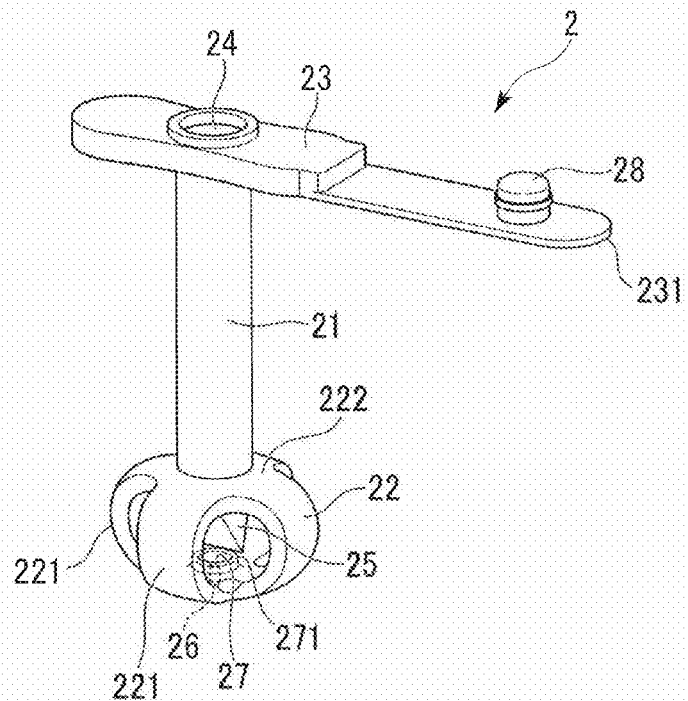
FIG. 6A is a perspective view of a button for gastrostoma used in the invention.
Figure 6B:
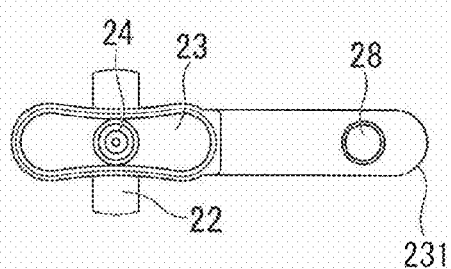
FIG. 6B is a top view of the button for gastrostoma used in the invention.
Figure 6C:
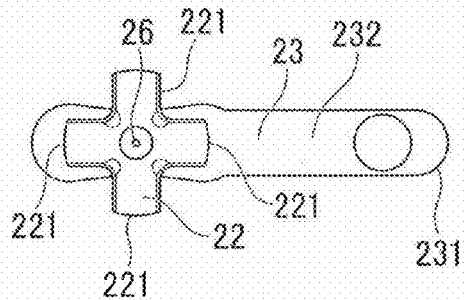
FIG. 6C is a bottom view of the button for gastrostoma used in the invention.
Figure 7:
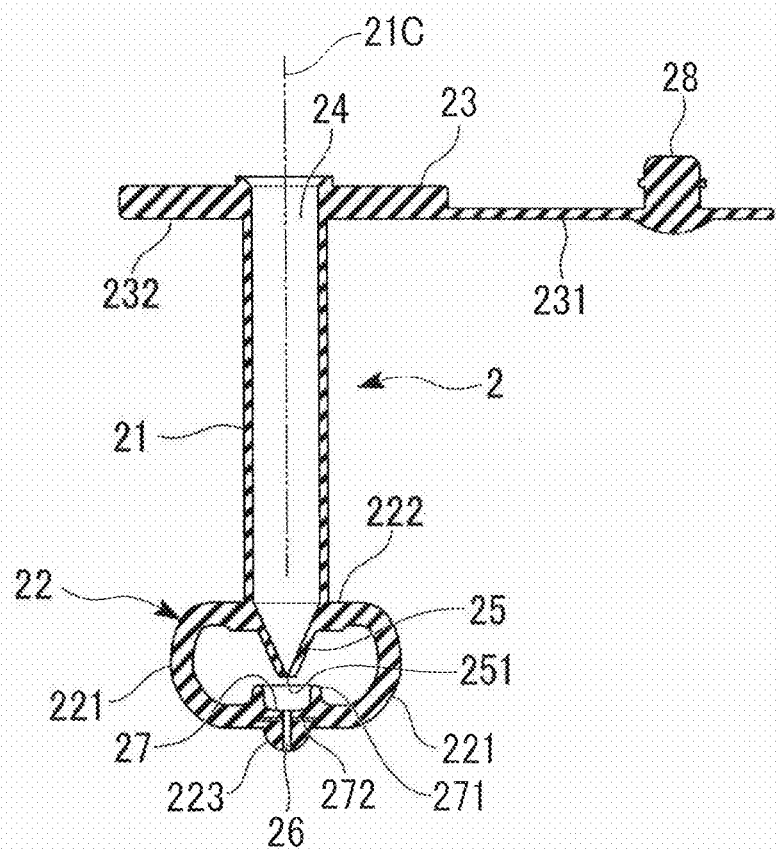
FIG. 7 is a cross-sectional view of a structure of the button for gastrostoma used in the invention.

FIG. 6A is a perspective view, FIG. 6B is a top view, FIG. 6C is a bottom view and FIG. 7 is a front cross-sectional view of the button for gastrostoma.

As illustrated in these drawings, the button for gastrostoma 2 includes a tubular section 21, an indwelling section 22 and an externally fixed section 23.

The indwelling section 22 is provided at one longitudinal end (hereinafter, referred to as a distal end) of the tubular section 21. The externally fixed section 23 is provided at the other longitudinal end (hereinafter, referred to as a base end) of the tubular section 21.

In more detail, a through-hole which penetrates inside the tubular section 21 functions as a path 24 for introducing a nutrient (i.e., a nutrient), chemical or other fluids. The externally fixed section 23 includes a cap 28 which closes the path 24 to shield the patient's body from outside when no nutrient or other fluid is introduced in the path 24. The cap 28 is provided at a distal end of a strip-shaped flexible piece 231 to extend from the externally fixed section 23 and is removably fit to an opening of the path 24 of the tubular section 21.

A valve 25 is provided at a distal section of the tubular section 21 to prevent back flow from the stomach.

The indwelling section 22 includes a plurality of (four in the illustrated example) elastically deformable strip-shaped pieces 221 disposed about a central axis 21C of the tubular section 21 (in particular, a portion on an extended line of the central axis 21C toward the distal end).

One longitudinal end of each of the strip-shaped pieces 221 extends from a base end gathering section 222 provided integrally with a distal end of the tubular section 21. The other longitudinal end of each of the strip-shaped pieces 221 is integrated at a distal end gathering section 223 (i.e., the most distal section of the indwelling section 222). The distal end gathering section 223 is spaced away from the base end gathering section 222 and along the central axis 21C of the tubular section 21 (in particular, a portion on an extended line of the central axis 21C toward the distal end). The entire indwelling section 22 is formed as a dome (i.e., as a round basket) constituted by the plurality of arcuate strip-shaped pieces 221 disposed between the base end gathering section 222 and the distal end gathering section 223.

The one longitudinal ends of the plurality of these strip-shaped pieces 221 extends radially from the base end gathering section 222 and the other longitudinal ends of the plurality of these strip-shaped pieces 221 extend radially from the distal end gathering section 223.

Also, the indwelling section 22 has the largest outer diameter in a middle portion between the base end gathering section 222 and the distal end gathering section 223.

Preferably, the button for gastrostoma 2 is integrally molded from synthetic resin.

The longitudinal direction ends of the plurality of these strip-shaped pieces 221 are gathered together at the base end gathering section 222 and the distal end gathering section 223 of the indwelling section 22.

FIGS. 8A to 8C illustrate an obturator 3 which is used to extend the protruding indwelling section 22 which has a diameter enlarged radially outward of the button for gastrostoma 2 so that the indwelling section 22 adopts a reduced-diameter state. FIG. 8A is a side cross-sectional view (left cross-sectional view of FIG. 8B), FIG. 8B is a front view and FIG. 8C is a side view (right side view of FIG. 3B) of the obturator 3.

Note that the obturator 3 will be described with an upper end being a base end and a lower end being a distal end in FIGS. 8A to 8C.

As illustrated in FIGS. 8A to 8C, the obturator 3 includes a pushing rod for extension 31, an outer case 32, a spring 312 and a stopper 33.

The pushing rod for extension 31 consists of an operating section 311, a rod body 313 and a lock piece 316. A reference numeral 317 denotes a distal section of the rod body 313 and a reference numeral 314 denotes a reinforcing member attached to the distal section 317 of the rod body 313. Also, a reference numeral 315 denotes a wire insertion groove (i.e., a guidewire path) formed along the longitudinal direction of the rod body 313.

The operating section 311 is fixedly attached to the rod body 313.

The outer case 32 includes a cylindrical portion 321, a finger plate 322, a fitting portion 323, a groove 324, a groove hole 325 and a lock hole 326. The finger plate 322, the fitting portion 323, the groove 324, the groove hole 325 and the lock hole 326 are provided in the cylindrical portion 321.

The spring 312 urges the pushing rod for extension 31 in a direction in which an amount of protrusion of the distal end distal end (in particular, the distal end of the rod body 313) of the pushing rod for extension 31 from a distal end of the outer case 32 is decreased. In particular, the spring 312 is a coil spring which is placed over the rod body 313.

The rod body 313 of the pushing rod for extension 31 is disposed inside the cylindrical portion 321 of the outer case 32 so as to be slidable in the longitudinal direction of the outer case 32. The pushing rod for extension 31 can be moved in the longitudinal direction thereof with respect to the outer case 32.

In this obturator 3, when an operator pushes the operating section 311 of the rod body 313 in a direction in which the operating section 311 is pushed into the outer case 32, the pushing rod for extension 31 is moved along the longitudinal direction of the outer case 32 to increase an amount of protrusion of the distal end of the rod body 313 from the distal end of the outer case 32. The operating section 311 the pushing rod for extension 31 fixed to a portion (a base end: also functions as a base end of the pushing rod for extension 31) protruding from one longitudinal end (base end) of the outer case 32 of the rod body 313 is moved along the longitudinal direction of the outer case 32. Thus, an amount of protrusion of the distal end of the rod body 313 from the distal end of the outer case 32 increases. Note that in the illustrated example, the distal section 317 of the rod body 313 protrudes from the distal end of the outer case 32 before the operating section 311 is pushed in (i.e., an initial state). The distal end 317, however, does not necessarily protrude from the distal end of the outer case 32.

In accordance with moving of the pushing rod for extension 31 with respect to the outer case 32 by pushing the operating section 311, the lock piece 316 of the pushing rod for extension 31 moves from the groove 324 of the outer case 32, passes through the inside of the outer case 32 and engages with the lock hole 326 of the outer case 32. In this manner, movement of the pushing rod for extension 31 with respect to the outer case 32 can be prevented (this locked state will be referred to as a protruded state hereinafter). The lock piece 316 is urged by the urging force of the spring incorporated in the rod body 313. The lock piece 316 is provided to protrude from a side surface of the rod body 313 and is able to be pushed into the rod body 313.

In the protruded state, the amount of protrusion of the distal end of the pushing rod for extension 31 (i.e., the distal end of the rod body 313) from the distal end of outer case 32 is maintained. When the lock piece 316 is pushed and disengaged from the lock hole 326 of the outer case 32 in this protruded state, the pushing rod for extension 31 moves with respect to the outer case 32 due to the urging force of the spring 312 and the lock piece 316 moves to the groove 324 from the lock hole 326 of the outer case 32 to return to the initial state. The initial state is a state in which the amount of protrusion of the distal end of the rod body 313 from the distal end of the outer case 32 is smaller (including a state in which the distal end of the rod body 313 does not protrude at all) as compared with the protruded state.

The spring 312 is provided in the pushing rod for extension 31 to enable a switchover from the protruded state to the initial state only through pushing in of the lock piece 316.

In the illustrated example, although the spring 312 is a coil spring which is disposed over the rod body 313 at the base end thereof and located between the operating section 311 and the base end of the outer case 32, arrangements and configurations of the spring 312 for enabling a switchover from the protruded state to the initial state only through pushing in of the lock piece 316 are not limited to those in the illustrated example.

As illustrated in FIGS. 10A and 10B, the obturator 3 is first made to engage with the button for gastrostoma 2 in the initial state and then adopt the protruded state. In this protruded state, the distal section 317 of the rod body 313 presses the rod abutting section 27 (see FIG. 7) provided in the button for gastrostoma 2 at an inner side of the indwelling section 22 of the distal end gathering section 223 so as to move the rod abutting section 27 away from the base end gathering section 222. As illustrated in FIG. 7, the rod abutting section 27 is a wall (i.e., a rod abutting wall) formed integrally with the distal end gathering section 223 at a position opposite to the base end gathering section 222 at the inside of the indwelling section 22 of the distal end gathering section 223. In particular, in FIG. 7, the rod abutting section 27 is formed by thickening a portion opposite to the base end gathering section 222 at the inside of the indwelling section 22 of the distal end gathering section 223 and is continuous to and integral with the distal end gathering section 223.

Accordingly, when the obturator 3 engaging with the button for gastrostoma 2 (i.e., the obturator 3 at its initial state) adopts the protruded state, the distal end gathering section 223 and the rod abutting section 27 are moved away from the base end gathering section 222. As a result, the indwelling section 22 of the button for gastrostoma 2 is extended to adopt a reduced-diameter state.

The pushing rod for extension 31 functions as a member which is inserted in the indwelling section 22 of the gastrostomy catheter 2 so as to press rod abutting section 27 of the indwelling section 22, thereby extending the indwelling section 22.

The rod abutting wall 27 functions also as a reinforcing wall which reinforces the distal end gathering section 223.

As illustrated in FIG. 7, the rod abutting section 27 is reinforced by the reinforcing member 272. It is preferable that, when the obturator 3 applies the extending force to the extracorporeal section 22, the indwelling section 22 can be introduced in the patient's body easily and reliably in its reduced-diameter state without a risk of the distal section 317 of the rod body 313 of the obturator 3 breaking through the distal end gathering section 223. Reinforcement by the reinforcing member 272 is preferred also in respect of keeping a configuration of a communication path 26 (described later) which is a small bore formed through the rod abutting section 27 and the distal end gathering section 223.

The reinforcing member 272 may be formed of, for example, metal, reinforced fiber and reinforced plastic and may preferably have a mesh structure. The reinforcing member 272 is provided integrally with the rod abutting section 27 by, for example, embedding into the rod abutting section 27 as illustrated to FIG. 7, or fixing (e.g., adhesion fixing) to a surface of the rod abutting section 27 (i.e., a surface facing the distal end of the tubular section 21 of the button for gastrostoma 2).

A meshed reinforcing member 272 is easily extendable. An easily extendable configuration of the reinforcing member 272 is preferable also in respect of reducing the diameter of the indwelling section 22.

Note that the communication path 26 is formed at the distal section of the indwelling section 22 of the button for gastrostoma 2. The communication path 26 is a bore which penetrates the rod abutting section 27 and the distal end gathering section 223 for drawing a guidewire 4 into the button for gastrostoma 2 from the distal section of the indwelling section 22. The communication path 26 is formed to penetrate the rod abutting section 27 and the distal end gathering section 223 on the central axis 21C of the tubular section 21 (in particular, a portion on an extended line of the central axis 21C toward the distal end).

In addition, a reference numeral 271 in FIG. 7 denotes a rod fitting projection provided to protrude annularly around an outer periphery of the rod abutting section 27. This rod fitting projection 271 is formed as a ring which surrounds an opening of the communication path 26 in the rod abutting section 27 coaxially with the central axis 21C (in particular, a portion on an extended line of the central axis 21C toward the distal end) of the tubular section 21 of the button for gastrostoma 2. As illustrated in FIG. 10A, when the obturator 3 is made to fit onto the button for gastrostoma 2, obturator 3, the distal section 317 of the rod body 313 of the obturator 3 is inserted in and fit into the inside of the rod fitting projection 271. Thus, the rod body 313 of the obturator 3 is aligned with the rod abutting section 27, that is, aligned coaxially with the communication path 26.

When the obturator 3 is made to fit to the button for gastrostoma 2, in particular, the obturator 3 is inserted in the path 24 of the tubular section 21 of the button for gastrostoma 2 from the side of the externally fixed section 23 and then fit to the button for gastrostoma 2.

The obturator 3 is inserted in the tubular section 21 from the distal end thereof. When the obturator 3 is fit to the button for gastrostoma 2, the peripheral surface of the outer case 32 is made to contact the inner surface of the path 24 of the tubular section 21 so that the obturator 3 is aligned with the button for gastrostoma 2 without any backlash. The distal section of the rod body 313 protruding from the distal end of the outer case 32 is inserted into the indwelling section 22 via the valve 25 (see FIG. 7) provided at an indwelling section 22 side end of the tubular section 21 and is made to abut or be disposed near the rod abutting section 27 of the indwelling section 22.

The valve 25 is made of synthetic resin and is formed in an elastically deformable umbrella shape which closes an end opening of the tubular section 21 at the side of the indwelling section 22. The valve 25 includes a slit 251 formed at the top thereof. The distal end of the rod body 313 is pushed into the indwelling section 22 from the path 24 of the tubular section 21 so as to penetrate the slit 251 and is disposed coaxially with the central axis 21C (see FIG. 7) of the tubular section 21 of the button for gastrostoma 2. Thus, in the protruded state, the distal end of the rod body 313 can press the rod abutting section 27 to extend the indwelling section 22.

As illustrated in FIG. 8B, a reinforcing member 314 is attached to the distal section 317 of the rod body 313 of the obturator 3 which is subject to a large load at the time of extension of the button for gastrostoma. In the illustrated example, the reinforcing member 314 is a thin reinforcement sleeve.

Figure 11:
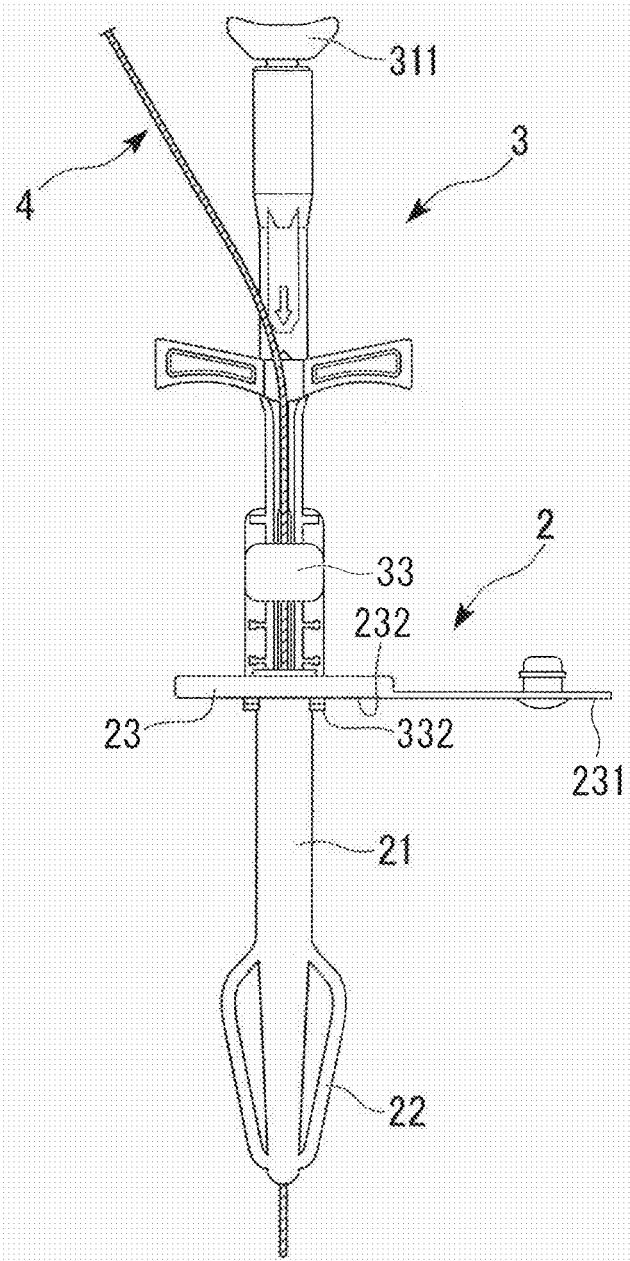
FIG. 11 is a front view illustrating a state in which the button for gastrostoma and the obturator used in the invention are assembled together and the button for gastrostoma is extended using a guidewire.

As illustrated in FIG. 11, a wire insertion groove 315 (see FIGS. 8A, 9A and 9B) of the rod body 313 is formed along the longitudinal direction of the rod body 313 toward the base end of the rod body 313 from the distal end of the rod body 313. The guidewire 4 can be inserted in this wire insertion groove 315 from the opening at the distal end of the rod body 313.

Moreover, the wire insertion groove 315 is always visible from the outside of the outer case 32 via a groove hole 325 provided in the outer case 32 either when the obturator 3 is extended or when the obturator 3 is retracted. The groove hole 325 of the outer case 32 is an outlet of the guidewire 4 inserted in the wire insertion groove 315 from the button for gastrostoma 2.

A finger plate 322 is provided to protrude from the outer case 32. An operator can hold the obturator 3 easily with his or her fingers with the finger plate 322.

Moreover, a fitting portion 323 for fixedly fitting the stopper 33 which will be described later is provided on an outer periphery of the outer case 32.

The stopper 33 can function as an anchoring member for anchoring the button for gastrostoma 2 with respect to the obturator 3.

The fitting portion 323 of the obturator 3 is a plurality of (three or more) projections provided at constant intervals provided along the longitudinal direction of the outer case 32 at both sides of the outer case 32 of the obturator 3. A pair of arms 331 are provided at the stopper 33 which removably engages with a fit-in groove 323a provided between the adjacent fitting portions 323.

Figure 9A:
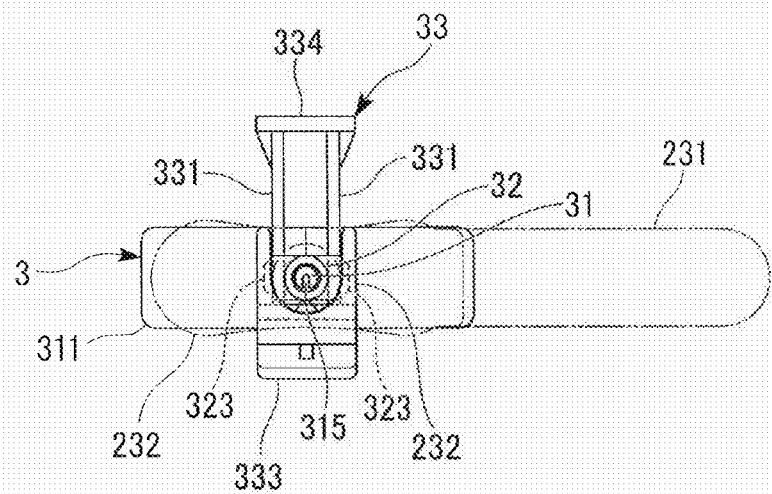
FIG. 9A illustrates a relationship between the obturator used in the invention and the stopper attached to obturator, illustrated in a state in which the stopper can engage with an externally fixed section of a button for gastrostoma.
Figure 9B:
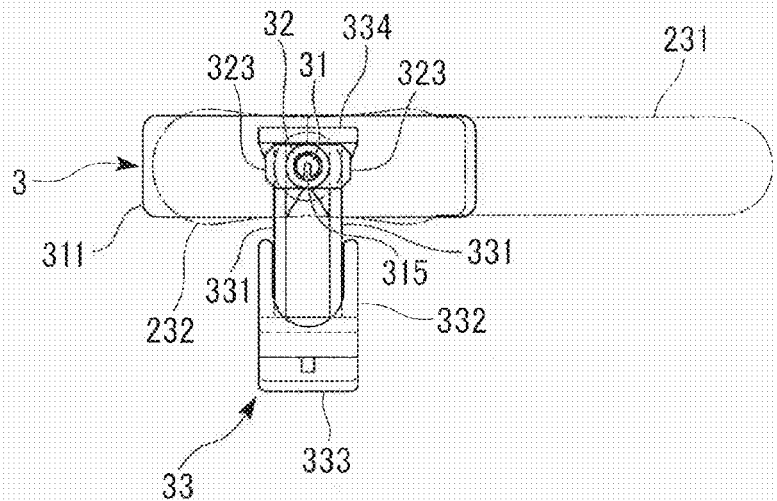
FIG. 9B illustrates a relationship between the obturator used in the invention and the stopper attached to the obturator, with the stopper being in its disengaged state.

As illustrated in FIGS. 9A and 9B or other drawings, the stopper 33 is formed as a square frame which includes a back plate 333, a plate-like pushed-in portion 334 and a pair of rod-shaped arms 331. The stopper 33 is placed over the outer case 32 of the obturator 3. The arms 331 have a function to connect the back plate 333 and the pushed-in portion 334 disposed opposite to each other across the obturator 3 inserted in an inner space of the square frame-shaped stopper 33.

A mounting position of the stopper 33 with respect to the obturator 3 is determined by the arms 331 fit to any of the fit-in groove 323a selected among the plurality of the fit-in grooves 323a. Also, the mounting position of the stopper 33 with respect to the obturator 3 can be changed by changing the fit-in groove 323a to which the arms 331 are made to fit.

The arms 331 which have been fitted to the fit-in groove 323a can be removed from the fit-in groove 323a by rotating the stopper 3 with respect to the obturator 3 in the direction of the axis of the outer case 32. As illustrated in FIGS. 9A, 9B and other drawings, there are provided areas where no fitting portion 323 is provided (i.e., non-fitting areas) at 90 degrees apart from areas where the fitting portions 323 are provided (i.e., fitting areas) about the axial direction of the outer case 32 on the outer periphery of the outer case 32 of the obturator 3. The stopper 3 can be switched between a state in which it engages with the obturator 3 and a state in which it disengages from the obturator 3 due to axial rotation of the outer case 32. The distance between the back plate 333 and the pushed-in portion 334 of the stopper 33 is larger than that between a pair of arms 331. Accordingly, when the arms 331 are in the non-fitting areas, the stopper 3 can be slidingly moved along the longitudinal direction of the outer case 32 without interference of the back plate 333 and the pushed-in portion 334 with the fitting portion 323. In this manner, the fit-in groove 323a to which the arms 331 are to be fit can be selected or changed.

In addition, the arms 331 engaging with the fit-in groove 323a of the obturator 3 can be slidingly moved along the longitudinal direction of the arms 331 with respect to the obturator 3 while being disposed inside the fit-in groove 323a. That is, the obturator 3 can be slidingly moved along the longitudinal direction of the arms 331 with respect to the stopper 33 attached to the obturator 3 with the arms 331 engaging with the fit-in groove 323a functioning as a guide.

The back plate 333 and the pushed-in portion 334 can be used as an operating piece which provides easy operation to cause the stopper 33 attached to the obturator 3 to slidingly move with respect to the obturator 3 (i.e., slidingly move in a direction perpendicular to the longitudinal direction of the obturator 3).

With this sliding movement, the stopper 33 can make a holding section 332 provided to protrude from the back plate 333 engage and disengage with respect to the externally fixed section 23 of the button for gastrostoma 2 engaging with the obturator 3.

The holding section 332 is a hook-shaped piece protruding from a surface on which the arms 331 of the back plate 333 are provided to protrude at a position separated from the arms 331 on the back plate 333. As illustrated in FIGS. 10A, 10B and 11, when the stopper 33 attached to the obturator 3 is slidingly moved with respect to the obturator 3 (i.e., slidingly moved in a direction perpendicular to the longitudinal direction of the obturator 3), the holding section 332 is inserted in and removed from the patient contact surface 232 side of the externally fixed section 23 of the button for gastrostoma 2 with which the obturator 3 is engaged and is thus engaged or disengaged with respect to the externally fixed section 23.

In a state in which the pushed-in portion 334 of the stopper 33 abuts the outer case 32 of the obturator 3, the holding section 332 is separated from the externally fixed section 23 of the button for gastrostoma 2 with which the obturator 3 is engaged and thus does not anchor the button for gastrostoma 2 (i.e., a disengaged state as illustrated in FIG. 9B). In this disengaged state, the button for gastrostoma 2 can be slidingly moved freely along the longitudinal direction of the outer case 32 of the obturator 3.

From this disengaged state, when the stopper is slidingly moved with respect to the obturator 3 so that the back plate 333 is moved close to the obturator 3, the holding section 332 is inserted in the patient contact surface 232 side of the externally fixed section 23 and engages with the externally fixed section 23 (a state illustrated in FIG. 9A). The holding section 332 contacts the patient contact surface 232 and engages with the externally fixed section 23. Thus, the holding section 332 anchors the button for gastrostoma 2 so as not to move toward the distal end of the obturator 3. In this manner, when the obturator 3 engaging with the button for gastrostoma 2 adopts the protruded state from the initial state, the extending force from the pushing rod for extension 31 (in detail rod body 313) can be reliably transmitted to the indwelling section 22 while reliably keeping the indwelling section 22 in its extended state, i.e., the reduced-diameter state.

The obturator 3 can be assembled to the button for gastrostoma 2 in the following manner. As illustrated in FIG. 10A, the outer case 32 of the obturator 3 (in its initial state) is inserted in the path 24 of the button for gastrostoma 2 for engagement and the back plate 333 of the stopper 33 is pushed in the direction of the pushed-in portion 334. Thus, a body surface fixing portion 23 of the button for gastrostoma 2 is held (anchored) by the holding section 332 of the stopper 33. When the outer case 32 of the obturator 3 is inserted in the path 24 of the button for gastrostoma 2, the back plate 333 of the stopper 33 is moved away from the outer case 32 and is made to adopt the disengaged state so that the back plate 333 does not interfere with the externally fixed section 22 of the button for gastrostoma 2.

In this assembled state, as illustrated in FIG. 10B, the operating section 311 of the pushing rod for extension 31 is operated to cause the obturator 3 to adopt its protruded state and the indwelling section 22 of the button for gastrostoma 2 is extended.

Also, after the obturator 3 adopts the state of FIG. 10A, a guidewire 4 is inserted through the pushing rod for extension 31 of the obturator 3 before the obturator 3 adopts the protruded state as illustrated in FIG. 11. The guidewire 4 is inserted through the pushing rod for extension 31 of the obturator 3 (i.e., through a wire insertion groove 315 of the rod body 313) via the rod abutting section 27 of the indwelling section 22 of the gastrostomy catheter 2 and the communication path 26 (see FIG. 7) penetrating the distal end gathering section 223. The guidewire 4 is pulled out from a groove hole 325 of the outer case 32 in advance.

When the obturator 3 is made to engage with the button for gastrostoma 2, an opening of the wire insertion groove 315 provided at a distal end of the pushing rod for extension 31 of the obturator 3, the rod abutting section 27 of the indwelling section 22 of the gastrostomy catheter 2 and the communication path 26 penetrating the distal end gathering section 223 are positioned to communicate with one another. Thus, in the set-up state, the guidewire 4 can be inserted easily in the pushing rod for extension 31.

Figure 12A:
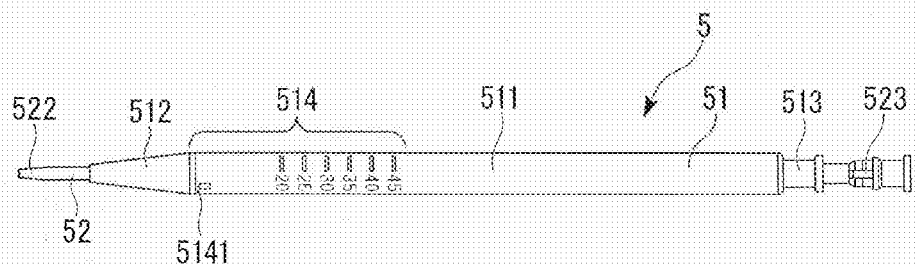
FIG. 12A is a front view of a dilator used in the invention.
Figure 12B:
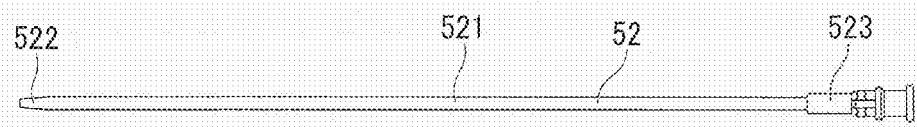
FIG. 12B is a front view of a narrow-diameter dilator used in the invention.
Figure 12C:
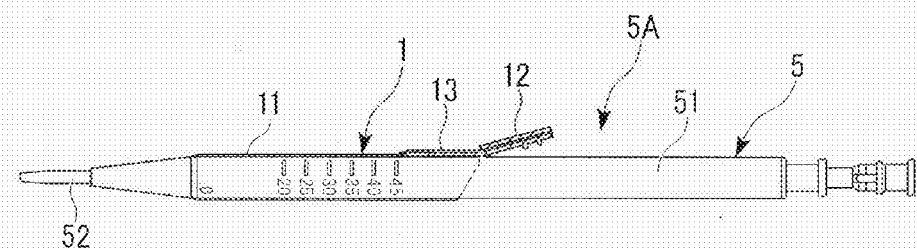
FIG. 12C is a front view of a sheathed dilator in which the sheath for gastrostoma according to the invention is combined with a dilator.
Figure 12D:
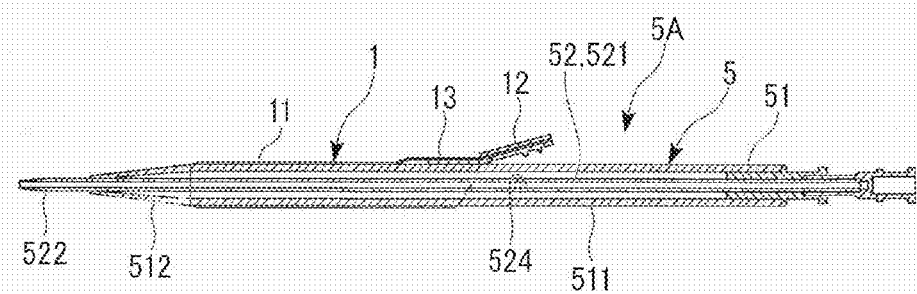
FIG. 12D is a cross-sectional view of a sheathed dilator in which the sheath for gastrostoma according to the invention is combined with a dilator.

FIGS. 12A to 12D illustrate an exemplary dilator (extender) 5 for forming a fistula, FIG. 12A is a front view and FIG. 12B is a front view of a narrow-diameter dilator 52 which constitutes the dilator. FIG. 12C is a front view illustrating a state in which a dilator 5 is covered with the sheath for gastrostoma 1 (i.e., a sheathed dilator 5A) with the sheath for gastrostoma 1 being illustrated as a cross-sectional view. FIG. 12D is a cross-sectional view of a dilator 5 covered with the sheath for gastrostoma 1 (i.e., a sheathed dilator 5A).

Note, in FIGS. 12A to 12D, that a left side of the paper is defined as a distal end side and a right side of the paper is defined as a rear end side.

As illustrated in FIGS. 12A to 12D, the dilator 5 has a narrow-diameter dilator 52 (see FIG. 10) and a large-diameter dilator 51 which are integrated with each other (i.e., an integrated dilator). The large-diameter dilator 51 is a cylindrical body disposed over the narrow-diameter dilator 52 and is assembled to the narrow-diameter dilator 52.

The narrow-diameter dilator 52 is a rod-shaped member which includes a tapered distal section 522 (i.e., a narrow-diameter dilator distal section 522) at the distal end thereof. The narrow-diameter dilator 52 also includes a guidewire path 524 penetrating the same in the longitudinal direction.

The large-diameter dilator 51 includes a cylindrical large-diameter dilator body section 511 and a tapered large-diameter dilator distal section 512 provided to protrude from a distal end of the large-diameter dilator body section 511. The narrow-diameter dilator distal section 522 of the narrow-diameter dilator 52 protrudes from the large-diameter dilator distal section 512.

Also, connectors 513 and 523 are provided in each of the rear ends of the dilators 51 and 52. The connectors 513 and 523 fit each other with luer taper fitting. The narrow-diameter dilator 52 is integrally assembled to the large-diameter dilator 51 through fitting of the connectors 513 and 523.

As illustrated in FIG. 12A, a scale 514 is provided on a peripheral surface of the large-diameter dilator body section 511. A reference point (zero point) 5141 is provided at the large-diameter dilator distal section 512 side. The scale is used to measure the distance from the patient's body surface to an inner stomach wall. After the dilator 5 is inserted, an operator positions the reference point 5141 at the inner stomach wall and reads the scale at the side of the patient's body surface under the endoscope. With this measurement, the length of the tubular section 21 of the button for gastrostoma 2 can be selected.

FIG. 12C illustrates a state in which the dilator 5 is covered with the sheath for gastrostoma 1 to provide a sheathed dilator 5A.

The sheath for gastrostoma 1 is disposed with the distal section thereof positioned at a distal end of the large-diameter dilator body section 511. Although the sheath for gastrostoma 1 includes no means for positioning itself with respect to the dilator 5, the dilator 5 may include a movement restriction means (e.g., a projection which the base end of the sheath body 11 of the sheath for gastrostoma 1 abuts) which restricts sliding movement of the sheath for gastrostoma 1 toward the rear end thereof.

In addition, a tapered portion 112 (see FIG. 3B) is preferably provided at the distal section of the sheath for gastrostoma 1 so as to eliminate level difference between the sheath for gastrostoma 1 and the large-diameter dilator body section 511. With the tapered portion 112, it becomes possible to lower insertion resistance at the time of inserting the dilator 5 with the sheath for gastrostoma 1 disposed thereon (sheathed dilator 5A) in an abdominal wall and a stomach wall. The tapered portion 112 can be provided by, for example, tube extension or heat molding. Misalignment of the sheath for gastrostoma 1 with respect to the body section 511 of the dilator 5 can be restricted by adjusting the inner diameter of the sheath body 11 so that the inner diameter is pressed against an outer diameter of the large-diameter dilator body section 511.

Figure 13:
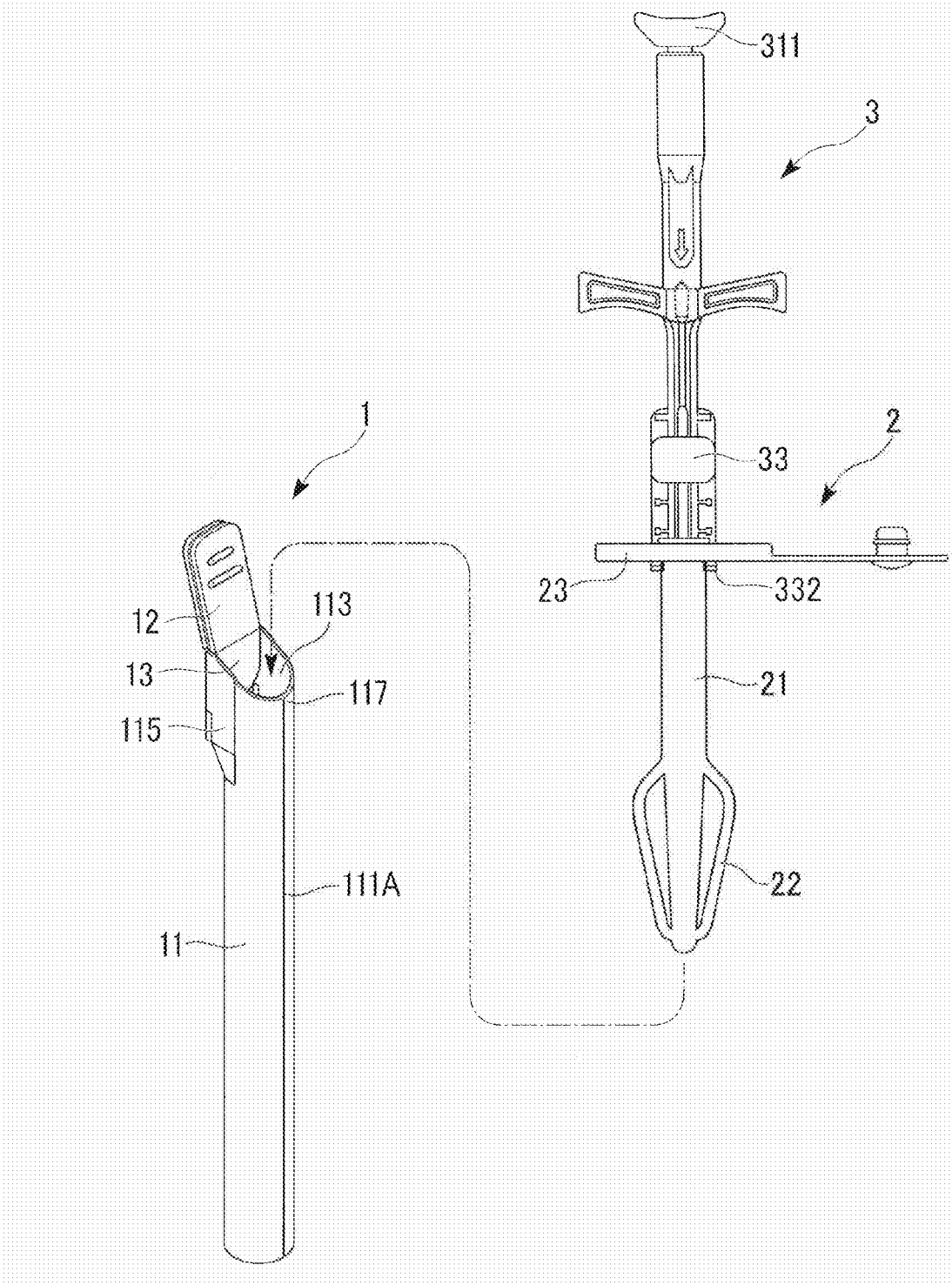
FIG. 13 is a front view illustrating a state immediately before the button for gastrostoma extended with the obturator is disposed in the sheath for gastrostoma according to the invention.

FIG. 13 illustrates a state before the button for gastrostoma 2 is inserted in the inner path 113 of the sheath for gastrostoma 1. At this time, the indwelling section 22 of the button for gastrostoma 2 has been extended to have a reduced diameter by the obturator 3.

The inner diameter of the sheath body 11 of the sheath for gastrostoma 1 preferably corresponds to the outer diameter of the tubular section 21 of the button for gastrostoma 2.

However, the indwelling section 22 of the button for gastrostoma 2 which will be left in the patient's body has the maximum outer diameter larger than the outer diameter of the tubular section 21 in the initial state before its diameter is reduced and thus protrudes significantly from the tubular section 21 in a radially outward direction. Accordingly, it is often a significant technical challenge to reduce the diameter of the greatly protruding indwelling section 22 to the outer diameter of the tubular section.

On the other hand, it is preferred that the inner path 113 of a diameter of the sheath for gastrostoma 1 be substantially equivalent to the maximum outer diameter of the dilator 5. The maximum outer diameter of the dilator 5, i.e., the outer diameter of the large-diameter dilator body section 511, determines the size of the fistula to be formed. It is preferred that the size of the fistula be almost equivalent to the outer diameter of the tubular section 21 of the button for gastrostoma 2 or larger by not less than 1 to 2 mm.

A configuration has been considered for efficiently placing the indwelling section 22 by lowering resistance when the indwelling section 22 is inserted in and made to pass through the fistula of the indwelling section 22 using the sheath 1 even if the maximum outer diameter of the extended indwelling section 22 is larger than the diameter of the inner path 113 of the sheath for gastrostoma 1. In this case, since the diameter of the sheath body 11 of the sheath 1 can be made smaller than the maximum outer diameter of the extended indwelling section 22, the size of the fistula may also be decreased.

In this configuration, since the inner diameter of the inner path 113 of the sheath for gastrostoma 1 is made smaller than the maximum outer diameter of the extended indwelling section 22, the sheath body 11 splits when a portion of the indwelling section 22 of the button for gastrostoma 2 at which outer diameter is larger than the diameter of the inner path 113 tries to pass through the inner path 113. It is preferred that the diameter of the inner path 113 of the sheath for gastrostoma 1 be larger than the outer diameter of the most distal section of the indwelling section 22.

Figure 14:
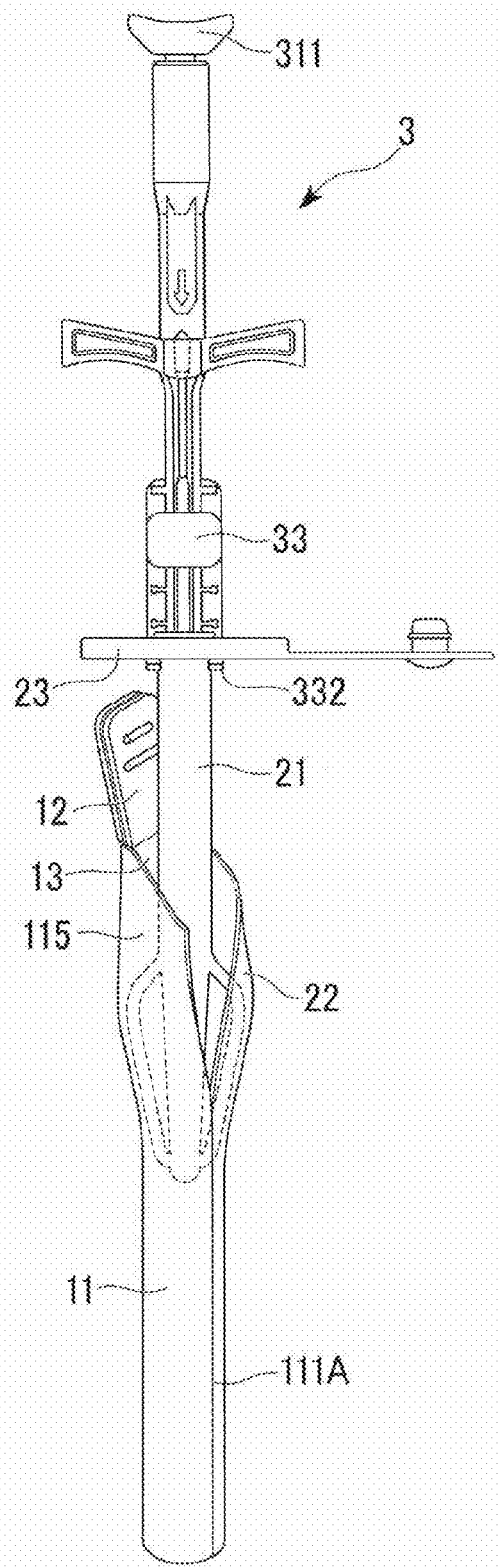
FIG. 14 is a front view illustrating a state in which the button for gastrostoma extended with the obturator is being disposed in the sheath for gastrostoma according to the invention.

FIGS. 13 and 14 illustrate the sheath for gastrostoma 1 configured to have dimensions described above. These drawings illustrate a state in which the button for gastrostoma 2 is inserted in the sheath for gastrostoma 1. The sheath for gastrostoma 1 is configured such that the sheath body 2 can vertically split when a portion of the indwelling section 22 of the button for gastrostoma 2 which is made to adopt an extended state (reduced-diameter state) by the obturator 3 where the outer diameter is larger than the diameter of the inner path 113 tries to pass through the inner path 113. The button for gastro stoma 2 inserted in the sheath body 11 of the sheath for gastrostoma 1 has the maximum outer diameter in the reduced-diameter state of the indwelling section 22 which is larger than the diameter of the inner path 113 of the sheath for gastrostoma 1.

Since the outer diameter of the most distal section (i.e., the distal end gathering section 223) of the indwelling section 22 is smaller than the diameter of the inner path 113 of the sheath for gastrostoma 1, the most distal section can be easily inserted and made to pass through the inner path 113. However, the sheath body 11 splits when the portion of the indwelling section 22 of the button for gastrostoma 2 having the outer diameter larger than the diameter of the inner path 113 tries to pass through the inner path 113.

Also in the case illustrated in FIG. 14, insertion resistance can be lowered because an inner cavity through which the most distal section of the indwelling section 22 passes is formed of the inner path 113 of the sheath for gastrostoma 1.

Materials for constituting the sheath body 11 are not particularly limited, but preferably include polyethylene resin, polypropylene resin, polytetrafluoroethylene resin (PTFE), tetrafluoroethylene hexafluoropropylene copolymer (FEP) and tetrafluoroethylene ethylene copolymer (ETFE). Among these, fluoro-resin having low frictional resistance is preferably used as the material to constitute the sheath body 11. It is therefore possible to lower frictional resistance of the button for gastrostoma 2 and the inner path 113 when the button for gastrostoma 2 is inserted and made to pass through the inner path 113, thereby lowering insertion resistance of the button for gastrostoma 2.

Examples of configurations for making the sheath body 11 split when the portion of the indwelling section 22 having the outer diameter larger than the diameter of the inner path 113 of the sheath for gastrostoma 1 is inserted include, but are not limited to: a configuration in which a PTFE tube is used as the sheath body 11 which has an orientation in the longitudinal direction that can split vertically; a configuration which has a sheath body 11 which is locally thinned by a cut-out groove (i.e., a notch section) extending along the longitudinal direction of the sheath body 11; and a configuration in which a cut portion is formed in advance in the sheath body 11 by a slit (i.e., notch section) extending along the longitudinal direction of the sheath body 11. When notch sections, such as a cut-out groove and a slit, are formed in the sheath body 11, the sheath body 11 splits along the entire length along the portion where the notch section is formed when the indwelling section 22 is inserted.

In particular, FIGS. 1A, 1B, 4A to 4E, 13 and 14 illustrate a configuration in which a notched groove 111A is formed in the sheath body 11 as a notch section.

Figure 16A:
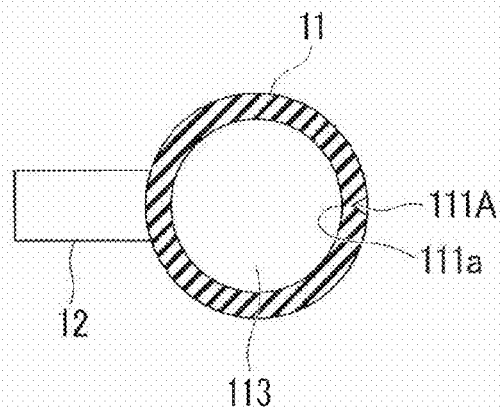
FIG. 16A schematically illustrates a cross-sectional structure and a position of a handle of the sheath body of the sheath for gastrostoma according to the invention, with a notched groove formed in the sheath body as a notch section.

As illustrated in FIG. 16A, the notched groove 111A is formed in the sheath body 11 so as not to penetrate the sheath body 11 in the thickness direction. The sheath body 11 includes an uncut portion 111a formed by locally reducing the thickness of the sheath body 11 at a groove bottom side of the notched groove 111A.

The uncut portion 111a fractures when the portion of the indwelling section 22 in its reduced-diameter state having the outer diameter larger than the diameter of the inner path 113 of the sheath for gastrostoma 1 is inserted in the sheath body 11.

As a result of the fracture of the uncut portion 111a, the sheath body 11 splits vertically.

Figure 15A:
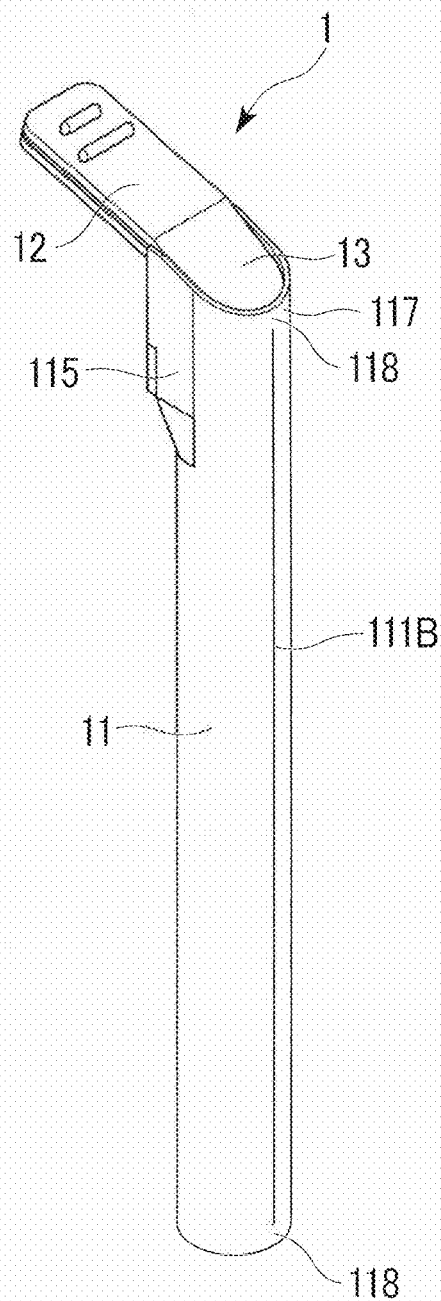
FIG. 15A is a perspective view of a configuration in which a slit is formed as a notch section in the sheath body of the sheath for gastrostoma according to the invention, with the lid being in its closed position.
Figure 15B:
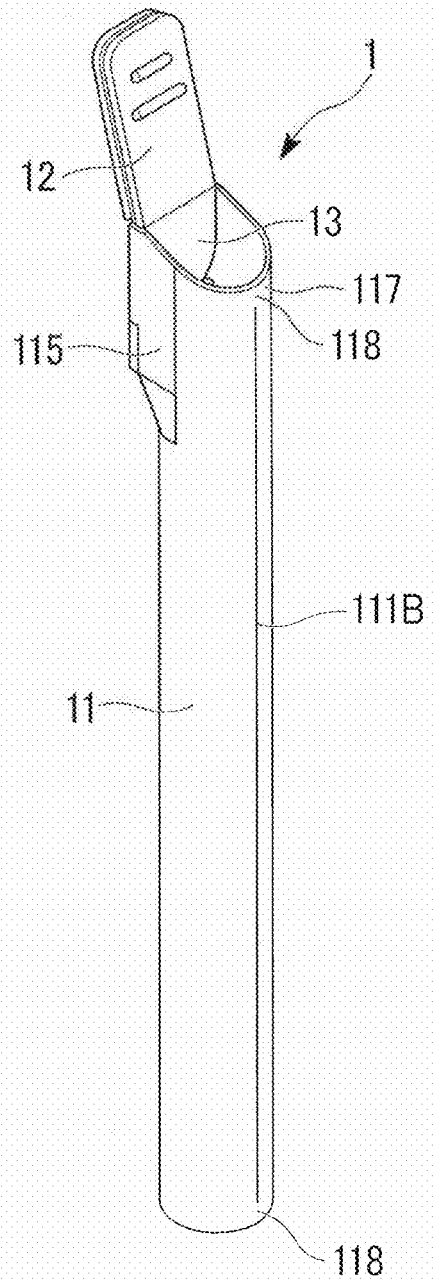
FIG. 15B is a perspective view of a configuration in which a slit is formed as a notch section in the sheath body of the sheath for gastrostoma according to the invention, with the lid moved away from the closed position to release the inner path of the sheath body.

In contrast, FIGS. 15A and 15B illustrate a configuration in which a slit 111B is formed in the sheath body 11 as a notch section.

In the configuration in which the slit 111B is formed, the slit 111B is formed at a portion along the longitudinal direction of the sheath body 11. An uncut portion 118 is provided on a virtual extended line of the slit 111B where no slit 111B is formed. The uncut portion 118 keeps the form of the sheath body 11 until the button for gastrostoma 2 is inserted in the sheath body 11 (in particular, until the portion of the indwelling section 22 having the outer diameter larger than the diameter of the inner path 113 of the sheath for gastrostoma 1 is inserted in the sheath body 11). In FIGS. 15A and 15B, the slit 111B is not formed at both the longitudinal ends of the sheath body 11 and the uncut portions 118 are provided at both the longitudinal ends of the sheath body 11.

The uncut portion 118 fractures when the portion of the indwelling section 22 in its reduced-diameter state having the outer diameter larger than the diameter of the inner path 113 of the sheath for gastro stoma 1 is inserted in the sheath body 11, or alternatively, when the portion presses and deforms the portion of the sheath body 11 where the slit 111B is formed from the side of the inner path 113 so that the uncut portion 118 fractures from the slit 111B. Fracture of the uncut portion 118 results in vertical splitting of the sheath body 11.

The uncut portion 118 is not necessarily formed at both longitudinal ends of the sheath body 11, but may be formed at one of the longitudinal ends of the sheath body 11 along the virtual extended line of the slit 111B. A plurality of slits 111B (i.e., a slit array) may alternatively be formed at intervals along the longitudinal direction of the sheath body 11. In this case, uncut portions 118 are defined between the slits 111B which constitute the slit array.

The length (i.e., a dimension along the longitudinal direction of the sheath body 11) of the uncut portion 118 is 0.5 to 10 mm and preferably 1 to 5 mm.

The uncut section 118 may fracture more easily with a cut-out groove (i.e., a notch section) provided to extend in the longitudinal direction of the sheath body 11.

In the sheath body 11, the load applied to the inner surface (i.e., the inner surface of the inner path 113) of the sheath body 11 is preferably not smaller than 0.5N to not greater than 5N in order to fracture at least one of the uncut portions 111a and 118. The load is more preferably not smaller than 0.5N to not greater than 3N. In this case, the sheath body 11 can be split smoothly with, for example, insertion of the indwelling section 22 in its reduced-diameter state.

Note that the notched groove 111A is advantageous to the slit 111B as the notch section in increased morphological stability of the sheath body 11 and maintenance of the configuration of the inner path 113 of the sheath body 11 when the sheath body 11 is inserted in the fistula.

Figure 16B:
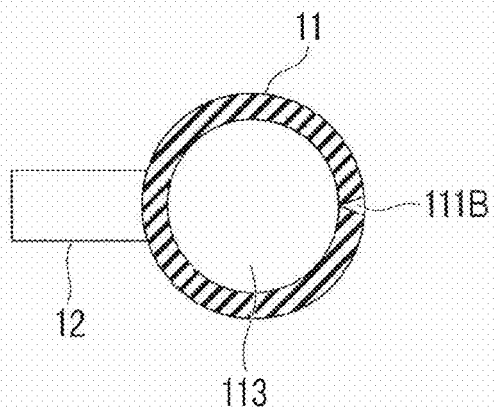
FIG. 16B schematically illustrates a cross-sectional structure and a position of a handle of the sheath body of the sheath for gastrostoma according to the invention, with a slit formed in the sheath body as a notch section.

In addition, in FIG. 16B, portions of the sheath body 11 located opposite to each other over the slit 111B are disposed close to each other and thus the slit 111B is substantially closed. However, it is not easy to completely close the slit 111B and to stably keep the closed state. On the contrary, the notched groove 111A is formed in the sheath body 11 so as not to penetrate the sheath body 11 in the thickness direction while providing the uncut portion 111a at the groove bottom side. Such a configuration has an advantage in that, as compared with the configuration with the slit 111B, air supplied from the endoscope does not leak in the radially outward direction of the sheath body 11 from the middle of the inner path 113 inside the sheath body 11.

In the sheath 1 of the illustrated example, the notch section is formed in the sheath body 11 only at one position along a circumferential direction of the sheath body 11. However, the invention includes a configuration in which notch sections are formed at a plurality of positions along the circumferential direction of the sheath body 11.

FIGS. 16A and 16B schematically illustrate an example in which the notch section is formed only at one position along the circumferential direction of the sheath body 11. FIG. 16A illustrates the notched groove 111A and FIG. 16B illustrates the slit 111B.

In FIGS. 16A and 16B, the handle 12 is provided at a position where the handle 12 does not interfere with the notch section (i.e., the notched groove 111A or the slit 111B) in the circumferential direction of the sheath body 11.

Accordingly, when the sheath body 11 is vertically split at the notch section as a cutout line, the sheath body 11 is not divided into two or more parts but remains as a single part. Thus, there is an advantage that the entire sheath body 11 can be easily removed from the fistula when the handle 12 is drawn.

Figure 17:
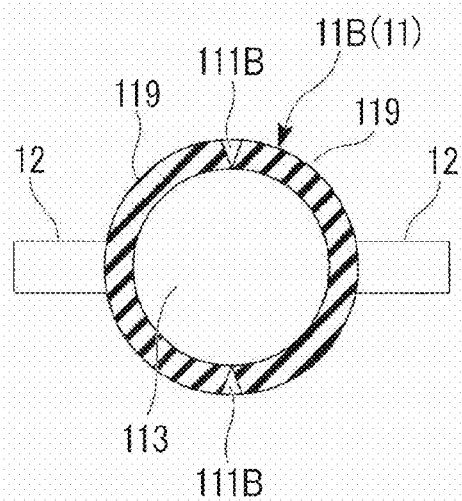
FIG. 17 is a cross-sectional view of a sheath for gastrostoma configured with the slits formed at two circumferential positions of the sheath body.

FIG. 17 schematically illustrates an example in which the notch sections (in illustrated example, the slits 111B) are formed at two positions in the circumferential direction of the sheath body 11.

The handle 12 is provided at a position where the handle 12 does not interfere with the notch sections. Here, the handle 12 is provided at each split part of the sheath body 11 (hereinafter, referred to as split pieces 119; in FIG. 17, the sheath body 11 is split into two split pieces 119) when the sheath body 11 is vertically split due to insertion of the button for gastrostoma 2. Thus, the handle 12 is provided at each of the split pieces 119.

The sheath body 11 is denoted by a reference numeral 11B in FIG. 17.

Note, of course, that the notched groove 111A may be employed in place of the slit 111B.

In the case of FIG. 16, as compared with the configuration of FIG. 17, the sheath body 11 can be drawn out of the fistula after vertical splitting in an easier manner.

It is preferable that the notch section (the notched groove 111A and the slit 111B) be formed in a wedge-shaped cross-section with its opening width increasing from an inner surface toward an outer surface of the sheath body 11.

In the notch section with such a cross-section shape, as the sheath body 11 is extended and deformed in a radially outward direction by the indwelling section 22 inserted in the inner path 113, the cross section of the notch section is also extended. Thus, the uncut portions 111a and 118 easily fracture from the notch section.

The notch section can be formed through, for example, laser processing or machining of the sheath body 11.

Laser processing is preferable because the opening width of the notch section can be easily adjusted and a notch section with a wedge-shaped cross-section can be easily formed through controlling the focal position of laser.

Also, when the notch section is formed in a FEP-based sheath body 11 (herein the sheath body 11 includes FEP as a major component) through laser processing (especially, laser processing with YAG laser), a portion of the sheath body 11 where the notch section has been formed can be whitened by the laser processing.

Thus, an easily visible mark is formed by this whitening so that a user can easily recognize the position of the notch section. As a result, the user can vertically split the sheath body 11 inserted in the fistula and draw out of the patient's body in an efficient manner.

Moreover, an end surface of the sheath for gastrostoma 1 at the side of the base end of the sheath body 11 is inclined with respect to the axial center (i.e., the central axis C1) of the sheath body 11.

In the sheath for gastrostoma 1 of the illustrated example, the end surface at the side of the base end of the sheath body 11 is inclined so that the side of the lid abutting section 117 is closer to the distal section of the sheath body 11 than the side of the hinge section 116.

With this configuration in which the end surface of the sheath body 11 at the side of the base end thereof is inclined with respect to the axial center (central axis C1) of the sheath body 11, the section of the opening of the inner path 113 at the base end of the sheath body 11 is increased substantially, which facilitates smooth insertion of the indwelling section 22 of the button for gastrostoma 2 in the sheath body 11 from the base end of the sheath body 11. Especially when an indwelling section 22 with the maximum outer diameter larger than the inner diameter of the sheath body 11 is pushed into the sheath body 11, such an opening section facilitates a smooth pushing operation in an efficient manner.

Next, an exemplary usage of the sheath for gastrostoma, the sheathed dilator and the gastrostomy catheter kit according to the invention will be described with reference to FIGS. 18 to 28.

The gastrostomy catheter kit includes the sheath for gastrostoma 1, the button for gastrostoma 2, the obturator 3 and the dilator 5. The gastrostomy catheter kit will be described later.

Figure 18:
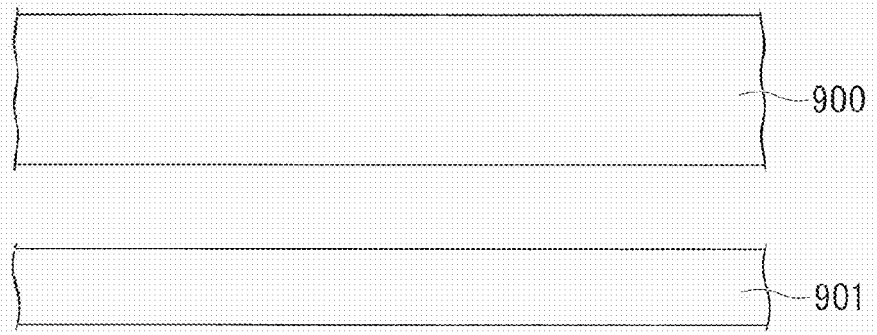
FIG. 18 illustrates a state in which an abdominal wall and a stomach wall have yet to be in contact with each other.

Before the sheath for gastrostoma 1 according to the invention is used, an endoscope is inserted in the stomach of a patient, i.e., a living body, and sufficient air is supplied to make an abdominal wall 900 and a stomach wall 901 closely contact each other (as illustrated in FIG. 18, the abdominal wall 900 and the stomach wall 901 are not in close contact with each other before they are made to closely contact each other). Then, the operator confirms the stomach position with light transmitted from the endoscope, palpates the abdomen from the body surface, determines a position where the stomach wall is to be fixed, disinfects the abdomen skin and applies local anesthesia.

Figure 19:
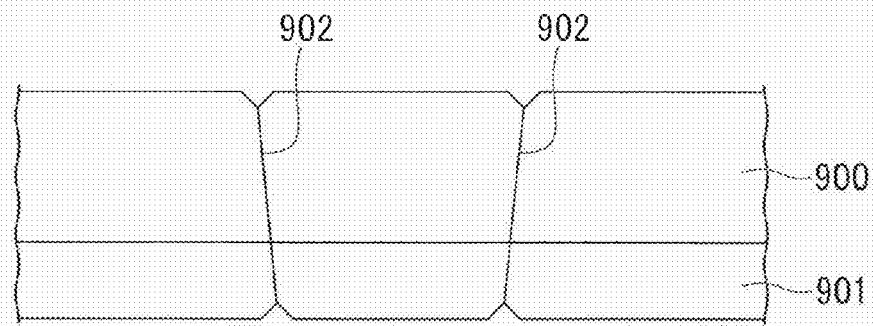
FIG. 19 illustrates a state in which the abdominal wall and the stomach wall are in contact with each other with a suture.
Figure 20:
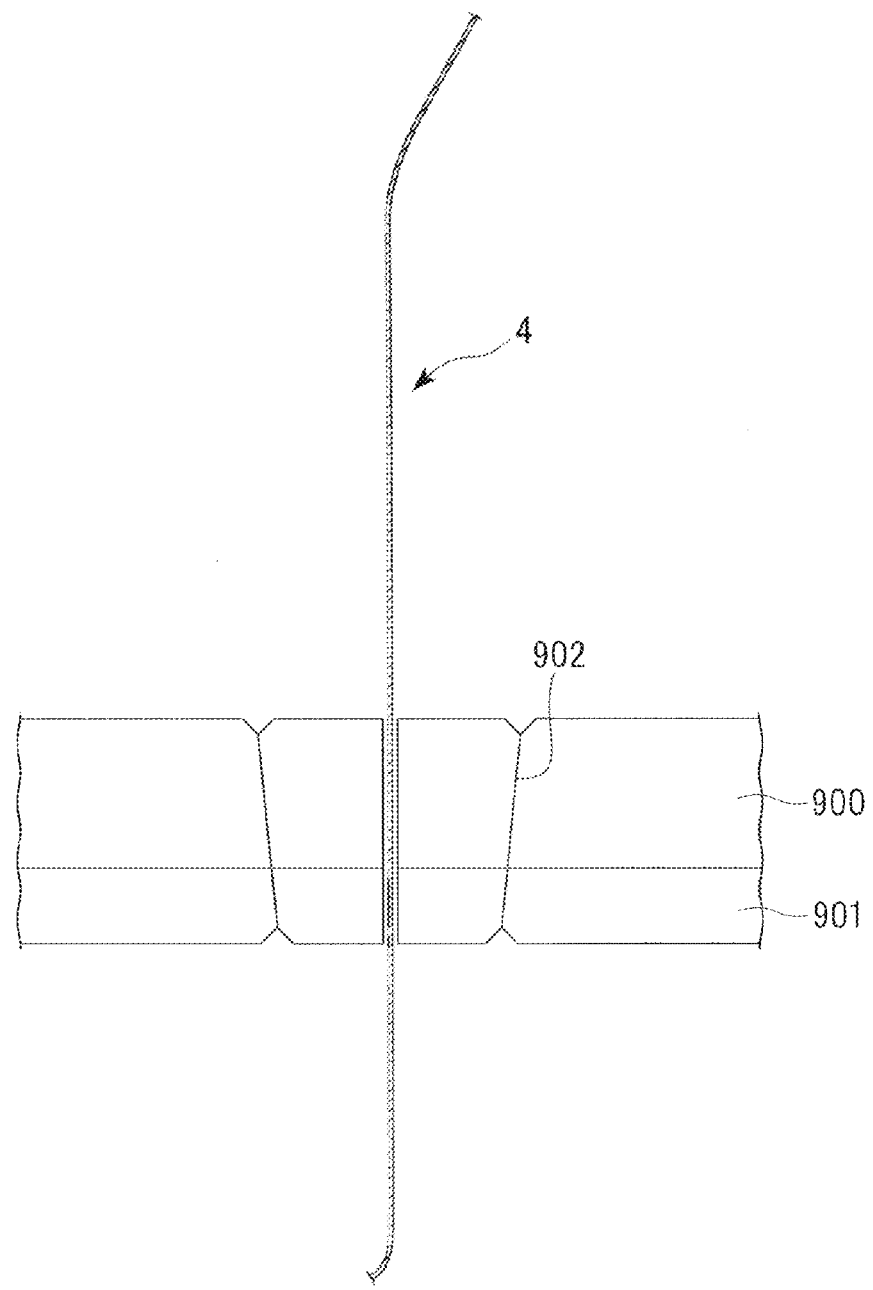
FIG. 20 illustrates a state in which a guidewire is placed.

Subsequently, the operator fixes the abdominal wall 900 and the stomach wall 901 together with a suture using a device for fixing the stomach wall and the abdominal wall (see FIG. 19).

The abdominal wall 900 and the stomach wall 901 should be fixed together with a suture usually at two points so as to provide a site for catheter gastrostomy as a plane in the later step.

After the stomach wall and the abdominal wall are fixed together, a cannula needle is inserted in the abdominal wall and the stomach wall from the body surface to leave the guidewire 4.

The dilator 5 is inserted through the guidewire 4 which is left in the patient's body (i.e., the guidewire 4 is made to pass through the guidewire path 524 of the dilator 5). The dilator 5 with the sheath for gastrostoma 1 disposed thereon (sheathed dilator 5A) is inserted in the abdominal wall and the stomach wall from the body surface to form a one-stage fistula (see FIG. 21). At this time, the dilator is inserted while being twisted to provide safe extension.

In addition, when the dilator 5 is inserted in the abdominal wall and the stomach wall to form the fistula, the operator positions the reference point 5141 of the scale 514 (see FIG. 12A) on the peripheral surface of the large-diameter dilator body section 511 at the stomach wall surface (inner surface) and reads the scale provided on the body surface side so as to measure the distance from the body surface to the stomach wall inner surface under the endoscope. With this measurement, the length of the tubular section 21 of the button for gastrostoma 2 can be selected. A position of the stopper 33 of the obturator 3 (i.e., a position at which the stopper 33 is mounted along the longitudinal direction of the outer case 32) is determined in accordance with the selection of the tube 21.

The length of a portion of the obturator 3 inserted into the tubular section 21 is determined in accordance with the length of the tubular section 21 of the button for gastrostoma 2. Adjustment of the mounting position of the stopper 33 in the longitudinal direction of the outer case 32 enables the extension force to be reliably applied by the obturator 3 to the indwelling section 22 of the button for gastrostoma 2 anchored by the stopper 33. The mounting position of the stopper 33 in the longitudinal direction of the outer case 32 is selected by selectively engaging the arm 331 of the stopper 33 with the plurality of fitting portions 323 and the plurality of fit-in grooves 323a provided along the longitudinal direction of the outer case 32.

In order to provide easy reading of the scale 514 of the dilator 5, the sheath body 11 may preferably have transparency that enables the scale 514 of the dilator 5 to be viewed from outside.

Figure 22:
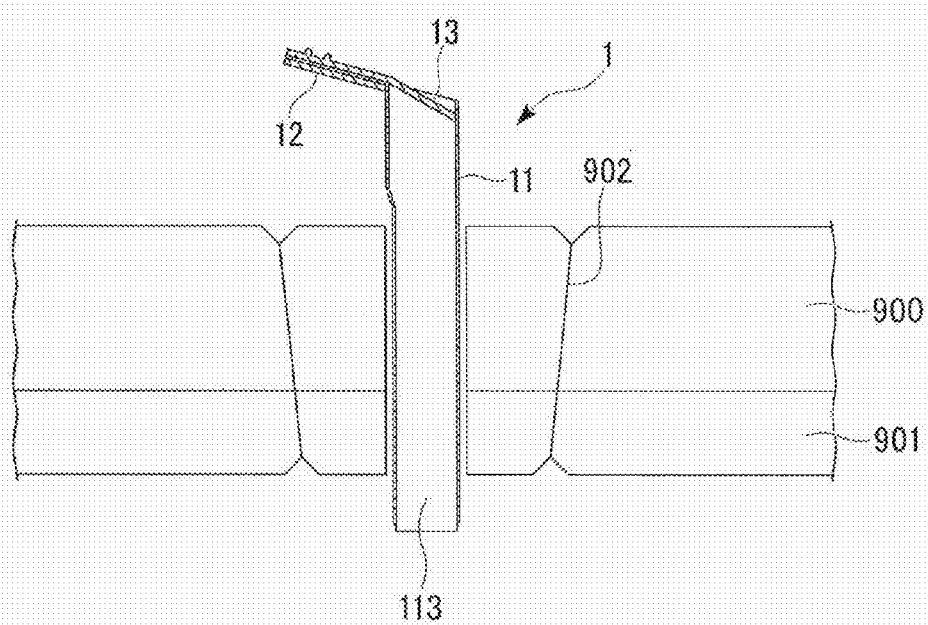
FIG. 22 illustrates a state in which the sheath for gastrostoma is placed.

When extension is completed, the dilator 5 and the guidewire 4 are removed from the body while leaving the sheath for gastrostoma 1 (see FIG. 22).

When the dilator 5 is removed from the sheath for gastrostoma 1, the lid 13 of the sheath for gastrostoma 1 closes to block the inner path 113. The lid 13 comes to the closed position due to elasticity of the hinge section 116 as described above. The inner path 113 may also be closed with air itself supplied into the stomach from the endoscope.

Thus, leakage of the air supplied from the endoscope outside of the body can be reduced.

Figure 23:
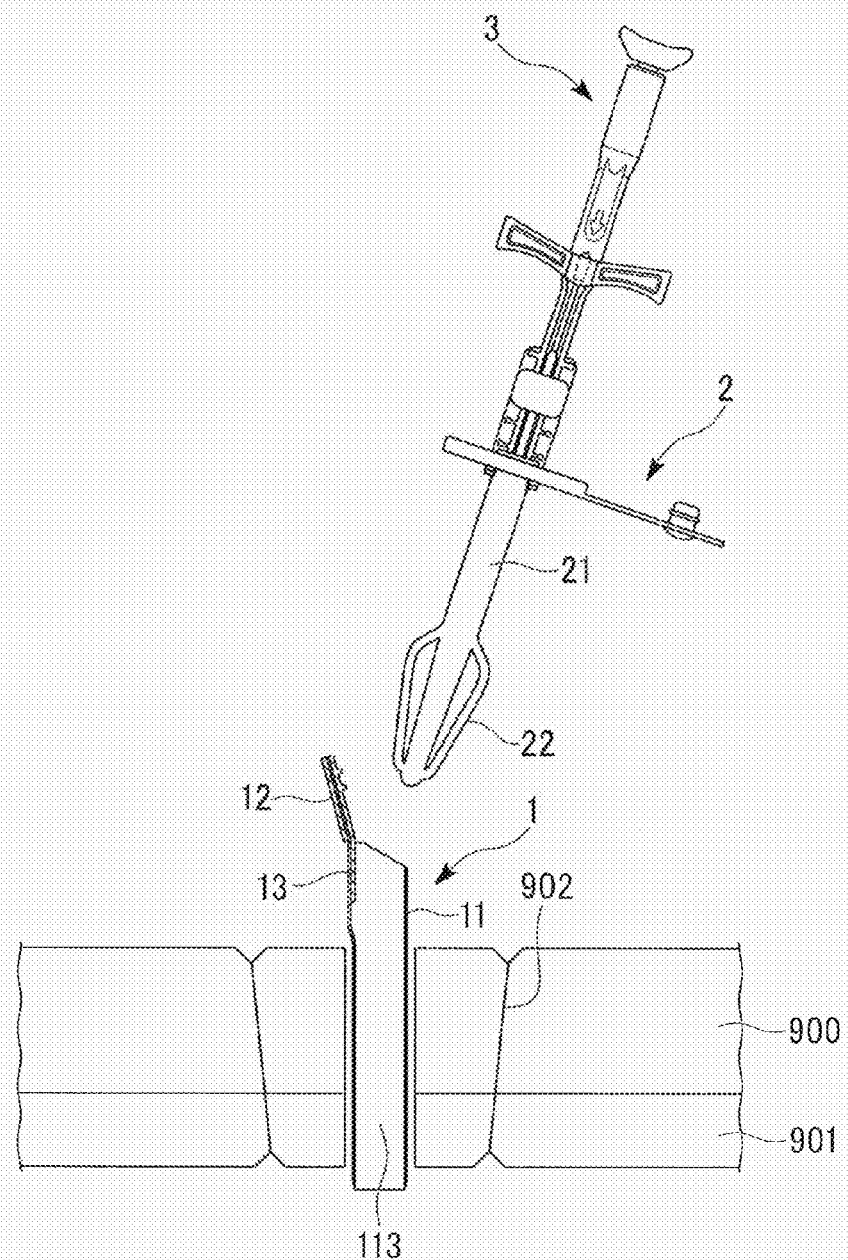
FIG. 23 is a state in which the button for gastrostoma is being inserted in the sheath for gastrostoma.
Figure 24:
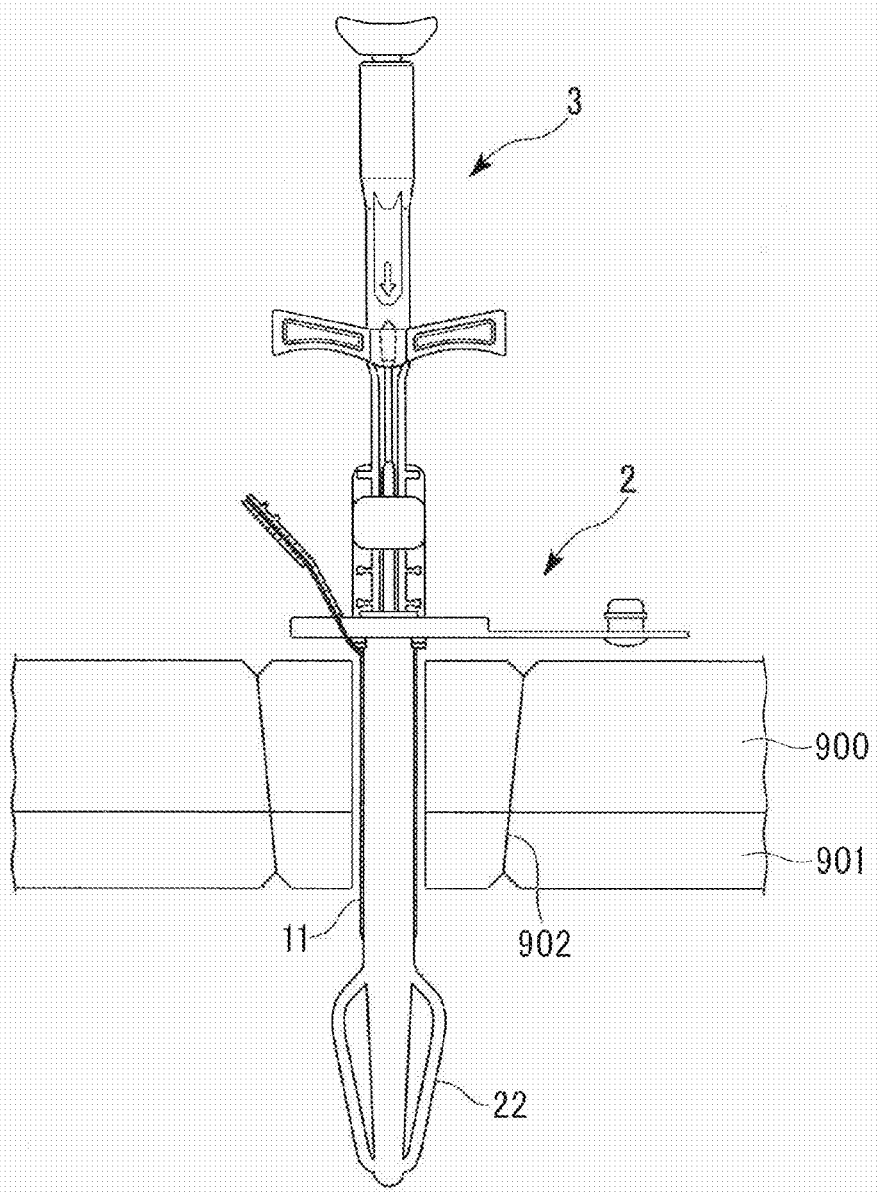
FIG. 24 is a state in which the button for gastrostoma has been inserted from an inner path of the sheath for gastrostoma.

Then, the operator grasps the handle 12 to open the lid 13 of the sheath for gastrostoma and inserts the button for gastrostoma 2 of which indwelling section 22 has been extended with the obturator 3 in the inner path 113 of the sheath for gastrostoma (see FIG. 23).

Since the sheath for gastrostoma 1 is provided with a means which splits along the longitudinal direction, the sheath body 11 is split in the longitudinal direction and is developed when a portion of the extended indwelling section 22 of the button for gastrostoma 2 having the outer diameter larger than the inner diameter of the sheath for gastrostoma 1 is inserted in the sheath body 11. The button for gastrostoma 2 makes its indwelling section 22 pass through the sheath 1 to reach the stomach, where the indwelling section 22 is left (see FIG. 24).

In addition, when the button for gastrostoma 2 extended with the obturator 3 is inserted, the most distal section of the indwelling section 22 can be inserted smoothly with lowered insertion resistance since an insertion route is established in the inner path 113 of the sheath for gastrostoma 1.

Figure 25:
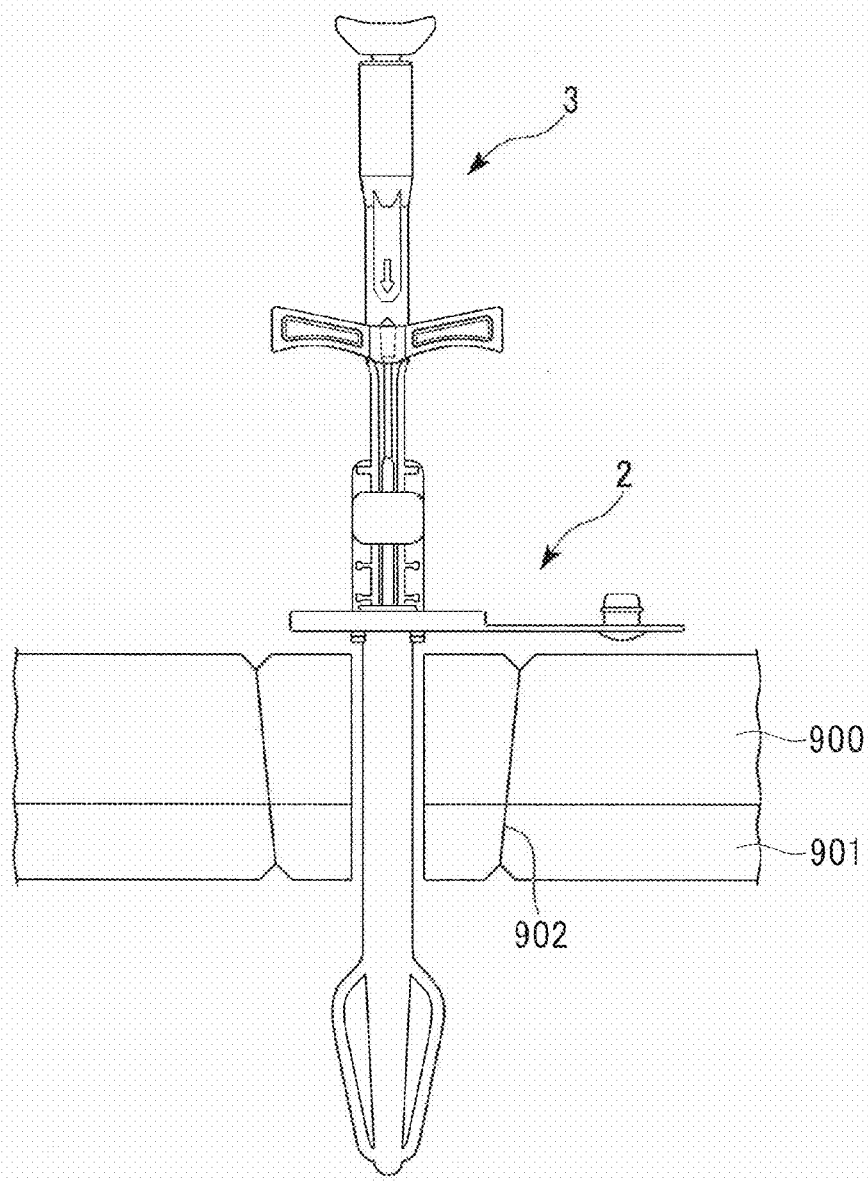
FIG. 25 illustrates a state in which only the button for gastrostoma is placed after the sheath for gastrostoma is removed.

After the button for gastrostoma 2 is placed in the stomach, the sheath for gastrostoma 1 is removed from the body in a state in which the button for gastrostoma 2 is still extended with the obturator 3 (FIG. 25).

Figure 26:
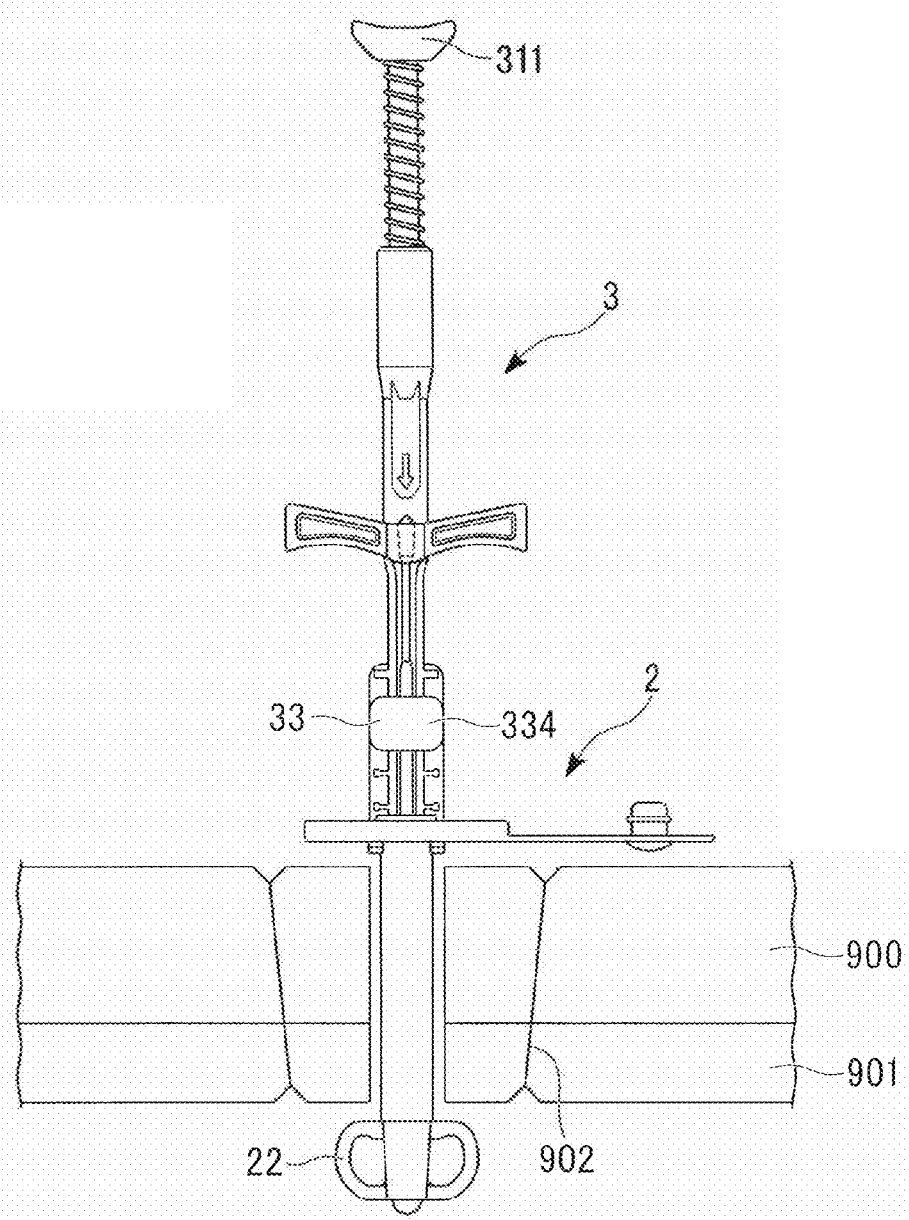
FIG. 26 illustrates a state in which extension of the obturator is released.
Figure 27:
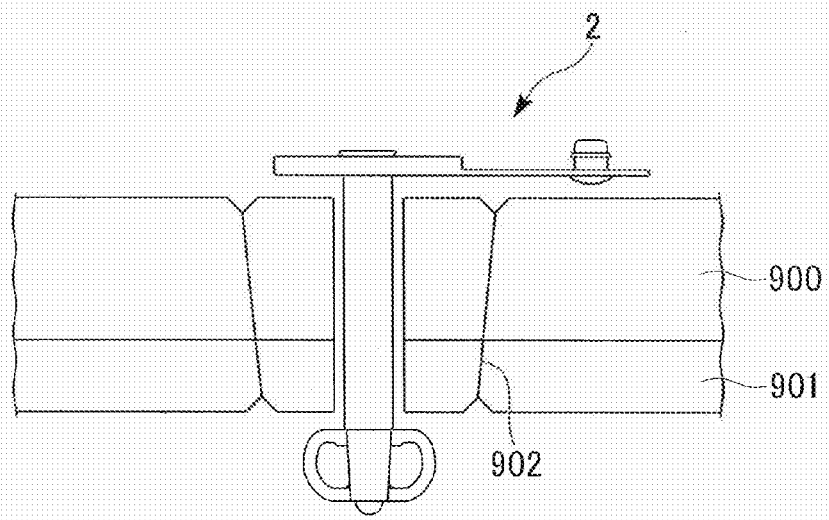
FIG. 27 illustrates a state in which the obturator is removed.
Figure 28:
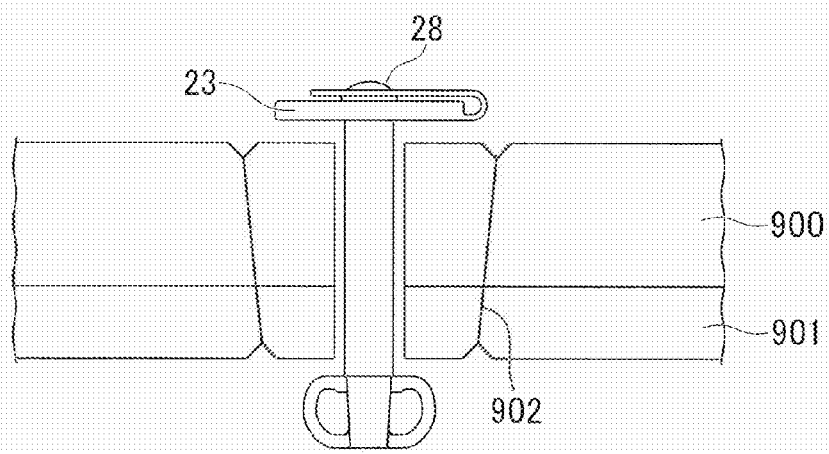
FIG. 28 illustrates a state in which placement of the button for gastrostoma is completed.

The operator pushes the pushed-in portion 334 of the stopper 33 attached to the obturator 3 toward the back plate 333 so that the arms 331 are slid to cancel the extension of the indwelling section of the button for gastrostoma 2 (see FIG. 26).

Then, the operator withdraws the obturator 3 disposed on the button for gastrostoma 2 (see FIG. 27) and places the cap 28 attached to the externally fixed section 23 of the button for gastrostoma 2 so as to block the path 24. In this manner, leaving the button for gastrostoma 2 in the patient's body is completed (see FIG. 28).

As described above, usage of the sheath for gastrostoma 1 according to the invention lowers insertion resistance during insertion of the button for gastrostoma 2 and enables easy control of the endoscope regarding air supply during gastrostomy.

Figure 29:
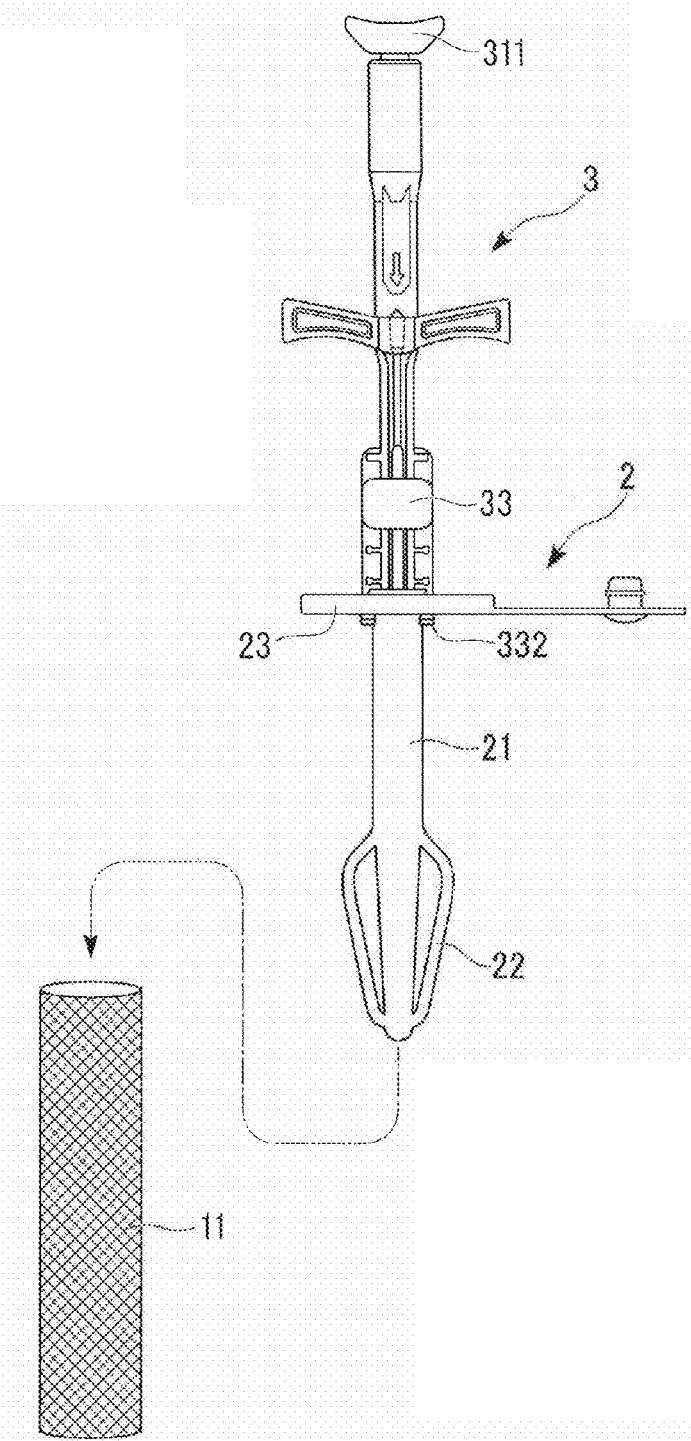
FIG. 29 illustrates a state before the button for gastrostoma extended with the obturator is inserted in the radially expandable sheath body.
Figure 30:
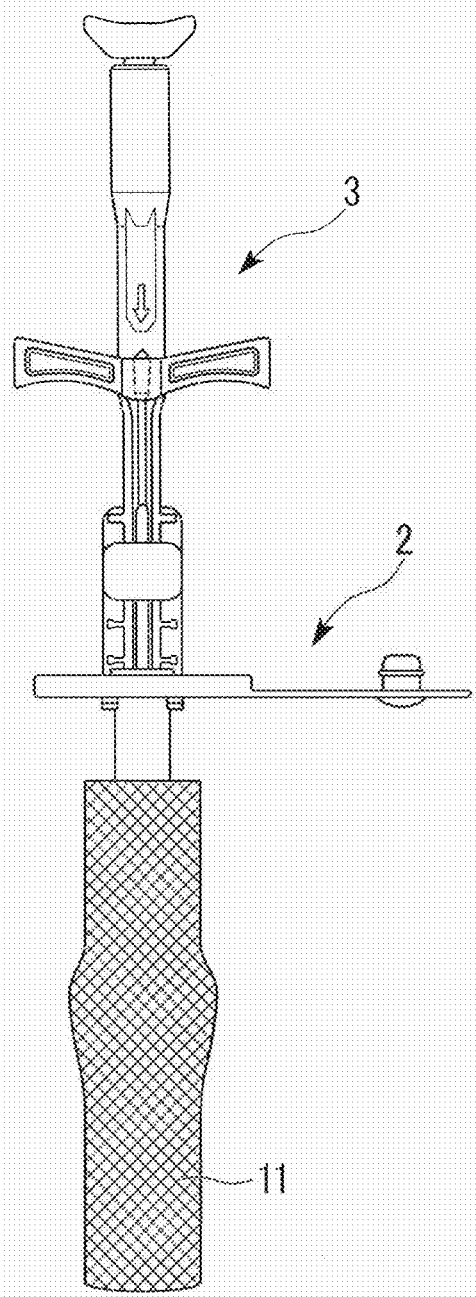
FIG. 30 illustrates a state in which the button for gastrostoma extended with the obturator is being inserted in the radially expandable sheath body.

Also, the sheath body 11 of the sheath for gastrostoma may be formed of a deformable material and thus expandable radially (see FIG. 29). At the time of insertion of the button for gastrostoma, if the outer diameter of the indwelling section of the button for gastrostoma 2 of which the indwelling section 22 has been extended with the obturator 3 is larger than the inner diameter of the sheath body 11, the sheath body 11 is expanded radially in accordance with the configuration of the indwelling section 22 (see FIG. 30).

Examples of the material of the sheath body 11 in this case include plastic materials or elastomeric materials, such as polyurethane resin, tetrafluoroethylene and fluorinated ethylene propylene.

In addition, the sheath body 11 may be formed as a braided product in which inelastic filaments, such as polyamide fiber and stainless steel, are braided to provide a mesh structure. In this case, the braided product which constitutes the sheath body 11 may, for example, also be constituted so that the radial extension of the sheath body 11 may shorten the sheath body 11 in the axial direction thereof.

As described above, with the sheath body 11 made of a radially expandable material, insertion resistance of the button for gastrostoma 2 can be lowered when the button for gastrostoma 2 is inserted in the inner path 113 of the sheath body 11.

In addition, the sheath body 11 made of a radially expandable material may preferably be provided with a configuration with which the sheath body 11 can be split vertically. For example, a fine wire (i.e., a wire for vertical splitting including a high tension fiber, such as polyamide fiber) is embedded along the entire axial direction length of the sheath body 11 which is made of the plastic material or the elastomeric material described above. When the operator pulls strongly an end of the wire for vertical splitting which has been made to extend toward the base end of the sheath body 11, the wire for vertical splitting is removed from the sheath body 11. Then, a thin-walled section for vertical splitting is formed in the sheath body 11. With this configuration, the sheath body 11 can be easily split vertically. In this case, for example, when the operator pulls the wire for vertical splitting from the sheath body 11 to make the sheath body 11 vertically split after the indwelling section 22 of the button for gastrostoma 2 is made to pass, from outside of the body, through the sheath body 11 which has been inserted in the fistula, the sheath body 11 can be removed from the fistula while leaving the button for gastrostoma 2 in the body.

(Another Embodiment of Sheath for Gastrostoma)

As illustrated in FIGS. 31A, 31B and 32A to 32E, the sheath for gastrostoma according to the invention may employ a configuration in which a lid 63 is pivotably provided in a handle 61 via a hinge section 62 (hereinafter, also referred to as a lid hinge section) which is provided separately from a hinge 116.

Figure 31A:
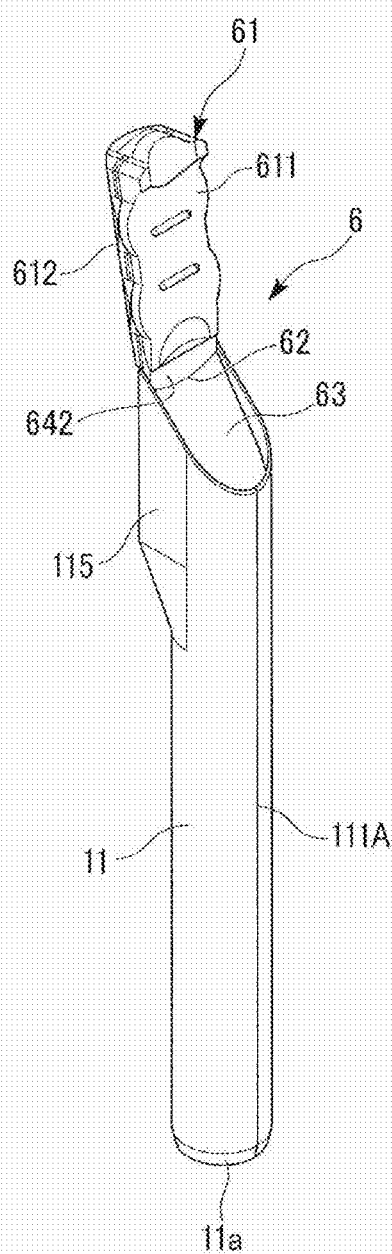
FIG. 31A illustrates another embodiment of the sheath for gastrostoma according to the invention, which is a perspective view with the lid closed.
Figure 31B:
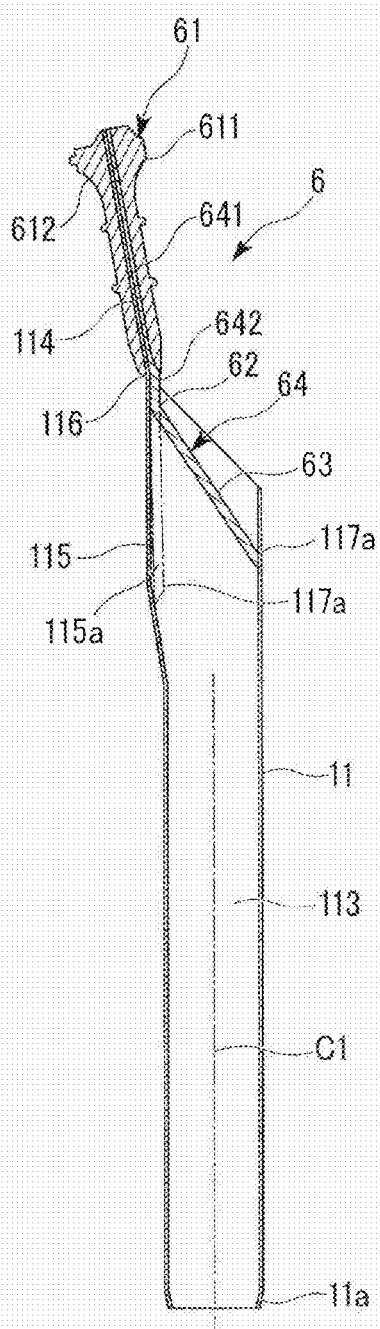
FIG. 31B is a left cross-sectional view of the sheath for gastrostoma of FIG. 31A with the lid closed.
Figure 32A:
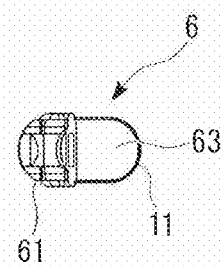
FIG. 32A is a top view of the sheath for gastrostoma of FIG. 31A with the lid closed.
Figure 32B:
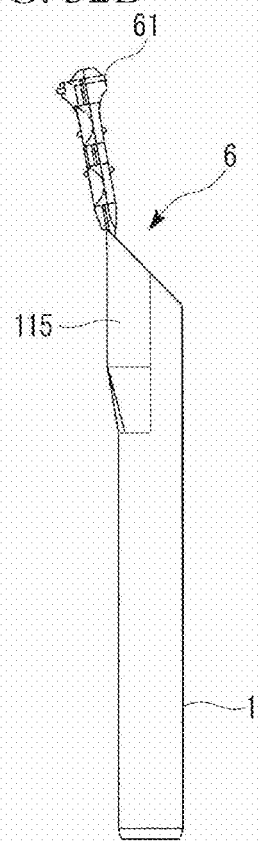
FIG. 32B is a left side view of the sheath for gastrostoma of FIG. 31A with the lid closed.
Figure 32C:
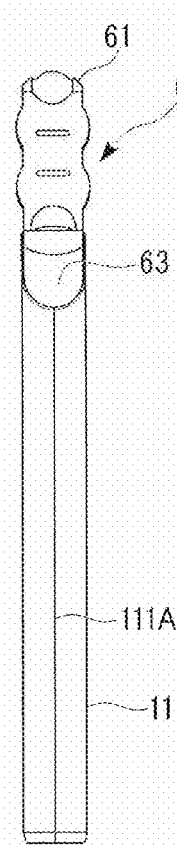
FIG. 32C is a front view of the sheath for gastrostoma of FIG. 31A with the lid closed.
Figures 32D, 32E:
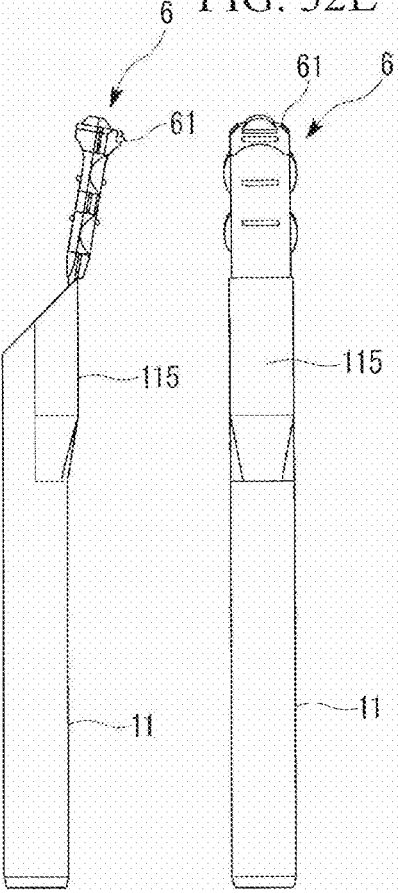
FIG. 32D is a right side view of the sheath for gastrostoma of FIG. 31A with the lid closed.
FIG. 32E is a rear view of the sheath for gastrostoma of FIG. 31A with the lid closed.
Figure 32F:
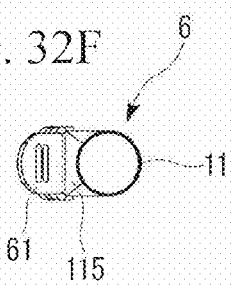
FIG. 32F is a bottom view of the sheath for gastrostoma of FIG. 31A with the lid closed.

A sheath for gastrostoma 6 illustrated in FIGS. 31A and 31B has a schematic structure which includes a sheath body 11 (sheath tube), the handle 61, the lid hinge section 62 and the lid 63.

The handle 61 extends from the base end of the sheath body 11 of the sheath for gastrostoma 6 as a tongue-shaped piece. The handle 61 may be used by an operator who grasps the sheath for gastrostoma 6 when inserting the button for gastrostoma in the sheath for gastrostoma 6.

This handle 61 is configured by fixing a pair of plate-like handle members 611 and 612 to a tongue-shaped handle main piece 114 which extends from the base end of the sheath body 11. The pair of handle members 611 and 612 is attached integrally with the handle main piece 114 so as to sandwich the handle main piece 114 therebetween.

In addition, the sheath for gastrostoma 6 of the illustrated example includes a synthetic resin-made elongated plate lid member 64 in which the lid hinge section 62 and the lid 63 are formed. This elongated plate lid member 64 is integrally molded from synthetic resin as one component. This elongated plate lid member 64 is formed of a material with rubber elasticity, such as silicone rubber and elastomer.

This elongated plate lid member 64 has a mounting section 641 via the lid hinge section 62 at a side opposite to the lid 63 and is integral with the handle 61 with the mounting section 641 fixed to the handle 61. A portion of the elongated plate lid member 64 further toward the lid 63 from the mounting section 641 is formed as a tongue-shaped piece extending from the handle 61 and inserted in the sheath body 11.

The lid 63 is disposed in the inner path 113 of the sheath body 11 and is elastically supported at a closed position (i.e., a position illustrated in FIG. 31B) at which the lid 63 closes the inner path 113 due to elasticity of the elongated plate lid member 64 itself.

In particular, the handle 61 has a configuration in which the plate-like mounting section 641 and the handle main piece 114 of the elongated plate lid member 64 are sandwiched between and integrally fixed to the pair of handle members 611 and 612.

Examples of a method (configuration) for sandwiching and integrally fixing the mounting section 641 and the handle main piece 114 of the elongated plate lid member 64 between the pair of handle members 611 and 612 (i.e., the lid side handle member 611 and the main piece side handle member 612) include the following configurations: a configuration in which the other handle member is engaged by one handle member by an engaging pawl provided to protrude from one or both of the pair of handle members 611 and 612 and the mounting section 641 and the handle main piece 114 of the elongated plate lid member 64 are sandwiched between and fixed to the pair of handle members; and a configuration in which the pair of handle members 611 and 612, the mounting section 641 of the elongated plate lid member 64 and the handle main piece 114 are made to integrally adhere together using an adhesive.

Also, the pair of handle members 611 and 612, the mounting section 641 of the elongated plate lid member 64 and the handle main piece 114 may be integrally bundled together using a bundling member for bundling the mounting section 641 of the elongated plate lid member 64 and the handle main piece 114. The bundling member is not particularly limited as long as it can bundle the mounting section 641 of the elongated plate lid member 64 and the handle main piece 114 together (i.e., it can integrate the mounting section 641 of the elongated plate lid member 64 and the handle main piece 114 together so that no relative misalignment may occur). For example, a configuration in which a heat-shrinkable tube is used and the mounting section 641 of the elongated plate lid member 64 and the handle main piece 114 are integrally bundled together through heat shrinking of this heat-shrinkable tube.

Note that the pair of handle members 611 and 612 may be provided separately from each other or may be provided integrally with each other.

In addition, it suffices that the mounting section 641 be integrally fixed to the handle 61 to form a tongue-shaped portion of which the portion of the elongated plate lid member 64 further toward the lid 63 from the mounting section 641 is extended from the handle 61 and inserted in the sheath body 11. The position at which the mounting section 641 is fixed to the handle 61 is not necessarily between the pair of handle members 611 and 612.

Moreover, the handle does not necessarily include a plate-like handle member. A configuration may be employed in which, for example, the handle includes no handle member but is constituted by the handle main piece 114 and the mounting section 641 of the elongated plate lid member 64.

As illustrated in FIG. 31B, the distal end of the lid 63 is made to abut or be disposed close to the inner wall surface of the sheath body 11 at the side opposite to the handle 61 across the inner path 113.

The lid hinge section 62 is provided at the base end side of the lid 63 and is formed as a tongue-shaped portion extending from the handle 61 of the elongated plate lid member 64.

The lid 63 extends in a manner inclined from the lid hinge section 62 toward the distal end of the sheath body 11 at an angle of smaller than 90 degrees with respect to the axial center (central axis C1) of the sheath body 11. The lid 63 is elastically supported with elasticity of the lid hinge section 62 and the distal end of the lid 63 is made to abut or be disposed close to the inner wall surface of the sheath body 11 at the side opposite to the handle 61 across the inner path 113.

The lid 63 is supported to be pivotable about the lid hinge section 62 along an axis extending perpendicular to the axial center of the sheath body 11 (i.e., an axis parallel to the pivot axis of the hinge section 116). When the lid 63 is pivoted clockwise from the closed position illustrated in FIG. 31B (i.e., pivoted toward an opening direction) to open the inner path 113 of the sheath body 11. The lid 63 pivoted from the closed position in the open direction by external force applied by, for example, insertion of a device, such as the dilator 5, into the sheath body 11 returns to the closed position with the elasticity of the lid hinge section 62 when the external force acting as displacement force in the open direction is eliminated by, for example, withdrawal of the dilator 5, which had been inserted in the sheath body 11, from the sheath body 11.

Also, pivotation of the lid 63 in a direction opposite to the direction from the closed position in the open direction, i.e., counterclockwise pivotation from the closed position in FIG. 31B, is restricted by the distal end abutting the sheath body 11. Thus, the lid 63 can be kept in a state which closes the inner path 113 of the sheath body 11. When, for example, the handle 61 is pivoted counterclockwise about the hinge section 116 in FIG. 31B and pivoting force in a direction opposite to the open direction is applied to the lid 63 located at its closed position, pivotation of the lid 63 abutting the sheath body 11 is restricted and the lid hinge section 62 is elastically deformed. Thus, in this sheath for gastrostoma 6, a state can be kept in which the lid 63 closes the inner path 113 of the sheath body 11 when the pivoting force in a direction opposite to the open direction is applied to the lid 63. Accordingly, there is an advantage that outflow of air supplied from endoscope in the stomach can be avoided.

The distal end of the lid 63 is pressed against the sheath body 11 when the lid is pivoted from the closed direction toward the direction opposite to the open direction.

Hereinafter, a portion of the sheath body 11 where the distal end of the lid 63 is made to abut will be referred to as a lid abutting section (denoted by a reference numeral 117*a*).

The hinge section 116 and the lid hinge section 62 are provided in the sheath body 11 at a side opposite to the lid abutting section 117*a* across the inner path 113. The distal end of the lid 63 is made to abut the lid abutting section 117*a* from the direction of the distal end of the sheath body 11 when the lid 63 is pivoted from the closed direction in the open direction.

The lid hinge section 62 and a stopper projection piece 642 are formed between the mounting section 641 of the elongated plate lid member 64 and the lid 63.

The stopper projection piece 642 is formed as a projecting piece extending from the handle 61 and inserted in the sheath body 11 and is disposed along an inner surface of the sheath body 11 at a side opposite to the lid abutting section 117*a* across the inner path 113. In particular, the stopper projection piece 642 is made to abut or be disposed close to the inner surface of the expanded section 115 formed in the sheath body 11.

The lid hinge section 62 is provided at a distal end of the stopper projection piece 642 in a direction in which the stopper projection piece 642 protrudes from the handle 61. The lid 63 extends from the distal end of the stopper projection piece 642 in a direction in which the stopper projection piece 642 protrudes from the handle 61 in a manner inclined toward the distal end of the sheath body 11 at an angle of smaller than 90 degrees with respect to the axial center (central axis C1) of the sheath body 11. The lid hinge section 62 is located in a connecting section at which the stopper projection piece 642 and the lid 63 continue to each other. The lid hinge section 62 corresponds to a bending section at which the elongated plate member 64 is formed to be bent.

When force is applied to the lid 63 to pivot the same from the closed position in the open direction, pivotation of the lid 63 with respect to the sheath body 11 is restricted by the stopper projection piece 642 being pressed against the inner surface of the sheath body 11. Pivotation of the lid 63 from the closed position in the open direction is allowed due to elastic deformation of the lid hinge section 62.

At this time, pivotation of the handle 61 following the lid 63 can be restricted by the stopper projection piece 642 which is not pivoted even when the lid 63 is pivoted from the closed position in the open direction due to elastic deformation of the lid hinge section 62. Thus, since the position of the handle 61 with respect to the sheath body 11 is stabilized, failure of a user of this sheath for gastrostoma 6 to grasp the handle 61 with the fingers occurs less often, thereby securing good workability. That is, the configuration of this sheath for gastrostoma 6 is that, when the handle 61 is pivoted clockwise in FIG. 31B about the hinge section 116, the stopper projection piece 642 is pressed against the inner wall surface of the sheath body 11 and pivotation is restricted. Thus, pivotation of the lid 63 from the closed position in the open direction is restricted to keep the state in which the inner path 113 of the sheath body 11 is closed.

That is, the sheath for gastrostoma 6 is less often affected by the pivotation of the handle 61 about the hinge section 116 in the state in which the lid 63 is disposed at the closed position and the lid 63 is elastically supported at the closed position with the elasticity of the lid hinge section 62 in the state in which no external force is applied to the handle 61 or the elongated plate lid member 64. Thus, in the event that the user of the sheath for gastrostoma 6 inadvertently touches the handle 61, the lid 63 is not easily pivoted in the open direction and, even when being pivoted in the open direction, the lid 63 returns to its closed position immediately. Accordingly, the state in which the lid 63 closes the inner path 113 of the sheath body 11 can be stably continued.

In addition, the stopper projection piece 642 formed of a material with rubber elasticity, such as silicone rubber and elastomer, is disposed between the handle 61 and the lid hinge section 62. When the handle 61 is pivoted, the stopper projection piece 642 elastically deforms so that following displacement of the lid hinge section 62 or the lid 63 with respect to the handle 61 occurs less often. This configuration also contributes to effectively maintaining the state in which the lid 63 closes the inner path 113 of the sheath body 11.

Note that any materials can be used for the elongated plate lid member 64 as long as they provide the lid hinge section 62 with elasticity that allows the lid 63 to pivot from the closed position (the position illustrated in FIGS. 31A and 31B) to a position at which the lid 63 touches the inner surface of the sheath body 11 at a side opposite to the lid abutting section 117a, and allows the lid 63 to return to the closed position from position at which the lid 63 touches the inner surface of the sheath body 11 at a side opposite to the lid abutting section 117a. Such materials are not limited to materials with rubber elasticity, such as silicone rubber and elastomer described above, but various synthetic resin materials can be employed. For example, materials that can be used for forming the sheath body 11 may also be employed as the materials of the elongated plate lid member 64.

In the sheath for gastrostoma according to the invention, for example, in the elongated plate lid member, the lid hinge section and the lid may be formed integrally with each other from a material with rubber elasticity, such as silicone rubber and elastomer. Alternatively, only the lid hinge section may be formed of a material with rubber elasticity, such as silicone rubber and elastomer, and other portions may be formed of a hard material with no rubber elasticity, such as rigid resin or metal.

The sheath for gastrostoma 6 described here may also be used in an operation to form a fistula (gastrostomy) and place the button for gastrostoma 2 in the patient's body as in the sheath for gastrostoma described above with reference to FIGS. 1A and 1B.

Figure 39:
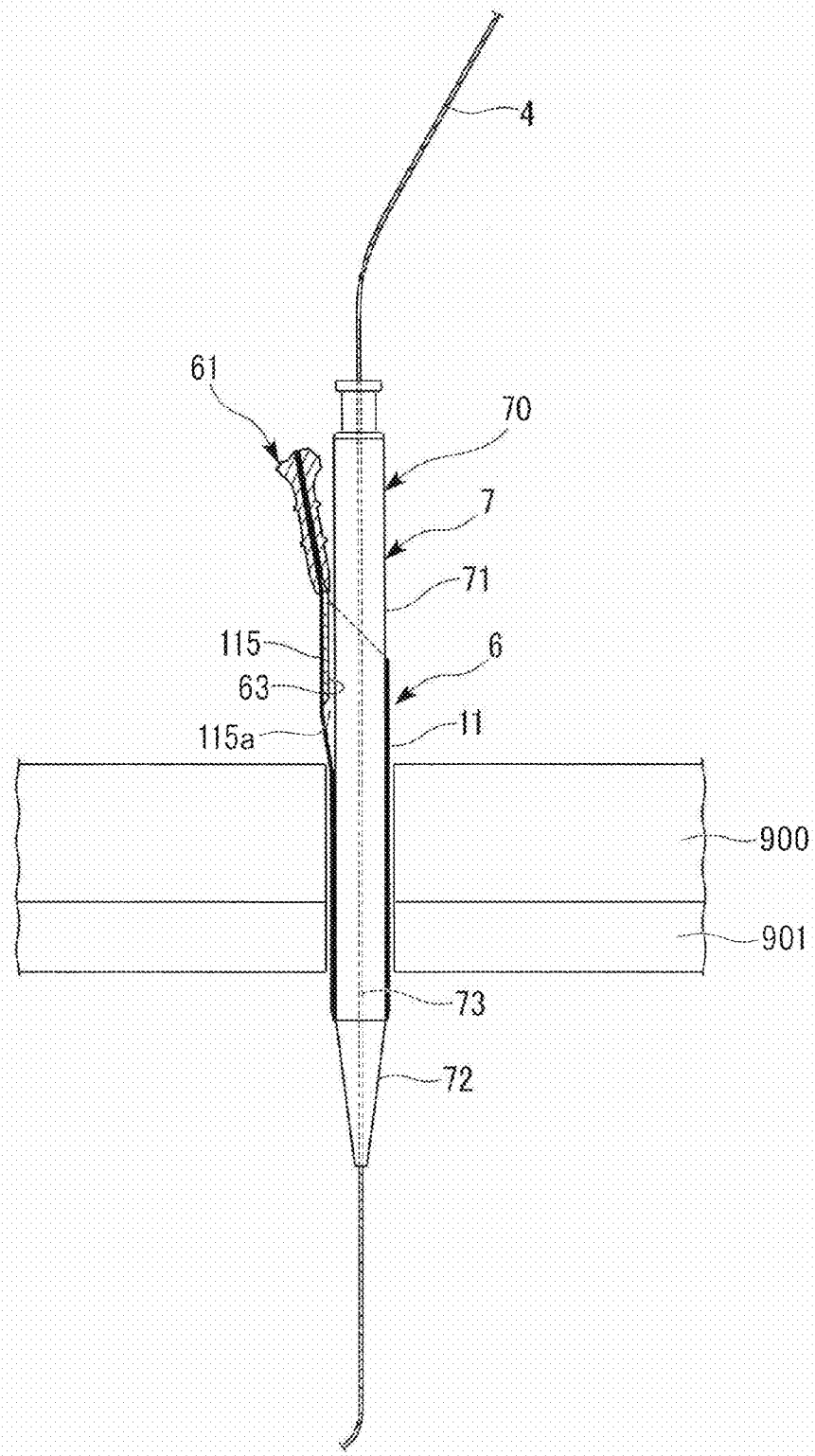
FIG. 39 illustrates a state in which a sheath with insertion aid obtained by disposing the sheath for gastrostoma outside of the sheath insertion aid is inserted in the fistula by using the guidewire as a guidance member.

As in the sheath for gastrostoma described above, the dilator 5 may be inserted in the sheath body 11 to provide a sheathed dilator (see FIG. 39).

In addition, as described above, in the sheath for gastrostoma 6, the lid 63 is pivoted from the closed position in the open direction when the dilator 5 is inserted in the sheath body 11, and the lid 63 pivoted from the closed position in the open direction returns to the closed position with the elasticity of the lid hinge section 62 when the dilator 5 inserted in sheath body 11 is removed from the sheath body 11 to close the inner path 113 of the sheath body 11. Since it is possible to prevent outflow of air supplied into the stomach from an endoscope in the state in which the sheath for gastrostoma 6 is inserted in the fistula, the sheath for gastrostoma 6 can be suitably used in an operation for forming a fistula and placing the button for gastrostoma 2 in the patient's body and in an operation for replacing the button for gastrostoma 2 placed in the patient's body.

Here, a procedure of replacing the button for gastrostoma 2 placed in the patient's body using the sheath for gastrostoma 6 will be described.

Figure 33:
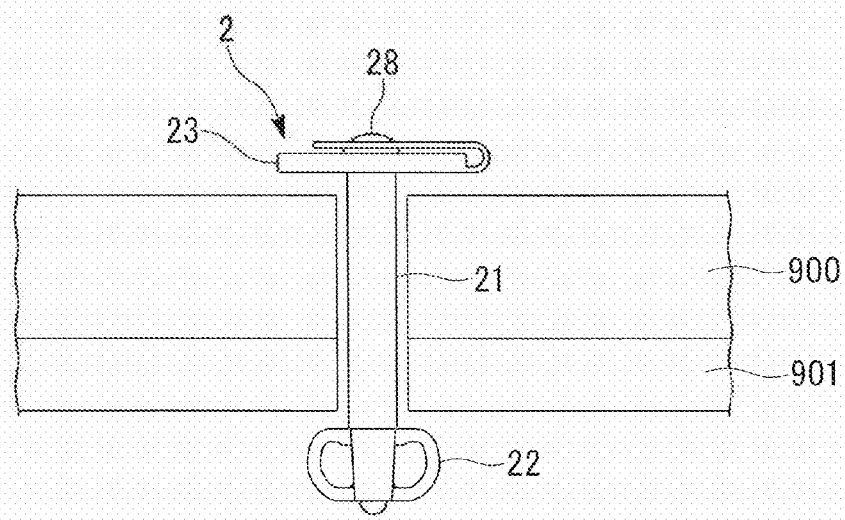
FIG. 33 illustrates a button placed in the fistula.

FIG. 33 illustrates the button for gastrostoma 2 placed in the patient's body.

Figure 34:
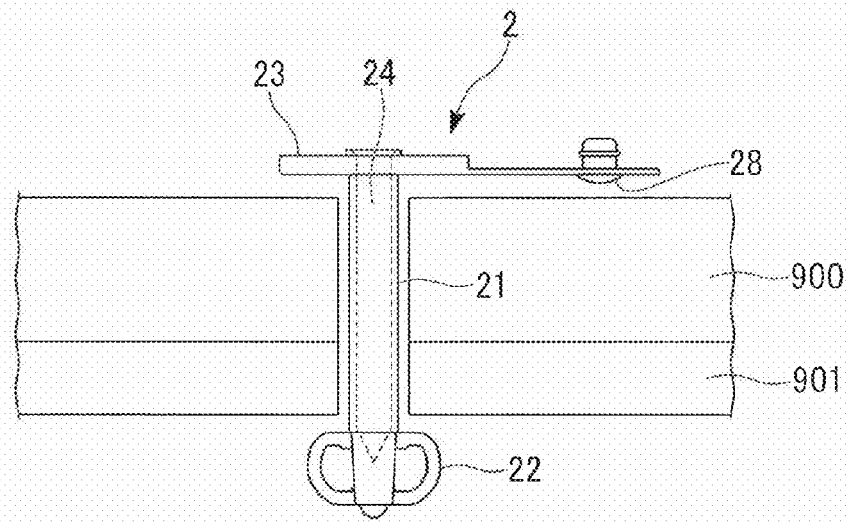
FIG. 34 illustrates a state in which a cap of the button for gastrostoma has been removed.
Figure 35:
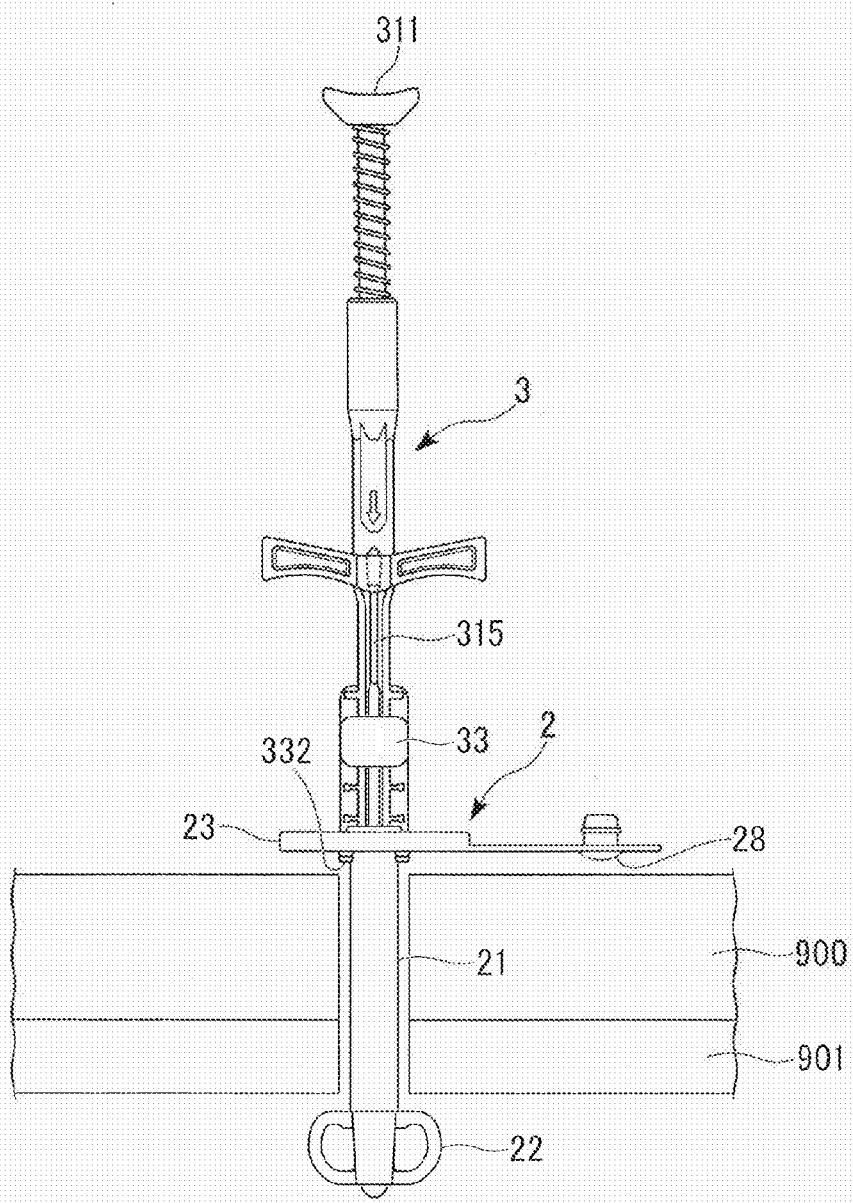
FIG. 35 illustrates a state in which the obturator is inserted in an inner cavity of the button for gastrostoma and an externally fixed section of the button is held by a stopper.
Figure 36:
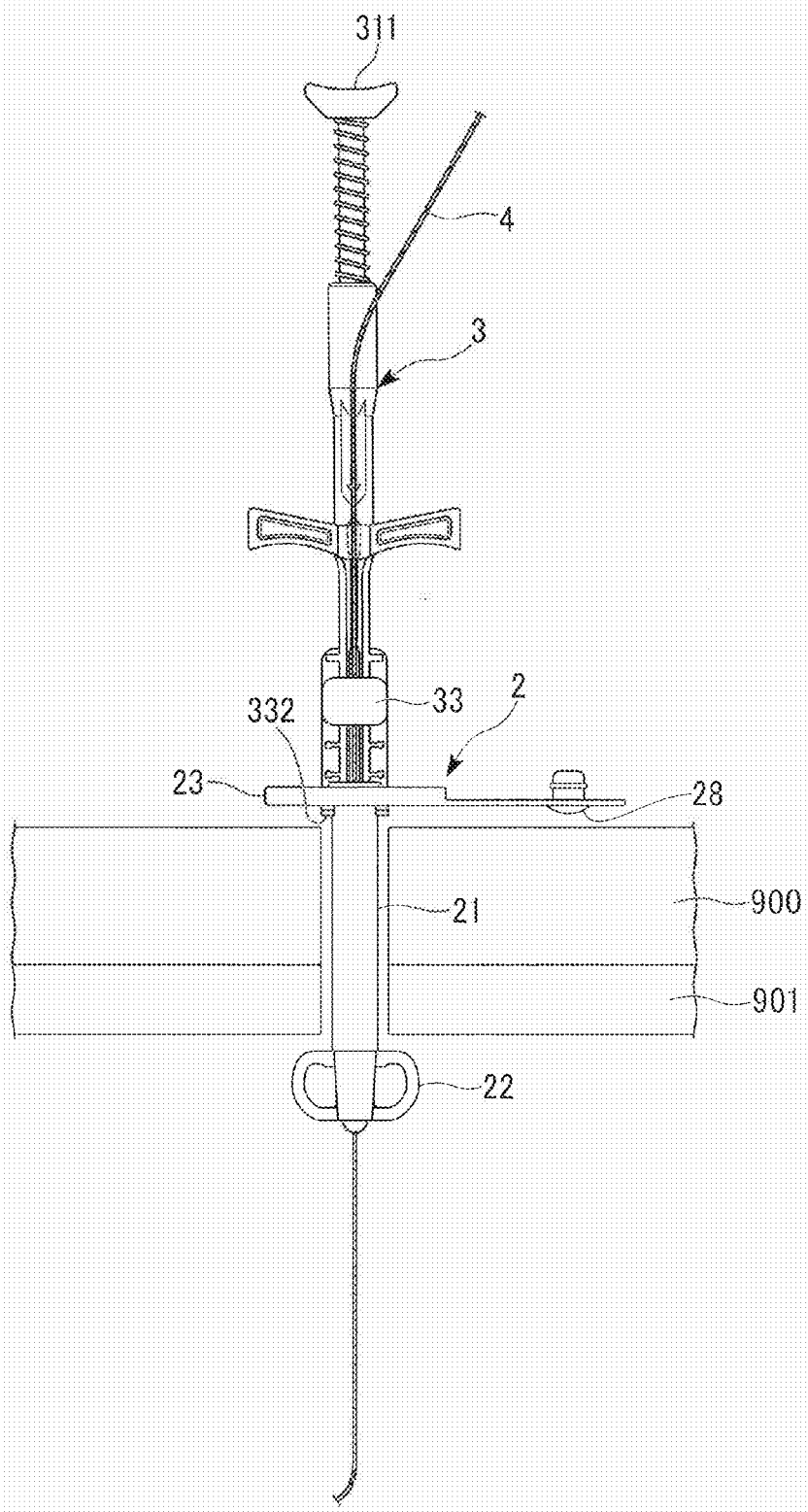
FIG. 36 illustrates a state in which the guidewire is inserted from a guidewire insertion hole of the obturator and is made to protrude from a distal end of the button for gastrostoma.
Figure 37:
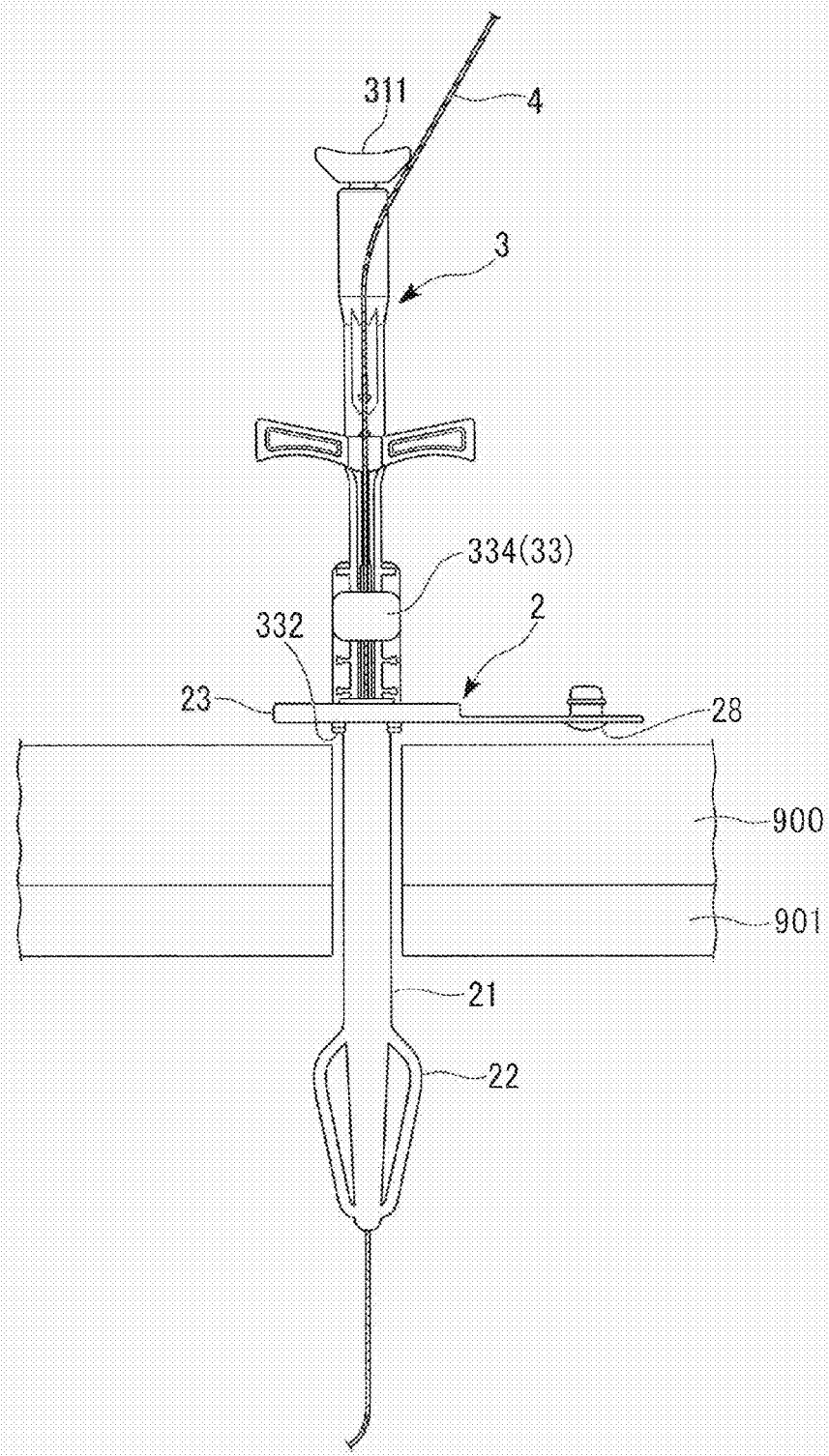
FIG. 37 illustrates a state in which an operating section of the obturator assembled to the button for gastrostoma is pressed so that the indwelling section of the button for gastrostoma adopts an extended state.
Figure 38:
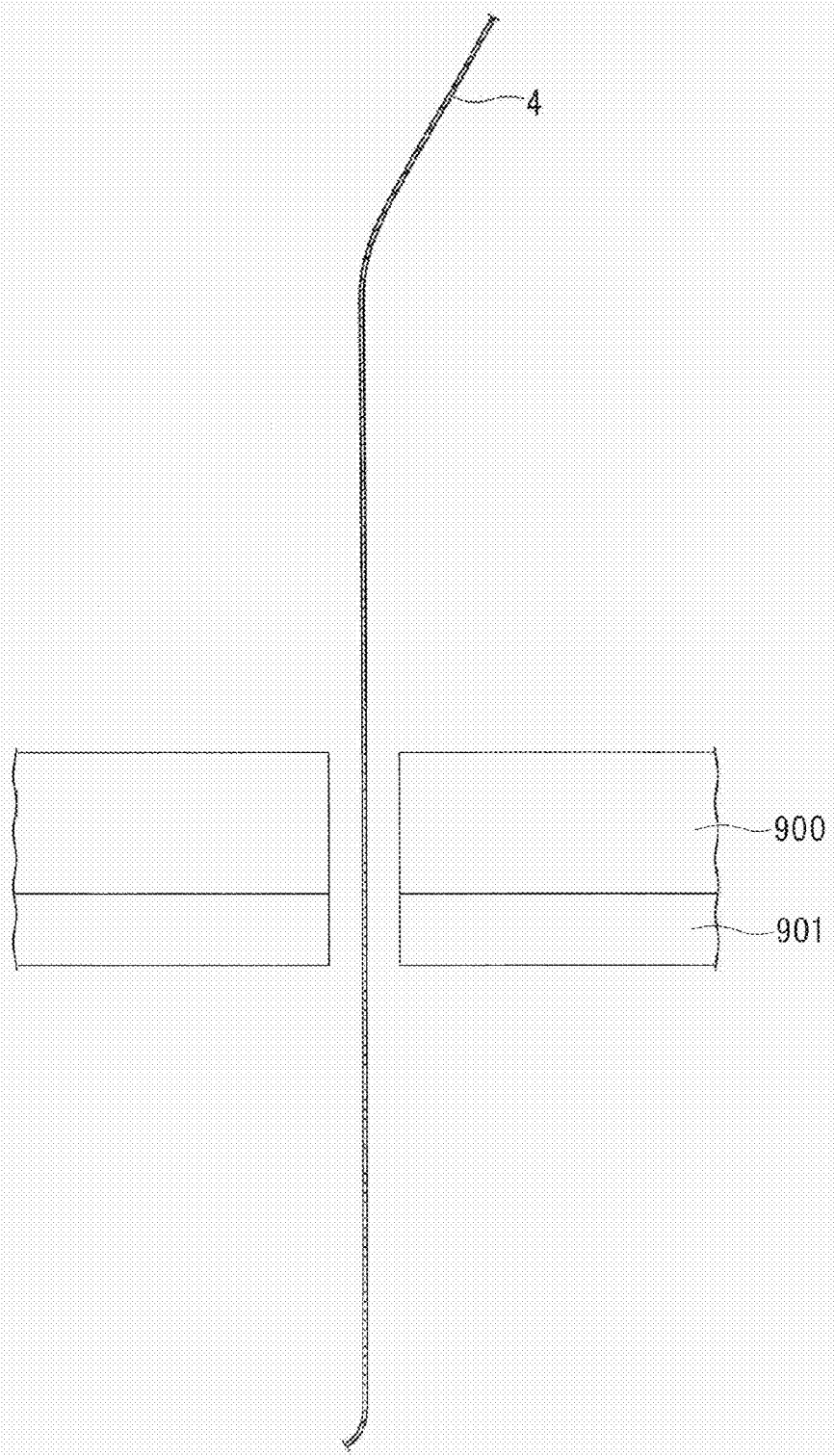
FIG. 38 illustrates a state in which the obturator, the button for gastrostoma and the guidewire are removed, leaving the guidewire alone in the fistula.

In order to replace the button for gastrostoma 2, as illustrated in FIG. 34, the cap 28 fitted into the opening of the path 24 of the button for gastrostoma 2 at the side of the externally fixed section 23 is removed from the opening of the path 24 to release the opening of the path 24. Then, as illustrated in FIG. 35, the obturator 3 is inserted in the path 24 from outside of the body and placed in the button for gastrostoma 2 (i.e., the distal section 317 of the pushing rod for extension 31, i.e., the distal end of the outer case 32 is inserted in the path 24 of the button for gastrostoma 2 and the stopper 33 (in particular, the holding section 332) is engaged by the externally fixed section 23 of the button for gastrostoma 2). A guidewire 4 is inserted through the path 24 in the tubular section 21 of the button for gastrostoma 2 to reach the stomach from outside of the body using the wire insertion groove 315 of the obturator 3 as illustrated in FIG. 36. Subsequently, as illustrated in FIG. 37, the obturator 3 is operated so that the indwelling section 22 of the button for gastrostoma 2 is extended (i.e., reduced in diameter) and the obturator 3 and the button for gastrostoma 2 are removed from the fistula to the outside of the body together (see FIG. 38). As illustrated in FIG. 38, the guidewire 4 is left in the patient's body.

Figure 40:
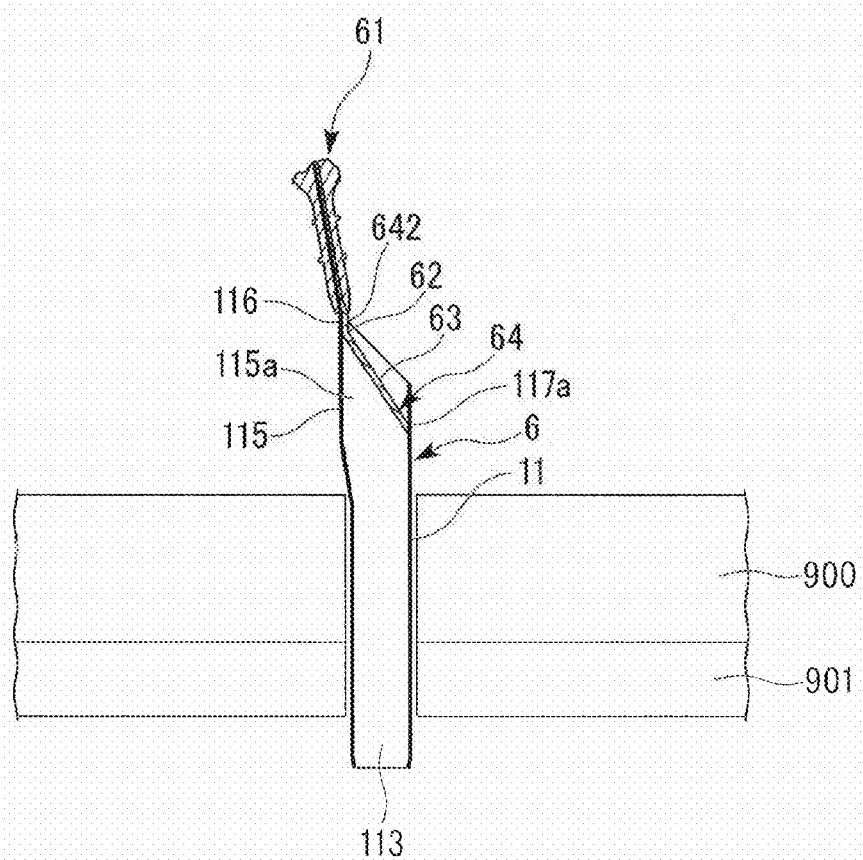
FIG. 40 illustrates a state in which the sheath insertion aid and the guidewire are removed, leaving the sheath for gastrostoma alone.

Then, as illustrated in FIG. 40, the sheath for gastrostoma 6 is inserted in the fistula and placed in the patient's body.

At this time, as illustrated in FIG. 39, it is preferable to, for example, insert a sheath insertion aid 7 having a rod-shaped appearance in the sheath body 11 to assemble a sheath for gastrostoma with an insertion aid 70 (hereinafter, also referred to as a sheath with insertion aid). The sheath with insertion aid 70 is inserted in the fistula and then the sheath for gastrostoma 6 is inserted in the fistula for placement of the button for gastrostoma 2.

The sheath insertion aid 7 includes a rod-shaped body 71 and a tapered distal section 72 having a tapering configuration provided to protrude from one longitudinal end (distal end) of the rod-shaped body. In the sheath insertion aid 7, an outer diameter of the rod-shaped body 71 is equivalent to or slightly smaller than the inner diameter of the sheath body 11 and thus the sheath insertion aid 7 can be removably inserted in the sheath body 11. This sheath insertion aid 7 includes a guidewire insertion hole 73 to penetrate the same in the longitudinal direction. The guidewire 4 is inserted in the guidewire insertion hole 73 so that the sheath insertion aid 7 is disposed outside of the guidewire 4. One of both ends of the guidewire insertion hole 73 opens at a distal end of the tapered distal section 72 of the sheath insertion aid 7 and the other opens at an end (rear end) of the rod-shaped body 71 at the side opposite to the tapered distal section 72.

As illustrated in FIG. 39, the procedure of inserting the sheath for gastrostoma 6 in the fistula using the sheath with insertion aid 70 and leaving in the patient's body is as follows. First, a portion of the guidewire 4 placed in the patient's body extending from the fistula toward outside of the body is inserted in the guidewire insertion hole 73 of the sheath insertion aid 7 and the sheath insertion aid 7 and the entire sheath with insertion aid 70 are disposed outside of the guidewire 4. After the sheath with insertion aid 70 is inserted in the fistula with the guidewire 4 as a guidance member, the sheath insertion aid 7 is removed outside of the body while leaving the sheath for gastrostoma 6 in the fistula, as illustrated in FIG. 40.

The sheath with insertion aid 70 is assembled by inserting the sheath insertion aid 7 in the opening at the side of the base end of the sheath body 11 of the sheath for gastrostoma 6 from the distal end and then making the tapered distal section 72 of the sheath insertion aid 7 protrude from the distal end of the sheath body 11. By making the tapered distal section 72 protrude from the distal end of the sheath body 11, insertion resistance at the time of inserting the sheath with insertion aid 70 in the fistula (inserting from the tapered distal section 72 side) can be lowered and insertion can be performed smoothly. The tapered distal section 72 also has a function to extend the fistula when the sheath with insertion aid 70 is inserted in the fistula.

It suffices that the sheath insertion aid 7 have a function to facilitate the procedure of inserting the sheath for gastrostoma 6 and the entire sheath with the insertion aid 70 in the fistula and extend the fistula, and thus the sheath insertion aid 7 does not necessarily have a function to form a new fistula. However, the sheath insertion aid 7 may also be used for fistulization. In this case, the dilator described above may be used as a sheath insertion aid 7.

In the sheath with insertion aid 70 in which the sheath insertion aid 7 is inserted in the sheath for gastrostoma 6, as illustrated in FIG. 39, the lid 63 of the sheath for gastrostoma 6 is moved from the closed position in the open direction by the sheath insertion aid 7 inserted in the sheath body 11 and is housed in the expanded section 115 (inside the inner space 115a) at the base end of the sheath body 11. As illustrated in FIG. 40, immediately after the sheath insertion aid 7 is removed from the sheath for gastrostoma 6, the lid 63 returns to the closed position with the elasticity of the lid hinge section 62. That is, when the sheath insertion aid 7 is removed from the sheath for gastrostoma 6 of the sheath with insertion aid 70 inserted in the fistula, the lid 63 closes the inner path 113 of the sheath body 11 automatically with no operation of the handle 61, thereby preventing ingression of foreign object into the inner path 113. When an endoscope is used, there is an advantage that outflow of air supplied from the endoscope to the stomach can be avoided.

The following configurations can be commonly applied to the sheath for gastrostoma of each embodiment according to the invention: a configuration with a sheath body 11 in which the sheath insertion aid 7 can be inserted; and a configuration in which the sheath with insertion aid 70 can be assembled by inserting the sheath insertion aid 7 in the sheath body.

As illustrated in FIG. 31B, it is noted that the distal section (a bottom section in FIG. 31B) of the sheath body 11 of the sheath for gastrostoma 6 is formed as a tapered distal end 11a which is tapered from the sheath body 11 to reduce its diameter. The inner diameter of the distal end of the tapered distal end 11a, i.e., the minimum inner diameter of the tapered distal end 11a, is substantially equivalent to the outer diameter of the sheath insertion aid 7.

This tapered distal end 11a has a function to avoid the formation of a level difference resulting from a difference between the outer diameter of the sheath insertion aid 7 and the inner diameter of the sheath body 11 inserted in the sheath body 11 and to smoothly insert the sheath body 11 of the sheath for gastrostoma 6 in the fistula. The configuration providing a tapered distal end 11a at the distal section of the sheath body 11 can be commonly applied to each embodiment according to the invention.

Figure 41:
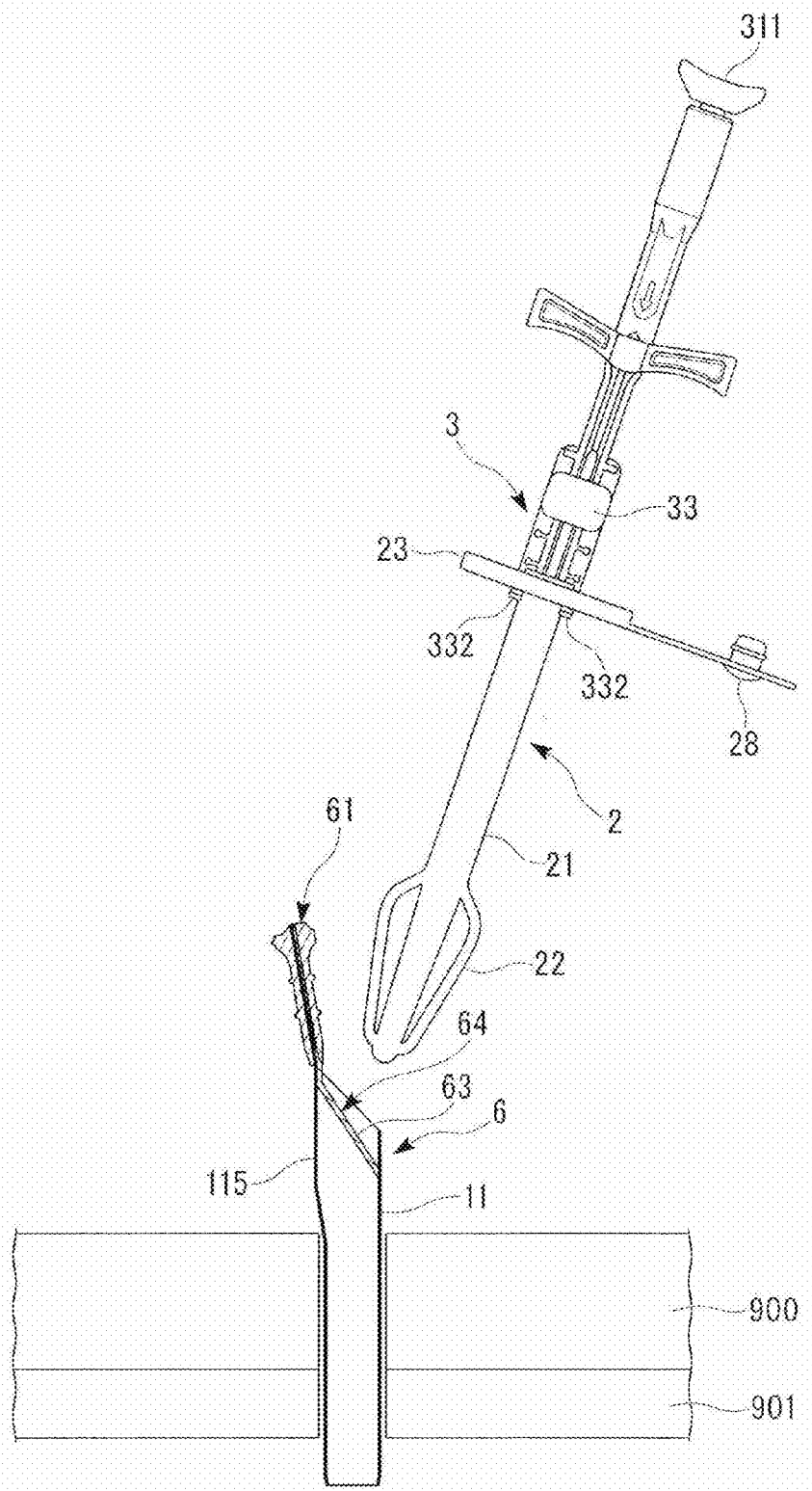
FIG. 41 illustrates a state in which the button for gastrostoma has been inserted in the fistula via the sheath for gastrostoma.
Figure 42:
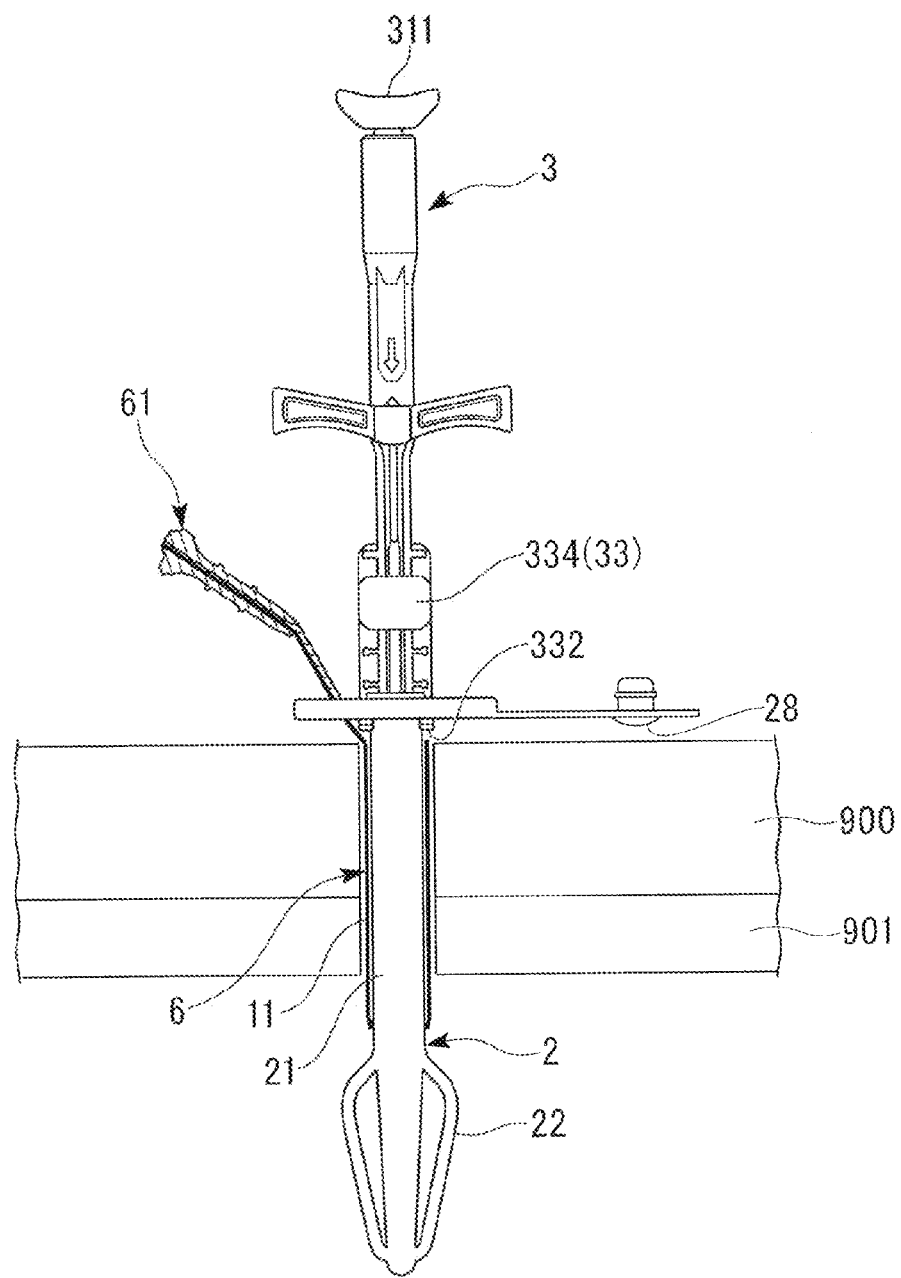
FIG. 42 illustrates a state in which the button for gastrostoma is placed in the stomach via the sheath for gastrostoma.

Next, the obturator 3 is assembled to and disposed in the button for gastrostoma 2 for a fistula to be newly formed as illustrated in FIG. 41. The operating section 311 of the obturator 3 is operated (i.e., pushed) to extend (i.e., reduce in diameter) the in-body fixing portion 23 of the button for gastrostoma 2. The button for gastrostoma 2, while keeping a state in which the in-body fixing portion 23 is extended, is inserted in the inner path 113 of the sheath body 11 of the sheath for gastrostoma 6 placed in the fistula from the in-body fixing portion 23. Then, the in-body fixing portion 23 is made to protrude inside the patient's body from the sheath for gastrostoma 6 (see FIG. 42).

Then, in the same manner as described above with reference to FIGS. 25 to 28, the sheath for gastrostoma 6 is removed from the patient's body, the in-body fixing portion 23 is stopped to advance (i.e., extend) and the obturator 3 is removed outside of the patient's body. In this manner, placement of the button for gastrostoma 2 for newly provided fistula in the patient's body is completed.

In the replacement of the button for gastrostoma 2 using the sheath for gastrostoma 6, as described above, when the sheath insertion aid 7 is removed from the sheath for gastrostoma 6 of the sheath with insertion aid 70 inserted in the fistula, a state can be obtained in which the lid 63 closes the inner path 113 of the sheath body 11 automatically without requiring operation of the handle 61. Thus, time and effort to close the inner path 113 can be omitted.

When the sheath insertion aid 7 is withdrawn from the sheath for gastrostoma 6 of the sheath with insertion aid 70 inserted in the fistula, a state can be obtained in which the lid 63 closes the inner path 113 of the sheath body 11 automatically without requiring operation of the handle 61. Thus, outflow of air supplied to the stomach from the endoscope can be prevented. Such an advantage is not limited to replacement of the button for gastrostoma 2 but may be provided in new gastrostomy. Gastrostomy using the sheath for gastrostoma 6 is achieved by using the sheath for gastrostoma 6 in place of the sheath for gastrostoma 1 in gastrostomy described with reference to FIGS. 18 to 28.

In addition, replacement of the button for gastrostoma 2 described with reference to FIGS. 34 to 42 can also be carried out using the sheath for gastrostoma 1 described with reference to FIGS. 1A and 1B.

Using the sheath for gastrostoma (sheath for gastrostoma according to the invention) in replacement of the button for gastrostoma 2 has an advantage that insertion resistance at the time of insertion of the button for gastrostoma 2 (sheath for gastrostoma for replacement) can be lowered.

Figure 43:
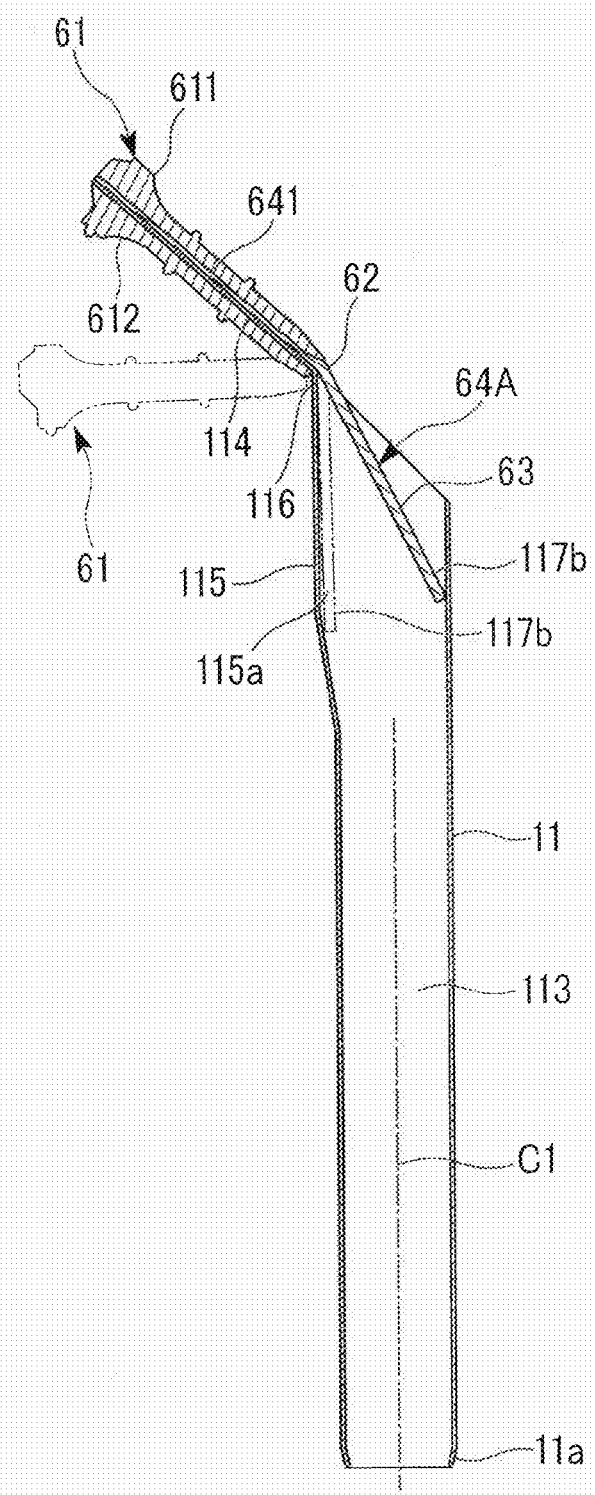
FIG. 43 is a cross-sectional view of another exemplary sheath for gastrostoma with a configuration in which the handle is covered with a lid via a lid hinge section other than the hinge section.

As illustrated in FIG. 43, the sheath for gastrostoma according to the invention may have a configuration in which an elongated plate lid member 64A configured by omitting the stopper projection piece 642 from the elongated plate lid member 64 as described above (sheath for gastrostoma 6A).

The handle 61 can be configured the same as that of the sheath for gastrostoma 6 as described above. The sheath for gastrostoma 6A has a configuration in which the lid 63 is elastically supported with elasticity of the hinge section 116 and elasticity of the lid hinge section 62 at a closed position at which the lid 63 closes the inner path 113 of the sheath body 11.

The lid 63 is formed as a tongue-shaped piece extending from the lid hinge section 62 and inserted in the sheath body 11. The lid 63 extends in a manner inclined toward the distal end of the sheath body 11 at an angle of smaller than 90 degrees with respect to the central axis C1 of the sheath body 11.

The distal end of the lid 63 is made to abut against a portion of the sheath body 11 at the side opposite to the hinge section 116 and the lid hinge section 62 across the inner path 113 when the lid 63 is pivoted from the closed position to the direction opposite to the open direction. Hereinafter, a portion of the sheath body 11 where the distal end of the lid 63 is made to abut will be referred to as a lid abutting section which is denoted by a reference numeral 117b. The hinge section 116 and the lid hinge section 62 are located at the side opposite to the lid abutting section 117b across the inner path 113.

The lid 63 can be pivoted toward the open direction against elasticity of the hinge section 116 and the lid hinge section 62 (i.e., pivoted in the direction in which the lid 63 is moved away from the lid abutting section 117b, i.e., clockwise in FIG. 43) and can return the closed position with elasticity of the hinge section 116 and the lid hinge section 62 from its pivoted position.

With this sheath for gastrostoma 6A, in a state in which, for example, a user of the sheath for gastrostoma 6A does not grasp the handle 61 with fingers and thus no external force is applied to the handle 61 and the lid 63, the lid 63 is elastically supported at the closed position (i.e., a position illustrated in FIG. 43) with the elasticity of the hinge section 116 and the lid hinge section 62.

Also, the lid hinge section 62 is configured to undergo elastic deformation (bending deformation) with smaller force than the hinge section 116 requires. Thus, with the sheath for gastrostoma 6A, elastic deformation of the lid hinge section 62 enables pivoting operation of the handle 61 freely regardless of the position of the lid 63. If, in the configuration of FIG. 43, no lid hinge section 62 is provided and the lid 63 is pivoted integrally with the handle 61, pivotation of the handle 61 in the counterclockwise direction in FIG. 43 is restricted when the lid 63 is abutting the lid abutting section 117b. Thus, the orientation of the handle 61 with respect to the sheath body 11 is restrained. On the contrary, in a configuration in which the lid hinge section 62 is provided as described above, the handle 61 can be pivoted counterclockwise in FIG. 43 (a position denoted by a reference numeral 61 of imaginary line in FIG. 43: hereinafter, also referred to as a "retracted position") even if the lid 63 is abutting the lid abutting section 117b. Accordingly, a greater degree of freedom of an angle (orientation) of the handle 61 with respect to the sheath body 11 is provided. Thus, the handle 61 can, for example, be kept at a desired orientation during insertion of the button for gastrostoma 2, thereby improving insertion operability of the button for gastrostoma 2. When, for example, the handle 61 is disposed at the retracted position, interference of the fingers which are grasping the handle 61 with the button for gastrostoma 2 to be inserted in the sheath body 11 can be avoided and thus interference of the inserting operation can be avoided.

The lid hinge section provides an increased degree of freedom of angle (orientation) of the handle 61 with respect to the sheath body 11 also in the sheath for gastrostoma 6 described with reference to FIG. 31.

Also, although the position of the lid hinge section 62 is near the hinge section 116, the lid hinge section 62 is provided separately from the hinge section 116. Thus, the lid 63 can be pivoted due to elastic deformation of the lid hinge section 62 when the handle 61 does not pivot about the hinge section 116. Accordingly, when the lid 63 is pivoted in the open direction by the sheath insertion aid 7 inserted in the inner path 113 of the sheath body 11 of the sheath for gastrostoma 6A, for example, following pivotation of the handle 61 to the lid 63 can be prevented. Thus, since change in the position of the handle 61 accompanying pivotation of the lid 63 can be prevented, failure of a user of the sheath for gastrostoma 6A to grasp the handle 61 with the fingers occurs less often, thereby securing good workability.

Figure 44A:
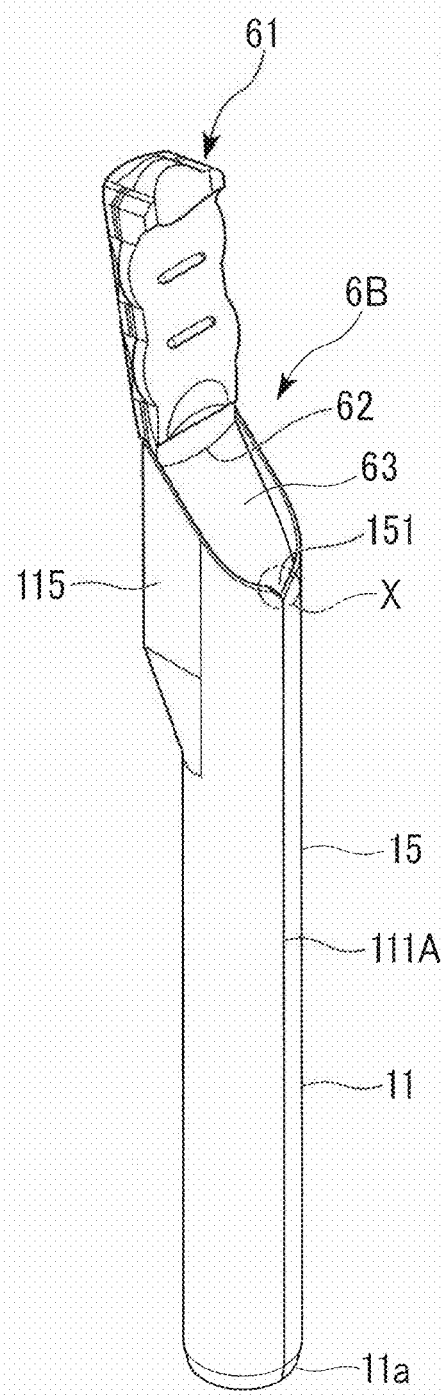
FIG. 44A is a perspective view of an exemplary sheath for gastrostoma in which a V-shaped distal notch section that can be used as a beginning point (starting point) of vertical splitting of the sheath body is formed in the sheath body.
Figure 44B:
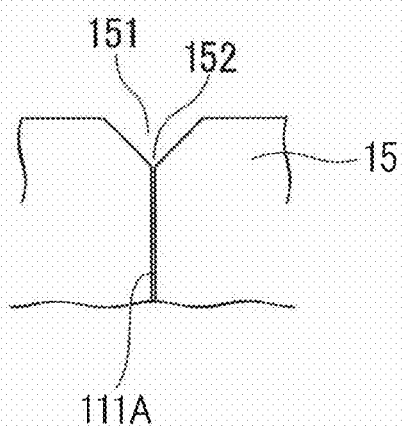
FIG. 44B is an enlarged front view (an enlarged front view of an area X in FIG. 44A) illustrating a configuration near the distal notch section of the sheath body of FIG. 44A.
Figure 46A:
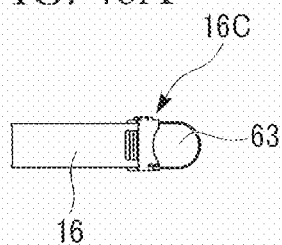
FIG. 46A is a top view of the sheath for gastrostoma of FIG. 45A with the lid closed.
Figures 46B, 46C, 46D, 46E:
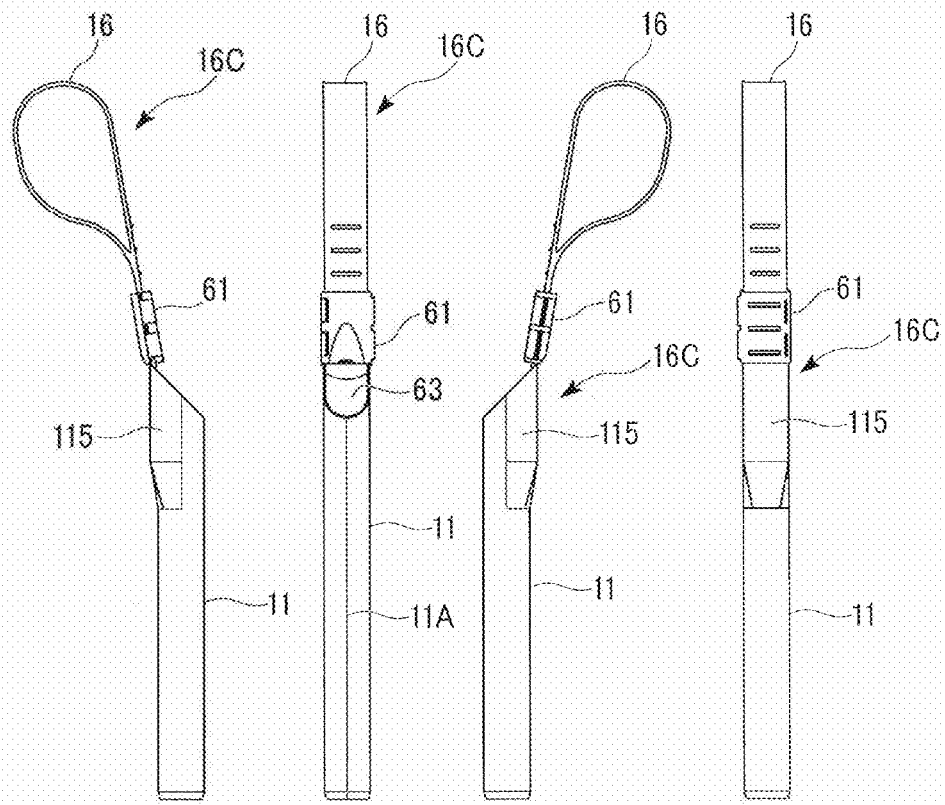
FIG. 46B is a left side view of the sheath for gastrostoma of FIG. 45A with the lid closed.
FIG. 46C is a front view of the sheath for gastrostoma of FIG. 45A with the lid closed.
FIG. 46D is a right side view of the sheath for gastrostoma of FIG. 45A with the lid closed.
FIG. 46E is a rear view of the sheath for gastrostoma of FIG. 45A with the lid closed.
Figure 46F:
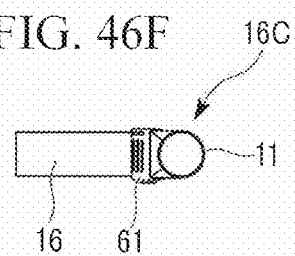
FIG. 46F is a bottom view of the sheath for gastrostoma of FIG. 45A with the lid closed.

As illustrated in FIGS. 44A and 44B, the sheath for gastrostoma according to the invention employs a sheath body 15 which includes a V-shaped distal notch section 151 configured to recess from an end surface at the base end of the sheath body 11 and a notched groove 111A formed to extend in the longitudinal direction (axial center direction) of the sheath body 11 from a depth section 152 of the distal notch section 151 toward the distal end of the seal body 11.

The sheath for gastrostoma which employs the sheath body 15 provides an advantage that, when the sheath body 15 is to be vertically split, vertical splitting can be performed easily and smoothly from the depth section 152 of the distal notch section 151.

FIGS. 44A and 44B illustrate a sheath for gastrostoma 6B configured by employing, in the sheath body 11 of the sheath for gastrostoma 6 described with reference to FIGS. 31A, 31B and other drawings, the sheath body 15 which includes the distal notch section 151 and the notched groove 111A which extends toward the distal end of the seal body 11 from the depth section 152 of the distal notch section 151. However, such a sheath body configured to include the distal notch section 151 and the notched groove 111A which extends toward the distal end of the seal body 11 from the depth section 152 of the distal notch section 151 is applicable to each embodiment according to the invention.

As illustrated in FIGS. 45A to 47, the sheath for gastrostoma according to the invention may also employ a configuration in which a grasping ring 16 is provided at the side opposite to the hinge section 116 of the handle 61. The user can insert the fingers to grasp the sheath for gastrostoma.

A sheath for gastrostoma 6C illustrated in FIGS. 45A to 47 has a schematic structure in which the grasping ring 16 is provided at the side opposite to the hinge section 116 of the handle 61 of the sheath for gastrostoma 6 described with reference to FIGS. 31A, 31B and other drawings. The sheath for gastrostoma 6C employs an elongated plate lid member with a ring 64B in place of the elongated plate lid member 64. The elongated plate lid member with the ring 64B is provided integrally with the grasping ring 16, the mounting section 641, the stopper projection piece 642, the lid hinge section 62 and the lid 63. The mounting section 641 of the elongated plate lid member with ring 64B is integrated with the handle 61.

The elongated plate lid member with ring 64B is configured to include the grasping ring 16 at the opposite side of the lid hinge section 62 across the mounting section 641 of the elongated plate lid member 64.

Here, the elongated plate lid member with ring 64B is integrally formed from a material with rubber elasticity, such as silicone rubber and elastomer.

The method (configuration) of integrally forming the mounting section 641 of the elongated plate lid member with ring 64B with the handle 61 may be the same as the method (configuration) of integrally forming the mounting section 641 of the elongated plate lid member 64 with the handle 61.

Figure 47:
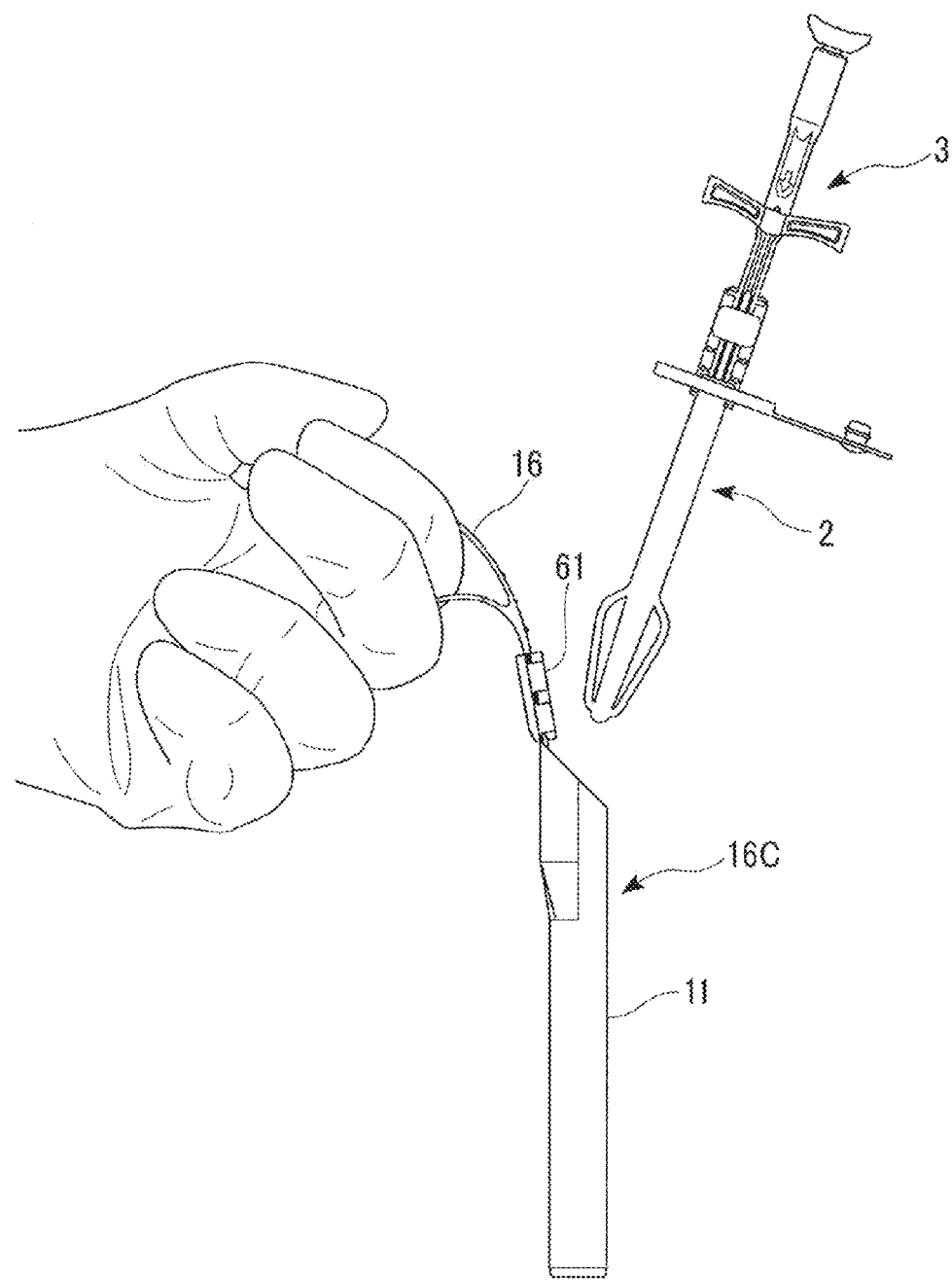
FIG. 47 illustrates an exemplary method of grasping the grasping ring of the sheath for gastrostoma of FIG. 45A with fingers.

As illustrated in FIG. 47, the sheath for gastrostoma 6C has an advantage that, since the user of the sheath for gastrostoma 6C can firmly hold the sheath body 11 by grasping the grasping ring 16 with fingers, the user can, for example, reliably insert the button for gastrostoma 2 in the sheath body 11 without dropping. In a procedure in which the sheath insertion aid 7 is inserted in the sheath body 11 to assemble the sheath with insertion aid 70, insertion and assembly can be reliably performed similarly.

The user may preferably grasp the grasping ring 16 with the fingers in the following manner from the viewpoint of reliability. As illustrated in FIG. 47, one or more fingers (e.g., one or more of the middle finger, the third finger and the little finger) of one hand are placed inside the grasping ring 16 to be caught in the grasping ring 16.

However, the method of grasping the grasping ring 16 is not limited to the same. Another method of grasping the grasping ring 16 may be employed in which, for example, one or more fingers (e.g., one or more of the middle finger, the third finger and the little finger) of one hand are placed inside the grasping ring 16 to be caught in the grasping ring 16 and the handle 61 is grasped with the rest of the fingers of the same hand.

Note that the grasping ring 16 is not necessarily made of a material with rubber elasticity and is thus flexible. Instead, the grasping ring 16 may be formed of rigid resin. It is advantageous, however, to employ a grasping ring 16 made of a material with rubber elasticity and thus configured to be excellent in bendability and flexibility from the view point of good workability since a grasping ring 16 made of a hard material may interfere with the operation.

In addition, it suffices that the grasping ring 16 be securely fixed to the handle 61 at the side opposite to the hinge section 116 of the handle 61. Thus, the elongated plate lid member with the ring 64B is not necessarily employed and the grasping ring 16 may be fixed to the handle as a separate member from members that constitute the mounting section 641, the lid hinge section 62 and the lid 63.

Moreover, although a configuration in which the grasping ring 16 is employed in the sheath for gastro stoma 6 described with reference to FIGS. 31A, 31B and other drawings has been illustrated in FIGS. 45A to 47, the configuration in which the grasping ring 16 is provided at the side opposite to the hinge section 116 of the handle as described above is applicable to each embodiment according to the invention.

Furthermore, the invention provides a gastrostomy catheter kit which includes the sheath for gastrostoma 1, the button for gastrostoma 2, the obturator 3 and the dilator 5. Preferably, the gastrostomy catheter kit is configured to, for example, collectively carry the sheath for gastrostoma 1, the button for gastrostoma 2, the obturator 3 and the dilator 5 in a casing. The sheath for gastrostoma 1 and the dilator 5 may be a sheathed dilator 5A in which the sheath for gastrostoma 1 is disposed over the dilator 5. The gastrostomy catheter kit may include a sheath for gastrostoma for replacement or a sheath with insertion aid 70 in which the insert sheath insertion aid 7 is inserted in the sheath for gastrostoma for replacement. A gastrostomy catheter kit with a sheath for gastrostoma for replacement which does not constitute the sheath with insertion aid 70 may include the sheath insertion aid 7 which can be inserted in the sheath body of the sheath for gastrostoma for replacement. The sheath for gastrostoma for replacement, the sheath with insertion aid 70 and the sheath insertion aid 7 to be employed are housed in the casing.

Of course, the gastrostomy catheter kit may further include a guidewire.

Note that the invention is not limited to a configuration in which the lid and the handle pivot integrally with each other.

For example, a configuration may be employed in which a lid is pivotably provided on the sheath body via the hinge section separately from the handle.

Also, the invention includes a configuration with no lid provided. In this case, for example, a plug member which is removably fit into the base end of the sheath body may be provided to open and close the inner path of the sheath body. With the plug member closing the inner path, air supply from the endoscope can be easily controlled.

Also, the invention includes a configuration in which a diameter (inner diameter) of the inner path of the sheath for gastrostoma is the same or larger than the maximum outer diameter of the extended indwelling section.

INDUSTRIAL APPLICABILITY

As described above, according to the invention, it is possible to lower insertion resistance at the time of placing a button gastrostomy catheter in the patient's body during gastrostomy and catheter replacement in which a gastrostomy catheter is inserted in a fistula and left. A stable endoscopic visual field during surgery can be provided.

The invention claimed is:
1. A sheath for gastrostoma, comprising:
a cylindrical sheath body having a through-hole forming an inner path and configured to receive a gastrostomy catheter in the inner path;
a handle protruding from one longitudinal end of the cylindrical sheath body and connected pivotably to the longitudinal end via a hinge section of the cylindrical sheath body; and
a lid connected to the handle via a lid hinge section of the cylindrical sheath body and configured to open and close the inner path in the cylindrical sheath body through pivotation about the lid hinge section,
wherein the lid is configured to close the inner path when the lid is in a closed position and has a distal end abut against a lid abutting section of the cylindrical sheath body, and open the inner path by pivotation from the closed position in an open direction toward a distal end of the cylindrical sheath body opposite to the longitudinal end, the handle has a stopper projection piece protruding from the handle and positioned along an inner surface of the cylindrical sheath body opposite to the lid abutting section across the inner path, and the stopper projection piece is configured such that when the lid receives a force that causes the lid to pivot from the closed position in the open direction, the stopper projection piece is pressed against the inner surface of the cylindrical sheath body such that pivotation of the stopper projection piece with respect to the cylindrical sheath body is restricted.

2. The sheath for gastrostoma according to claim 1, wherein the lid has a proximal end connected to the handle via the lid hinge section, and the hinge section and the lid hinge section are on an opposite side of the lid abutting section across the inner path.

3. The sheath for gastrostoma according to claim 1, wherein the stopper projection piece comprises a material with rubber elasticity.

4. The sheath for gastrostoma according to claim 1, wherein the lid hinge section comprises a material with rubber elasticity and forms a lid elastic support member configured to elastically support the lid at the closed position.

5. The sheath for gastrostoma according to claim 1, wherein the lid hinge section and the lid comprise a material with rubber elasticity.

6. The sheath for gastrostoma according to claim 1, wherein the handle has a mounting section which forms a part of the handle, and the mounting section, the lid hinge section and the lid comprise a synthetic resin.

7. The sheath for gastrostoma according to claim 1, wherein the handle has a handle main piece which forms a part or all of the handle, and the handle main piece, the cylindrical sheath body and the hinge section are formed integrally as one component comprising a synthetic resin.

8. The sheath for gastrostoma according to claim 1, wherein the cylindrical sheath body has at least one notch section that facilitates vertical splitting of the cylindrical sheath body in a longitudinal direction.

9. The sheath for gastrostoma according to claim 8, wherein the notch section is a notched groove formed in the cylindrical sheath body such that the notched groove does not penetrate the cylindrical sheath body in a radial direction of the cylindrical sheath body and leaves at least one uncut portion between an inside of the cylindrical sheath body and a bottom of the notched groove.

10. The sheath for gastrostoma according to claim 9, wherein the sheath body includes a V-shaped distal notch section forming a recess from an end surface on the longitudinal end of the cylindrical sheath body, and the notched groove extends toward the distal end of the cylindrical sheath body from a depth section of the V-shaped distal notch section.

11. The sheath for gastrostoma according to claim 9, wherein the at least one uncut portion is fracturable by applying a load to the inner surface of the cylindrical sheath body in a range of from 0.5N to 5N.

12. The sheath for gastrostoma according to claim 8, wherein the notch section is a slit extending along a longitudinal direction of the cylindrical sheath body and having a length shorter than an entire length of the cylindrical sheath body in the longitudinal direction, and the cylindrical sheath body has an uncut portion where no slit is formed along a virtual line extended from the slit.

13. The sheath for gastrostoma according to claim 8, wherein the notch section is formed in a wedge-shaped cross-section having an opening width that increases from the inner surface toward an outer surface of the cylindrical sheath body.

14. The sheath for gastrostoma according to claim 8, wherein the handle is located at a position where the handle does not interfere with the notch section in a circumferential direction of the cylindrical sheath body.

15. The sheath for gastrostoma according to claim 14, wherein the notch section is formed only at one position along the circumferential direction of the cylindrical sheath body, and the cylindrical sheath body has only one handle.

16. The sheath for gastrostoma according to claim 1, wherein the cylindrical sheath body has an end surface on the longitudinal end, and the end surface is inclined with respect to an axial center of the cylindrical sheath body.

17. The sheath for gastrostoma according to claim 1, wherein the cylindrical sheath body comprises a fluororesin.

18. The sheath for gastrostoma according to claim 17, wherein the fluororesin comprises at least one of PTFE, ETFE and FEP.

19. The sheath for gastrostoma according to claim 1, wherein the cylindrical sheath body is configured such that the cylindrical sheath body is detachably placeable outside of a dilator configured to form a fistula.

20. The sheath for gastrostoma according to claim 1, wherein the cylindrical sheath body has an inner diameter smaller than a maximum outer diameter of an indwelling section of the gastrostomy catheter when the indwelling section is in a reduced-diameter state under an extending force applied by an obturator.

21. The sheath for gastrostoma according to claim 20, wherein the cylindrical sheath body is vertically splittable when the gastrostomy catheter is inserted with the indwelling section in the reduced-diameter state.

22. The sheath for gastrostoma according to claim 1, wherein the cylindrical sheath body comprises a stretch-deformable material such that the cylindrical sheath body is radially expandable.

23. The sheath for gastrostoma according to claim 1, wherein the cylindrical sheath body has an inner diameter larger than a maximum outer diameter of an indwelling section of the gastrostomy catheter when the indwelling section is in a reduced-diameter state under an extending force applied by an obturator.

24. The sheath for gastrostoma according to claim 1, wherein the cylindrical sheath body is configured such that a sheath insertion aid having a rod-shaped appearance is receivable in the sheath body, and the sheath insertion aid includes a rod-shaped body and a tapered distal section having a tapering structure protruding from one longitudinal end of the rod-shaped body.

25. The sheath for gastrostoma according to claim 24, wherein the sheath insertion aid has a guidewire insertion hole which penetrates the sheath insertion aid along a longitudinal direction of the sheath insertion aid.

26. The sheath for gastrostoma according to claim 24, wherein the sheath insertion aid is configured such that the sheath insertion aid functions as a dilator configured to form a fistula.

27. The sheath for gastrostoma according to claim 1, wherein the cylindrical sheath body has a sheath insertion aid inserted in the cylindrical sheath body, and the sheath insertion body has a rod-shaped body and a tapered distal section having a tapering structure at one longitudinal end of the rod-shaped body.

28. A gastrostomy catheter kit, comprising:
a gastrostomy catheter configured to introduce a nutrient or a chemical into a stomach of a subject from outside of a body of the subject;
an obturator; and
the sheath of claim 1,
wherein the gastrostomy catheter includes a tubular section having an inner path that allows introduction of the nutrient or the chemical into the stomach from outside of the body, and an indwelling section attached to a distal section of the tubular section and formed in a dome shape protruding radially outward of the tubular section such that the indwelling section has a diameter variable by an extending force applied by an obturator configured to extend the indwelling section, and the sheath of claim 2 is configured to receive the gastrostomy catheter having the indwelling section in a reduced-diameter state by the obturator when the sheath is inserted in a fistula.

29. The gastrostomy catheter kit according to claim 28, wherein the obturator includes an outer case, a pushing rod for extension which includes a rod body inserted in the outer case to be movable in a longitudinal direction of the outer case and a stopper configured to anchor the gastrostomy catheter to the outer case, and
the obturator is configured such that in a state in which the gastrostomy catheter is anchored to the outer case with the stopper, an operator inserts a distal end of the pushing rod for extension protruding from the outer case of the rod body in the indwelling section of the gastrostomy catheter and presses the most distal section of the indwelling section to extend the indwelling section.

30. The gastrostomy catheter kit according to claim 28, wherein the gastrostomy catheter and the obturator include a guidewire path, and the obturator is configured to reduce the diameter of the indwelling section of the gastrostomy catheter in a state in which the obturator is positioned outside of a guidewire inserted in the gastrostomy catheter.

31. The gastrostomy catheter kit according to claim 28, wherein the sheath for gastrostoma is a sheath for gastrostoma for replacement, and the gastrostomy catheter in which the indwelling section is in the reduced-diameter state by the obturator is inserted in the sheath for gastrostoma.

32. The gastrostomy catheter kit according to claim 31, further comprising:
a sheath for gastrostoma having a sheath insertion aid inserted in the sheath body, the sheath insertion aid has a rod-shaped body and a tapered distal section having a tapering structure at one longitudinal end of the rod-shaped body,
wherein the sheath for gastrostoma having the insertion aid is the sheath for gastrostoma for replacement.

33. A sheathed dilator, comprising:
a dilator configured to form a fistula; and
the sheath of claim 1 positioned outside the dilator.

34. The sheathed dilator according to claim 33, wherein the dilator includes a guidewire path which penetrates the dilator in the longitudinal direction.

35. The sheathed dilator according to claim 33, wherein the dilator has a scale on a peripheral surface thereof for measurement of a distance between an inner stomach wall and an outer body surface.

36. The sheathed dilator according to claim 35, wherein the cylindrical sheath body has transparency that allows observation of a scale of the dilator from outside.

37. The sheathed dilator according to claim 33, wherein the dilator has a narrow-diameter dilator and a large-diameter dilator which are integrated together, the narrow-diameter dilator includes a guidewire path inside thereof, and the large-diameter dilator is positioned outside of the narrow-diameter dilator and assembled to the narrow-diameter dilator.

38. A gastrostomy catheter kit, comprising:
a gastrostomy catheter configured to percutaneously introduce a nutrient or a chemical into a stomach of a subject from outside of a body of the subject;
an obturator; and
the sheathed dilator of claim 33,
wherein the gastrostomy catheter includes a tubular section having an inner path that allows introduction of the nutrient or the chemical into the stomach from outside of the body, and an indwelling section attached to a distal section of the tubular section and formed in a dome shape protruding radially outward of the tubular section such that the indwelling section has a diameter variable by an extending force applied by an obturator configured to extend the indwelling section, and the sheath of claim 34 is configured to receive the gastrostomy catheter having an indwelling section in a reduced-diameter state by the obturator when the sheath is inserted in a fistula.

39. A method of splitting a sheath for gastrostoma, comprising:
inserting, in the cylindrical sheath body of the sheath of claim 1, a medical device having an outer diameter larger than an inner diameter of the cylindrical sheath body such that the cylindrical sheath body is split in at least one portion in a circumferential direction along an entire longitudinal direction length of the cylindrical sheath body.

40. The method of splitting a sheath for gastrostoma according to claim 39, wherein the inserting of the medical device comprises inserting a gastrostomy catheter having an indwelling section in a reduced-diameter state by an extending force from an obturator, and the indwelling section has a maximum outer diameter larger than an inner diameter of the cylindrical sheath body when the indwelling section is in the reduced-diameter state.

* * * * *